(12) United States Patent
Marie-Nelly et al.

(10) Patent No.: US 12,198,344 B2
(45) Date of Patent: Jan. 14, 2025

(54) AUTONOMOUS CELL IMAGING AND MODELING SYSTEM

(71) Applicant: Insitro, Inc., South San Francisco, CA (US)

(72) Inventors: Hervé Marie-Nelly, San Francisco, CA (US); Jeevaa Velayutham, Shah Alam (MY); Zachary Phillips, San Francisco, CA (US); Shengjiang Tu, Foster City, CA (US)

(73) Assignee: Insitro, Inc., South San Francisco, CA (US)

( * ) Notice: Subject to any disclaimer, the term of this patent is extended or adjusted under 35 U.S.C. 154(b) by 0 days.

(21) Appl. No.: 18/527,037

(22) Filed: Dec. 1, 2023

(65) Prior Publication Data

US 2024/0104734 A1   Mar. 28, 2024

Related U.S. Application Data

(60) Division of application No. 18/111,405, filed on Feb. 17, 2023, now Pat. No. 11,875,506, which is a
(Continued)

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/4848* (2013.01); *G01N 15/1429* (2013.01);
(Continued)

(58) Field of Classification Search
None
See application file for complete search history.

(56) References Cited

U.S. PATENT DOCUMENTS

| 10,467,754 B1 | 11/2019 | Ando et al. |
| 11,423,256 B2 | 8/2022 | Marie-Nelly et al. |

(Continued)

FOREIGN PATENT DOCUMENTS

| WO | WO-2010082096 A2 | 7/2010 |
| WO | WO-2020113237 A1 | 6/2020 |
| WO | WO-2023023507 A1 | 2/2023 |

OTHER PUBLICATIONS

Goldsborough, Peter, et al. "CytoGAN: generative modeling of cell images." BioRxiv (2017): 227645. (Year: 2017).*
(Continued)

*Primary Examiner* — Samah A Beg
(74) *Attorney, Agent, or Firm* — MORRISON & FOERSTER LLP

(57) ABSTRACT

The present disclosure relates generally to an autonomous cell imaging and modeling platform, and more specifically to machine-learning techniques for using microscopy imaging data to continuously study live biological cells. The autonomous cell imaging and modeling platform can be applied to evaluate various cellular processes, such as cellular differentiation, optimization of cell culture (e.g., in-plate cytometry), disease modeling, histopathology imaging, and genetic and chemical screening, using a dynamic universal imaging system. In some embodiments, the platform comprises a set of label-free computational imaging techniques, self-supervised learning models, and robotic devices configured in an autonomous imaging system to study positional and morphological characteristics in particular cellular substructures of a cell culture in an efficient and non-destructive manner over time.

24 Claims, 37 Drawing Sheets
(27 of 37 Drawing Sheet(s) Filed in Color)

Related U.S. Application Data continuation of application No. PCT/US2022/080200, filed on Nov. 19, 2022.

(60) Provisional application No. 63/281,536, filed on Nov. 19, 2021.

(51) Int. Cl.
  *G01N 15/1429* (2024.01)
  *G16H 20/00* (2018.01)
(52) U.S. Cl.
  CPC ... *G16H 20/00* (2018.01); *G06T 2207/10064* (2013.01); *G06T 2207/20036* (2013.01); *G06T 2207/30024* (2013.01)

(56) References Cited

U.S. PATENT DOCUMENTS

| | | | |
|---|---|---|---|
| 11,875,506 | B1 | 1/2024 | Marie-Nelly et al. |
| 11,978,206 | B2 | 5/2024 | Marie-Nelly et al. |
| 12,002,559 | B2 | 6/2024 | Casale et al. |
| 2008/0201083 | A1* | 8/2008 | Hata .................. G06V 20/698 702/21 |
| 2017/0204359 | A1* | 7/2017 | Ando ................... C12M 41/36 |
| 2019/0295721 | A1 | 9/2019 | Madabhushi et al. |
| 2019/0369098 | A1 | 12/2019 | Hedge et al. |
| 2019/0371471 | A1 | 12/2019 | Tan et al. |
| 2020/0005461 | A1 | 1/2020 | Yip |
| 2020/0105413 | A1 | 4/2020 | Madimirova et al. |
| 2020/0258223 | A1 | 8/2020 | Yip et al. |
| 2020/0388287 | A1 | 12/2020 | Anushiravani et al. |
| 2021/0172931 | A1 | 6/2021 | Larsen et al. |
| 2021/0200989 | A1 | 7/2021 | Courtiol et al. |
| 2021/0210205 | A1 | 7/2021 | Drake et al. |
| 2021/0256699 | A1 | 8/2021 | Wainrib et al. |
| 2021/0271847 | A1 | 9/2021 | Courtiol et al. |
| 2021/0374553 | A1 | 12/2021 | Li et al. |
| 2022/0059240 | A1 | 2/2022 | Schaeffer et al. |
| 2022/0261668 | A1 | 8/2022 | Stumpe et al. |
| 2022/0292674 | A1 | 9/2022 | Braman et al. |
| 2022/0367053 | A1 | 11/2022 | Mahmood et al. |
| 2023/0026189 | A1* | 1/2023 | Kamato ............. G01N 33/5008 |
| 2023/0036156 | A1* | 2/2023 | Ho ....................... G06V 20/698 |
| 2023/0142909 | A1 | 5/2023 | Zhao |
| 2023/0154627 | A1 | 5/2023 | Irving et al. |
| 2023/0245477 | A1 | 8/2023 | Rothrock et al. |
| 2023/0360758 | A1 | 11/2023 | Casale et al. |
| 2024/0119593 | A1 | 4/2024 | Marie-Nelly et al. |
| 2024/0273718 | A1 | 8/2024 | Probert et al. |
| 2024/0274254 | A1 | 8/2024 | Casale et al. |
| 2024/0274255 | A1 | 8/2024 | Casale et al. |

OTHER PUBLICATIONS

Ubbens, Jordan, et al. "Latent space phenotyping: automatic image-based phenotyping for treatment studies." Plant Phenomics (2020). (Year: 2020).*

Galton, (1886). "Regression Towards Mediocrity in Hereditary Stature," The Journal of the Anthropological Institute of Great Britain and Ireland, 15:246-263.

International Search Report and Written Opinion received for International Patent Application No. PCT/US2022/080200 mailed on May 23, 2023, 20 pages.

Wells et al., (2009). "Phase contrast microscopy analysis of breast tissue: differences in benign vs. malignant epithelium and stroma," Anal Quant Cytol Histol., 31(4):197-207, 18 pages.

Taylor-Weiner et al., (2021). "A machine learning approach enables quantitative measurement of liver histology and disease monitoring in NASH," Hepatology, 74(1):133-147.

Arslan et al., (2022). "Deep learning can predict multi-omic biomarkers from routine pathology images: A systematic large-scale study," BioRxiv, 477189, 44 pages.

Courtiol et al., (2019). "Deep learning-based classification of mesothelioma improves prediction of patient outcome," Nature Medicine, 25(10):1519-1525.

Courtiol et al., (2020). "Classification And Disease Localization In Histopathology Using Only Global Labels: A Weakly-Supervised Approach," arXiv, 1802.02212, 13 pages.

De Jong et al., (2021). "Towards Realizing the Vision of Precision Medicine: AI Based Prediction of Clinical Drug Response Authors," Brain, 144:1738-1750.

Ingale et al., (2023). "Prediction of met overexpression in non-small cell lung adenocarcinomas from hematoxylin and eosin images," arXiv, 2310.07682, 45 pages.

International Search Report and Written Opinion received for International Patent Application No. PCT/US2022/075006 mailed on Jan. 27, 2023, 19 pages.

Kopf et al., (2021). "Latent representation learning in biology and translational medicine," Patterns, 2(3):100198, 15 pages.

Liu et al., (2018). "An integrated toga pan-cancer clinical data resource to drive high-quality survival outcome analytics," Cell, 173(2):400-416, 29 pages.

Amaro et al., (2021). "A Machine Learning Approach Enables Quantitative Measurement of Liver Histology and Disease Monitoring in NASH," Hepatology, 74(1):133-147.

Chao et al., (2021). "MAPS: machine-assisted phenotype scoring enables rapid functional assessment of genetic variants by high-content microscopy," BMC Bioinformatics, 22:202, 19 pages.

Clark et al., (2011). "Analysis of efficacy and side effects in CATIE demonstrates drug response subgroups and potential for personalized medicine," Schizophrenia Research, 132(2-3):114-120, 15 pages.

Han et al., (2019). "GCN-MF: disease-gene association identification by graph convolutional networks and matrix factorization," Proceedings of the 25th ACM SIGKDD International Conference on Knowledge Discovery & Data Mining, pp. 705-713, 10 pages.

International Search Report and Written Opinion received for International Patent Application No. PCT/US2024/015870 mailed on Aug. 5, 2024, 36 pages.

Invitation to Pay Additional Fees, Partial Search Report and Provisional Opinion for International Patent Application No. PCT/US2024/015870 mailed on Jun. 14, 2024, 25 pages.

Li et al., (2015). "Identification of type 2 diabetes subgroups through topological analysis of patient similarity," Science Translational Medicine 7(311):311ra174, 17 pages.

Li et al., (2021). "Deep learning-based predictive biomarker of pathological complete response to neoadjuvant chemotherapy from histological images in breast cancer," J Transl Med, 19:348, 13 pages.

Schulam et al., (2016). "Disease trajectory maps," Advances in Neural Information Processing Systems, 29, 9 pages.

Sui et al., (2022). "A deep learning model designed for Raman spectroscopy with a novel hyperparameter optimization method," Spectrochim Acta A Mol Biomol Spectrosc, 280:121560, 9 pages.

* cited by examiner

1200

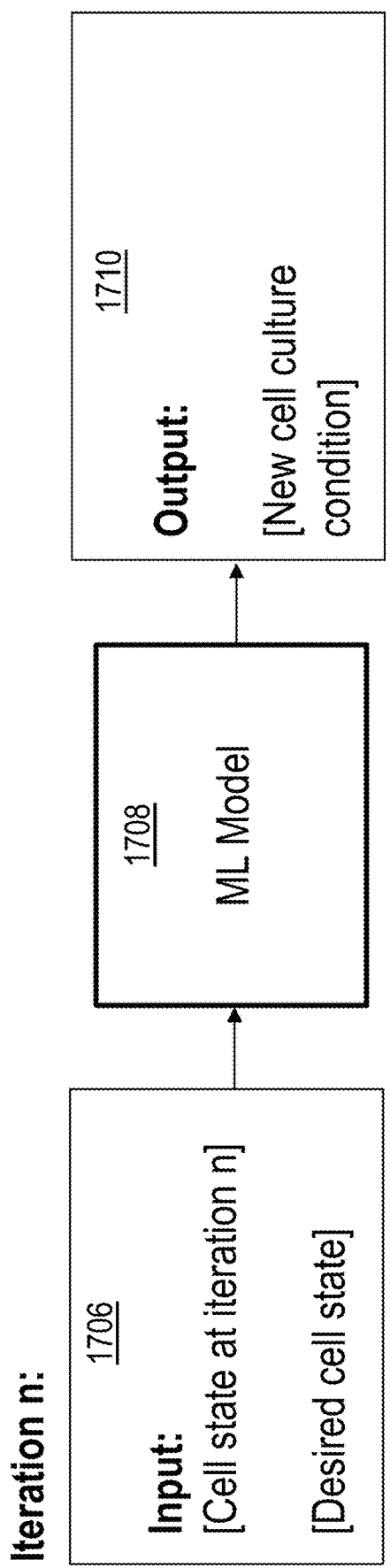
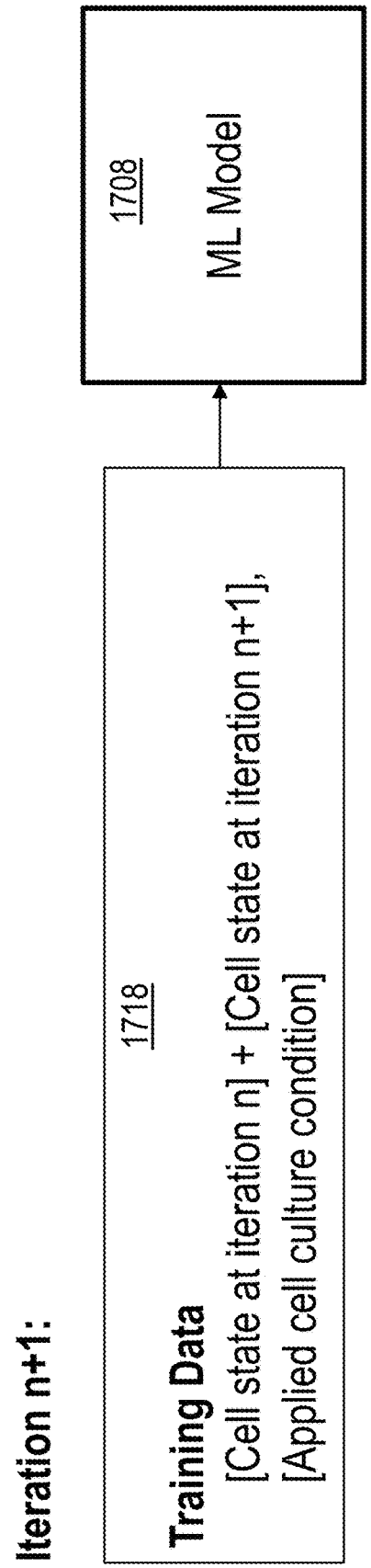
FIG. 17A
FIG. 17B

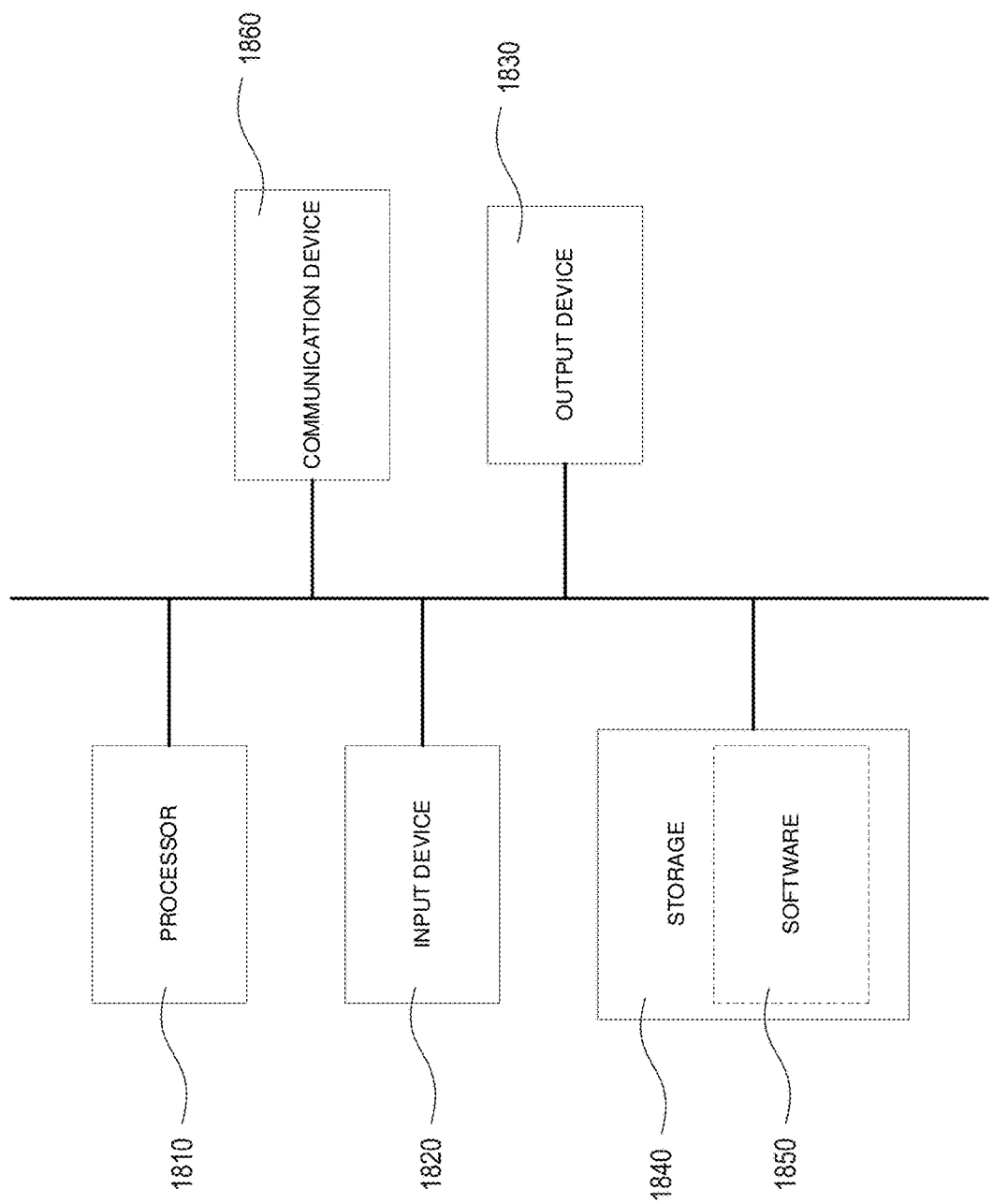

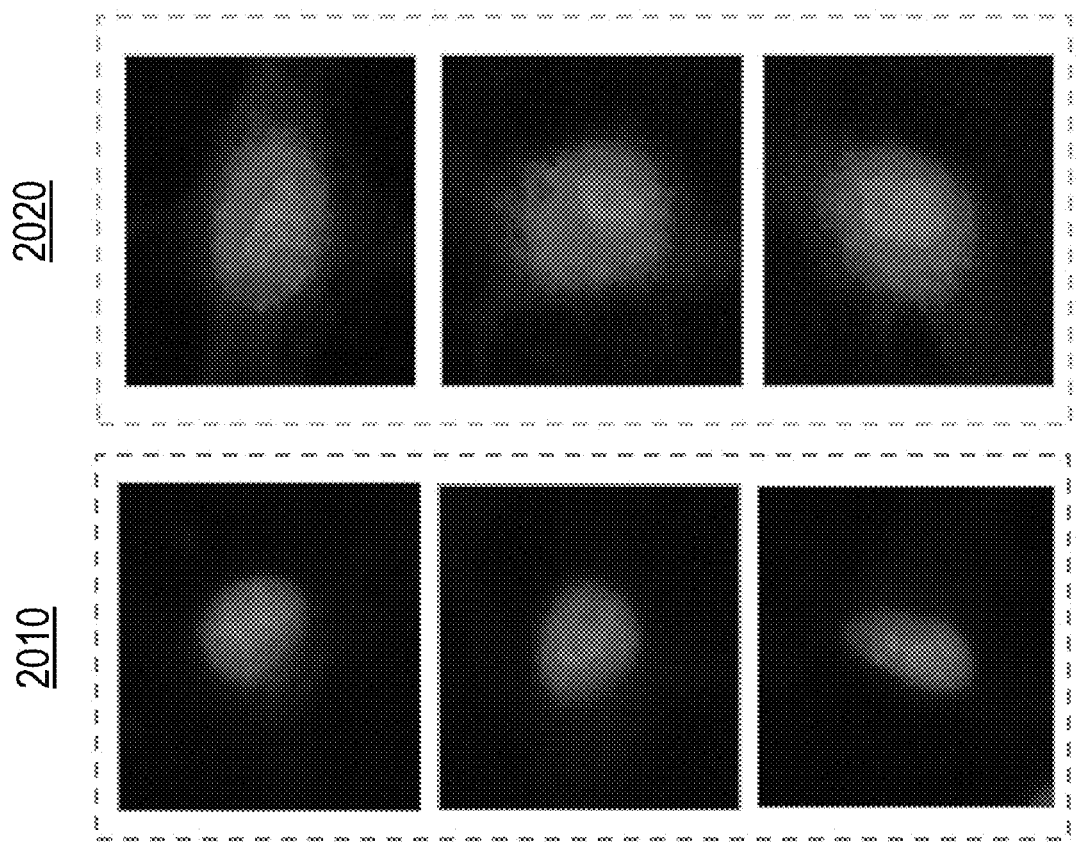
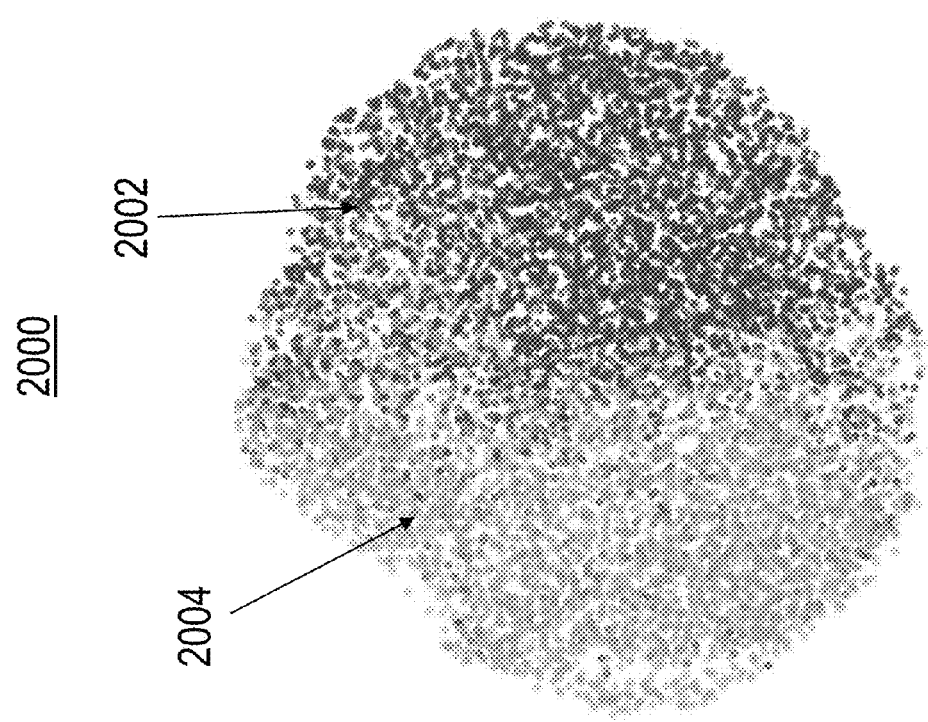
FIG. 20A

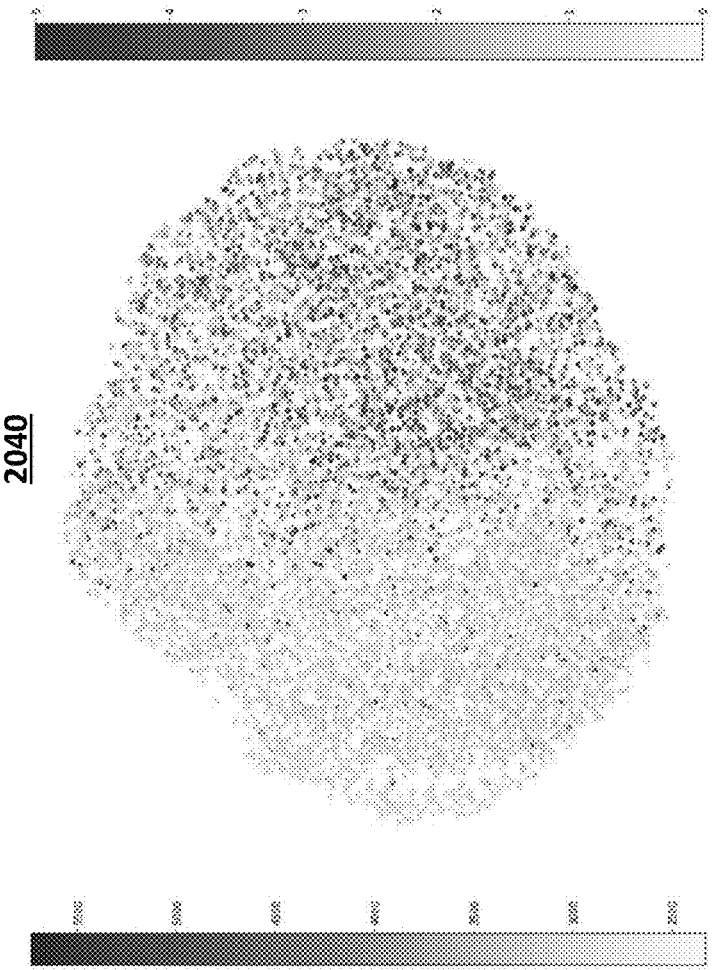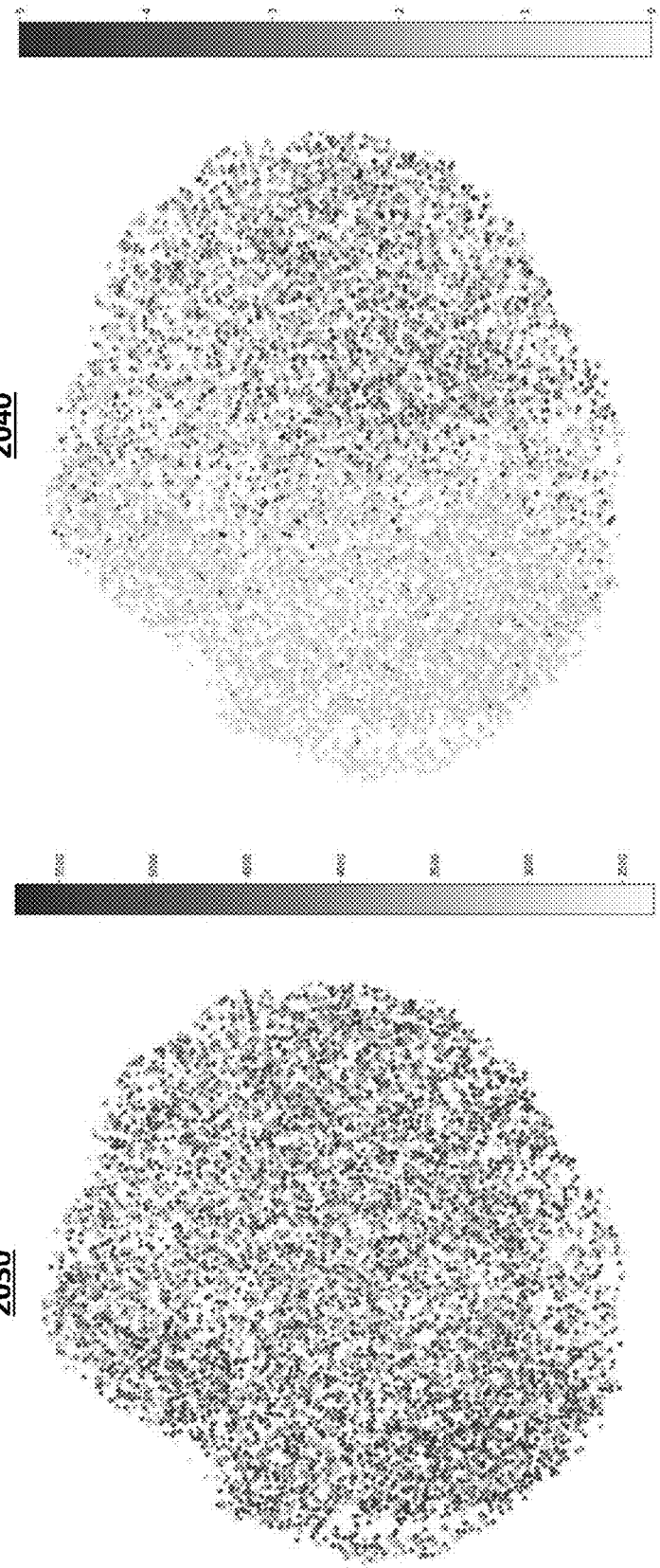
FIG. 20B

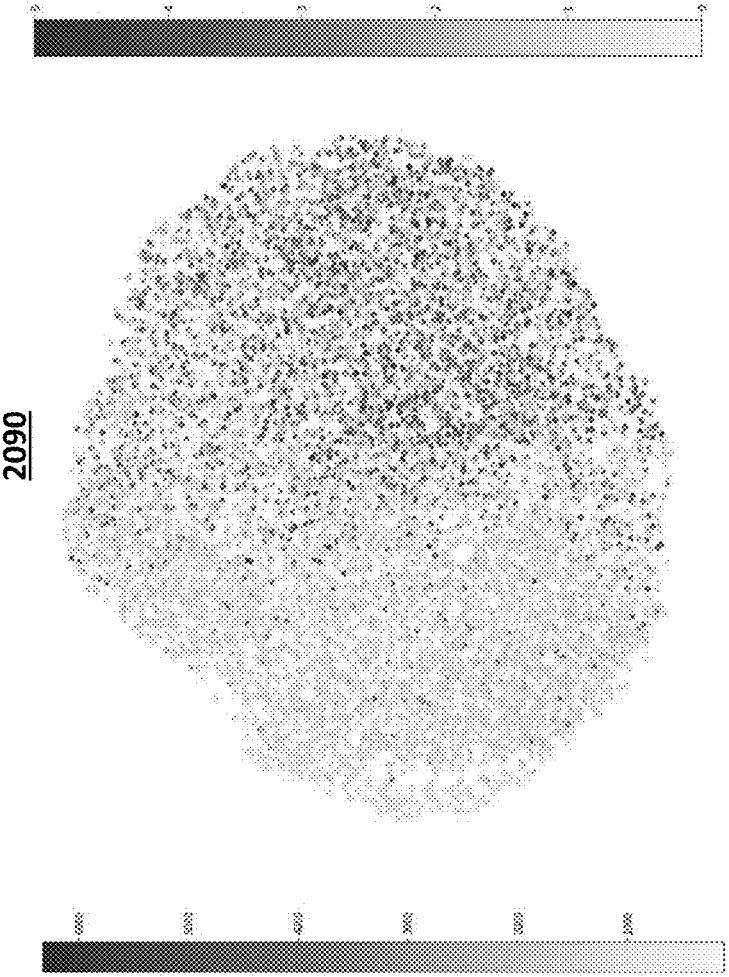
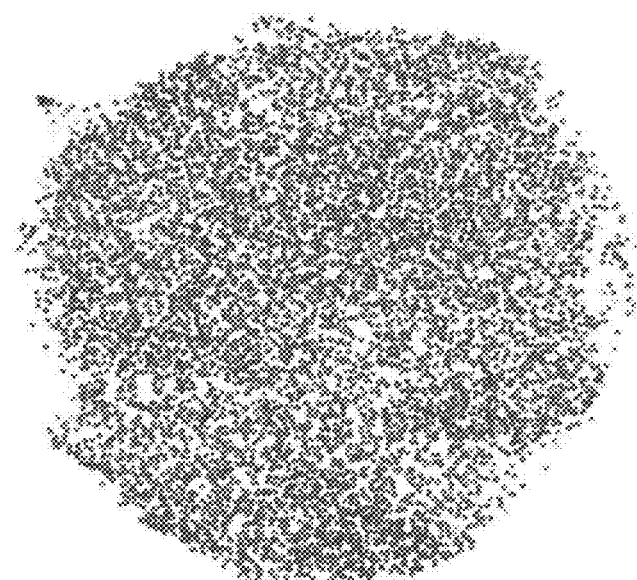
FIG. 20D

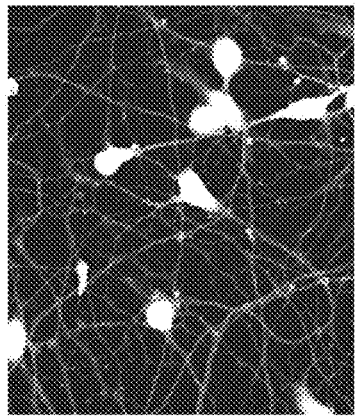
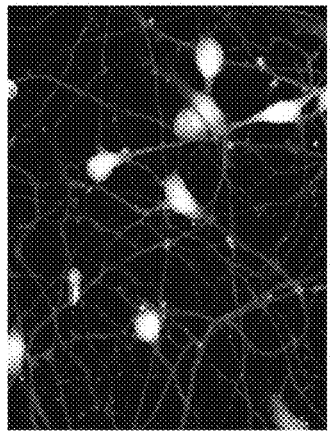
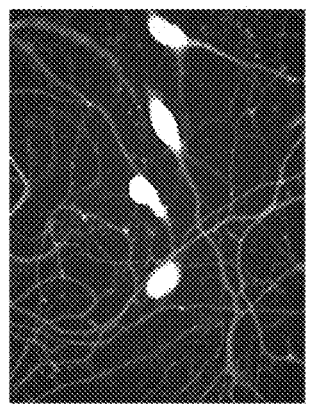
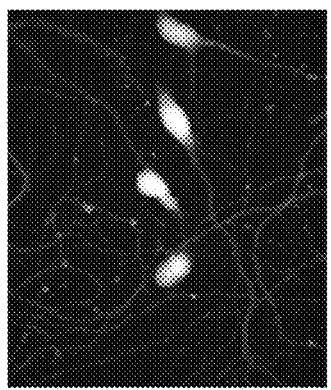
FIG. 22

Day 0
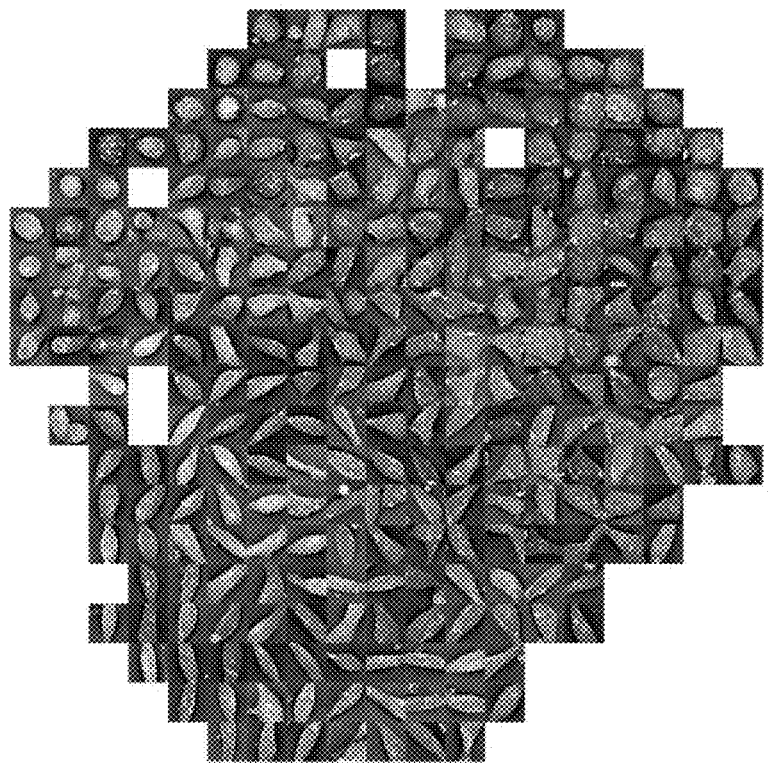
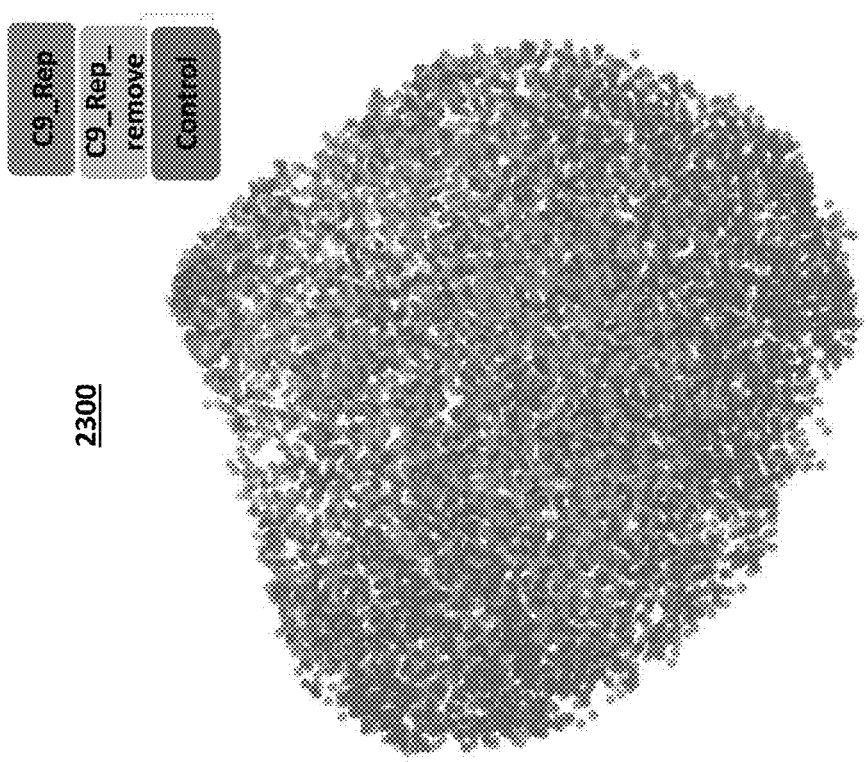
FIG. 23A

Day 1
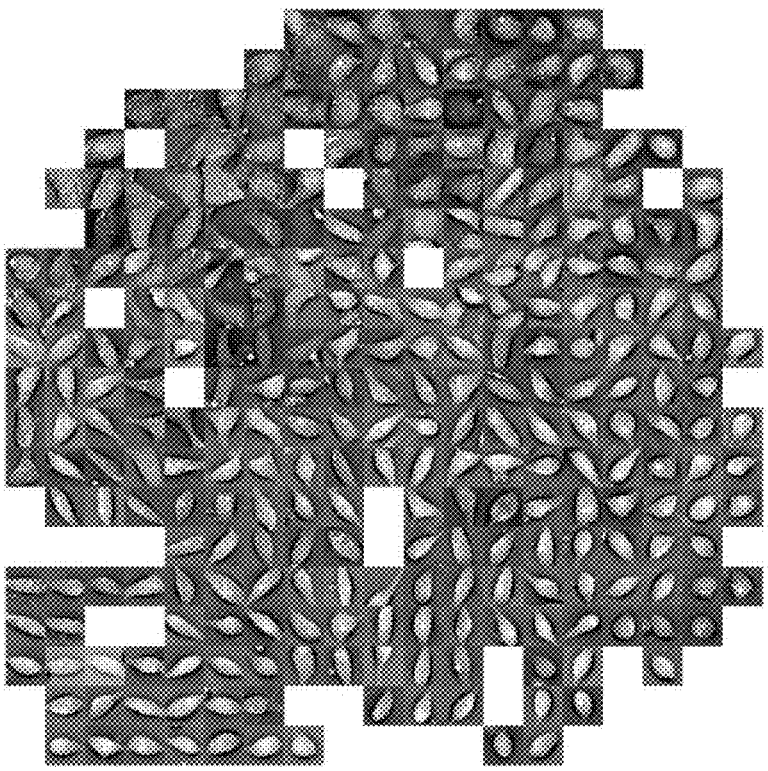
2360
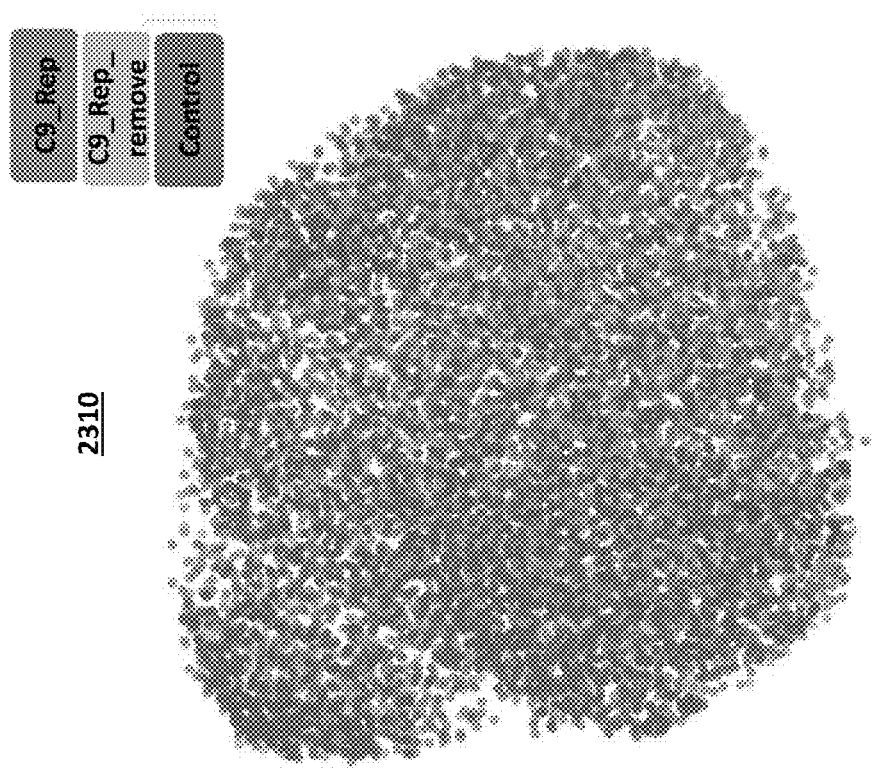
2310
FIG. 23B

Day 2
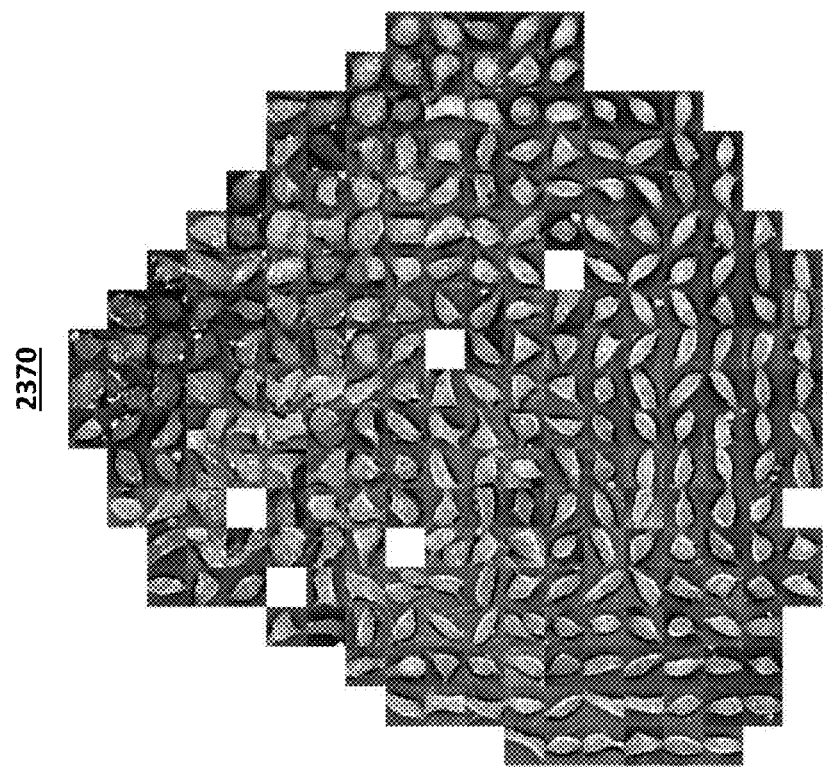
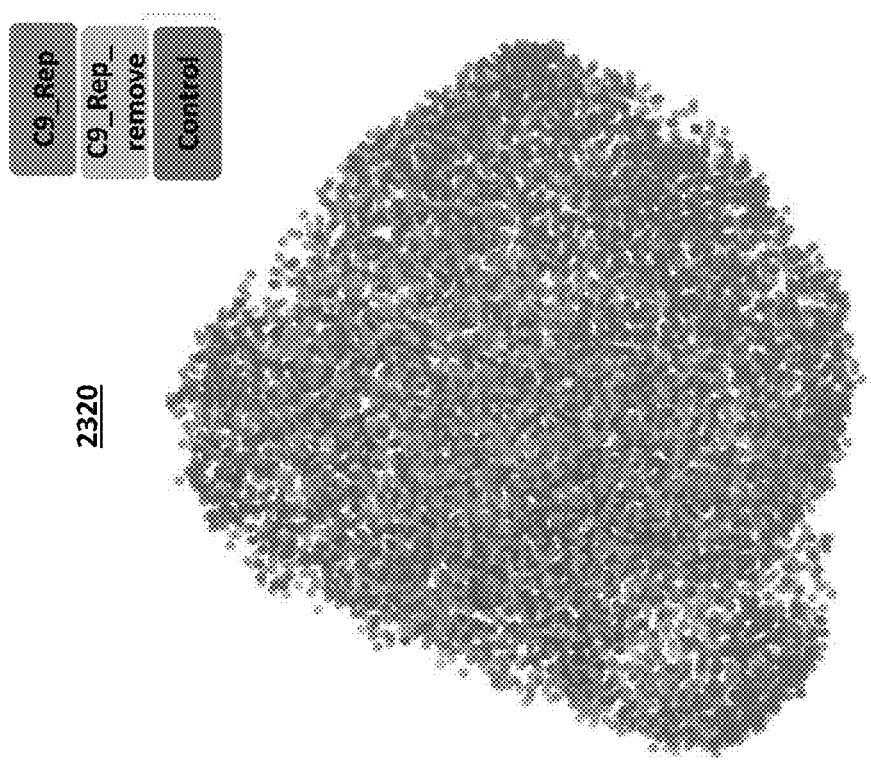
FIG. 23C

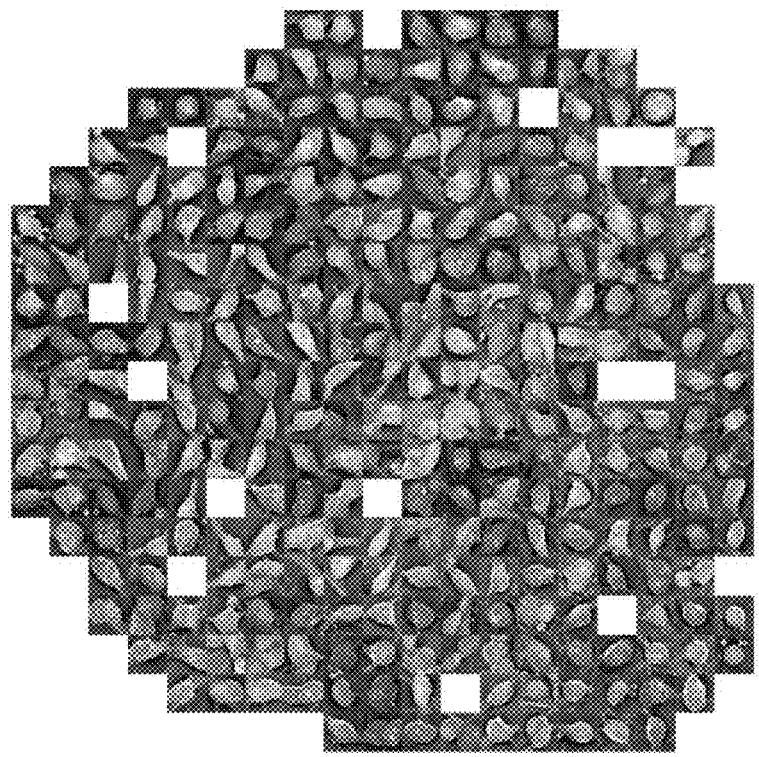
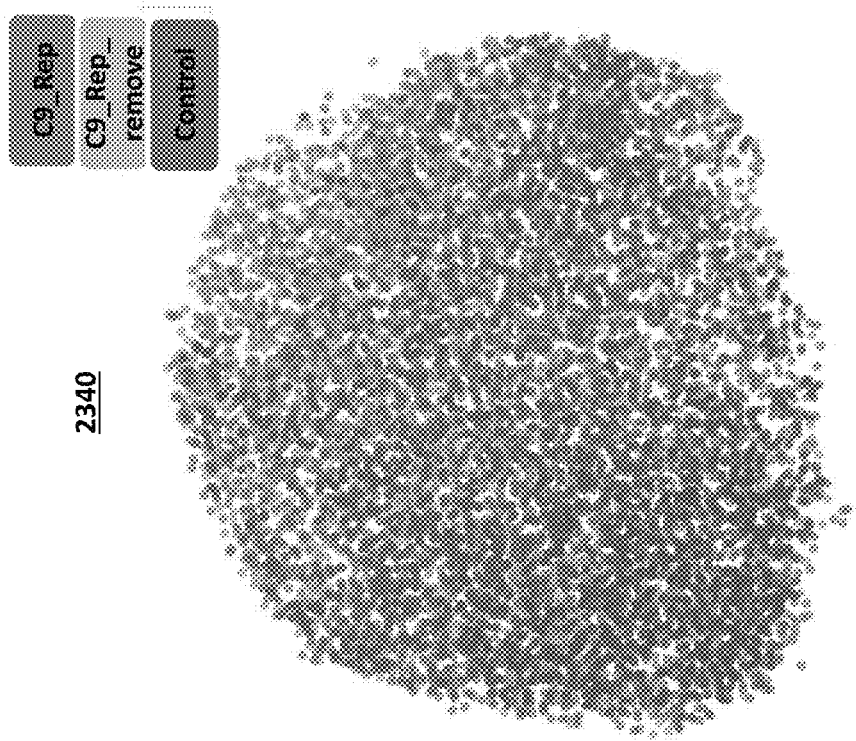
Day 11
FIG. 23E

2550

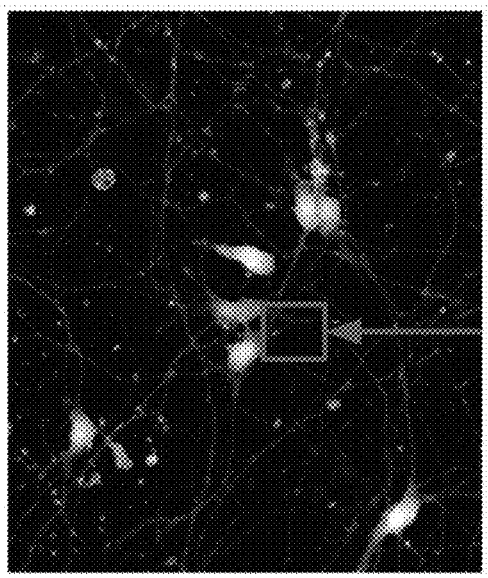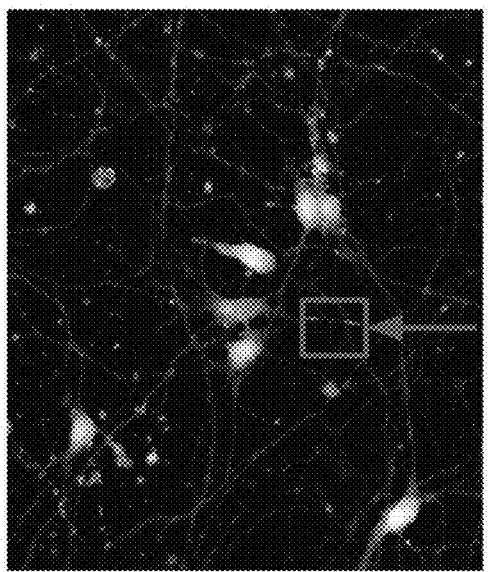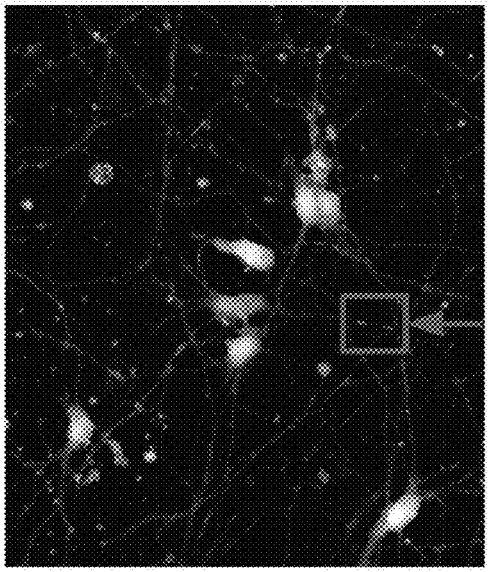
FIG. 26

AUTONOMOUS CELL IMAGING AND MODELING SYSTEM

CROSS-REFERENCE TO RELATED APPLICATIONS

This application is a divisional of U.S. application Ser. No. 18/111,405, filed Feb. 17, 2023, which is a continuation application of International Application No. PCT/US2022/080200, filed internationally on Nov. 19, 2022, which claims priority to U.S. Provisional Patent Application No. 63/281,536, filed Nov. 19, 2021, the contents of each of which is hereby incorporated by reference in its entirety.

FIELD OF INVENTION

The present disclosure relates generally to an autonomous cell imaging and modeling platform, and more specifically to machine-learning techniques for using microscopy imaging data to continuously study live biological cells.

BACKGROUND

The studies of various cell processes, such as cell differentiation, disease modeling, and genetic and chemical screening, are generally laborious, resource-intensive, and time-consuming for a number of reasons. First, continuous monitoring of living systems (e.g., live biological cells) with minimum toxicity is a task that is still not achieved at scale with current technologies. For example, imaging methods for studying cell differentiation (e.g., the process in which a cell changes from one cell type to another) and for screening drug candidates rely heavily on fluorescence biomarkers, which are known to be toxic. As another example, single-cell RNA sequencing (scRNA-seq) techniques rely on the destruction of the cellular material and are therefore end-point assays. Further, while high-throughput imaging screens based on cellular morphology are powerful tools to identify promising drug candidates and targets in drug discovery, the common approaches, such as cell painting, rely on a set of fluorescence dyes to label different cellular components. These approaches involve an assay development that can be laborious and often require sacrificing the cell culture. Further still, imaging datasets are sometimes collected at all stages of a cell culture. However, the heterogeneity of the imaging modalities (e.g., bright-field, wide-field, confocal, super resolution methods) as well as the huge variability in imaging acquisition generate massive biases in the available datasets. As a consequence, the studies of the cell processes are severely slowed down or are reliant on non-destructive imaging modalities that yield poor imaging and limited phenotypic insights.

BRIEF SUMMARY

Disclosed herein are methods, systems, electronic devices, non-transitory storage media, and apparatuses directed to providing an autonomous cell imaging and modeling platform. The autonomous cell imaging and modeling platform can be applied to evaluate various cellular processes, such as cellular differentiation, optimization of cell culture (e.g., in-plate cytometry), disease modeling, histopathology imaging, and genetic and chemical screening, using a dynamic universal imaging system. In some embodiments, the platform comprises a set of label-free, high content computational imaging techniques, self-supervised learning models, and robotic devices configured in an autonomous imaging system to study positional and morphological characteristics in particular cellular substructures of a cell culture in an efficient and non-destructive manner over time.

The autonomous cell imaging and modeling platform provides numerous practical applications related to the studying and control of cellular processes. In some embodiments, the system can continuously generate high-content images of a set of live biological cells in a non-destructive way and analyze the images efficiently using machine-learning techniques (e.g., self-supervised machine-learning models) to evaluate the impact of a therapeutic agent (e.g., a chemical treatment, a genetic treatment) on the cells. In some embodiments, the system can generate high-content images of different sets of live biological cells corresponding to different disease states, convert the high-content images to lower-dimensional embeddings, and generate a disease model in a topological space, which can be used to model the progression of a disease. In some embodiments, the system can continuously generate high-content images of a cell culture in a non-destructive way and analyze the images to study a characteristic of interest of the cell culture such as the cell proliferation rate, reversion to a healthy phenotype, etc. In some embodiments, the system can identify conditions for progressing cells towards a desired cell state in an efficient manner. In some embodiments, the system may comprise optimization steps that may identify combinatorial treatment and drug synergy in chemical and genetic screens.

In some embodiments, the autonomous cell imaging and modeling platform comprises a plurality of stages. In some embodiments, the platform comprises a first autonomous imaging stage. In some embodiments, the first autonomous imaging stage provides label-free imaging (i.e., does not rely on fluorescence dyes to label different cellular components), such as quantitative phase imaging ("QPI"). In some embodiments, QPI can be accomplished using bright-field imaging and other low resource, non-destructive imaging techniques to recreate high content images with sufficient richness and depth for downstream processing. For example, one or more machine-learning models can be configured to transform images of a first modality (e.g., bright-field images) into images of a second modality (e.g., phase images). Accordingly, phase images can be generated at scale and in a low-cost and non-destructive manner. In some embodiments, the machine-learning model is a generative adversarial network model comprising a discriminator and a generator, and can be trained using ground truth images of the first modality and images of the second modality. Additional information of the image transformation models can be found in U.S. application Ser. No. 17/480,047 titled "BIOLOGICAL IMAGE TRANSFORMATION USING MACHINE-LEARNING MODELS," which issued as U.S. Pat. No. 11,423,256 on Aug. 23, 2022, and which is incorporated herein by reference in its entirety. The imaging stage may generate phase images depicting the positional and morphological characteristics in particular cellular substructures. In some embodiments, the imaging stage is compatible with low photo-toxicity fluorescence and autofluorescence multi spectral imaging techniques. The imaging stage may generate fluorescence images and/or autofluorescence images of the live biological cells from transformed bright field images. In some embodiments, the images of live biological cells (e.g., phase images, fluorescence images, autofluorescence images, etc.) are captured at the imaging stage using a microscope according to an optical setup, which can be manually and/or automatically configured.

In some embodiments, the imaging stage is configured to input the fluorescence images and/or autofluorescence images into the machine-learning model configured to transform images of a first modality into images of a second modality (e.g., phase images). In some embodiments, the machine-learning model is a generative adversarial network model comprising a discriminator and a generator, and can be trained using ground truth phase images, fluorescence images, and autofluorescence images.

As described below, the imaging stage provides a number of technical advantages. It provides stability of some core imaging modalities, including the QPI modality and the autofluorescence modality, which guarantee access to morphology and metabolic state, respectively. The imaging stage captures both 2D and 3D phenotypic detail, which results in richer disease progression arcs and richer regression arcs of disease states resulting from cell treatments. It also allows for continuous improvement of the imaging setup for speed and noise minimization. It is also associated with extremely low batch effects, as the state of the system can be adapted in order to guarantee stable image statistics.

The time dependent representations (e.g., continuous images) created by the imaging stage enable the study of biological processes without sample destruction, in contrast with classical analytical methods such as immunostaining or RNA sequencing. Because the imaging stage directly analyzes the state of the live biological cells without destroying the cells, the platform circumvents the need for biomarkers to characterize disease states. As a consequence, not only can genetic and chemical screen efforts start earlier, they can also be performed more rapidly, with minimal effort. The imaging stage captures rich phenotypic data regarding the live biological cells over the desired length of the cell culture, yielding insights regarding cell state progression throughout the culture duration, and not just at the endpoint.

The autonomous cell imaging and modeling platform provided herein can further comprise a second machine-learning-based stage. At the second stage, an exemplary system (e.g., one or more electronic devices) performs machine-learning-based image processing on the high-content images of the live biological cells to obtain cell representations (e.g., embeddings). An embedding is a vector representation of a phenotypic state of the live biological cells. The embedding captures rich semantic information of the imaging data (e.g., features of the microscopic structure of tissues reflected in the image, including cellular substructures), while excluding information that is not relevant to downstream analyses (e.g., orientation of the image).

In some embodiments, the system deploys self-supervised learning (SSL) techniques in which the machine-learning model(s) learn from unlabeled sample data. In some embodiments, the platform can input each image of live biological cells into a trained self-supervised learning model, which is configured to receive an image and output an embedding (i.e., a vector) representing the image in a latent space. The embedding can be a vector representation of the input image in the latent space. Translating an input image into an embedding can significantly reduce the size and dimension of the original data. The lower-dimension embedding can be used for downstream processing, as described herein. In some embodiments, the self-supervised model naturally generates a space-time topological space where directionality is available. For example, each image is transformed into an embedding, which can be mapped into a location in the topological space and time-stamped with the time the image was captured. Accordingly, directionality over space and/or time can be obtained across multiple embeddings.

Embeddings may be generated continuously in the second stage of the platform from the images of the live biological cells. These dynamic embeddings have various advantages. For example, the dynamic embedding may be used for translation tasks (e.g., generating both imaging and sequence information for a sample), for optimizing chemical or genetic treatment dosing strategies for treating disease, for rapidly prioritizing hits from genome wide association studies (GWAS) based on in vitro measurements in later stages of the platform.

In some embodiments, the platform may further comprise a third stage for data analysis. In some embodiments, the embeddings generated in the second stage are used for downstream tasks. In some embodiments, the embeddings can be used to determine the impact of a therapeutic agent (e.g., a chemical treatment, a genetic treatment) in slowing down or reversing the progression of a disease by detecting shifts in cell morphology classification. In some embodiments, the embeddings can be used to generate a disease model (e.g., evaluation of toxicity). In some embodiments, the embeddings can be used to study a characteristic of interest of a cell culture, such as proliferation rate, cell health, cell development, etc., which can be then used to optimize the culture conditions. In some embodiments, the embeddings can be used to identify conditions for progressing cells towards a desired cell state and identify combinatorial treatment and drug synergy in chemical and genetic screens.

The platform may further comprise a fourth stage for optimization and performing automatic tasks. The speed and stability of the platform enables the scalability necessary for the implementation of advanced machine-learning algorithms, such as reinforcement-learning, continuous-learning, and active-learning algorithms. Therefore, the platform may be continuously updated at each stage to optimize the experimental process. In some embodiments, the imaging paradigms are updated to improve the performance of core imaging modalities, such as the QPI modality and the autofluorescence modality, which guarantee access to morphology and metabolic state, respectively. For example, the imaging modalities may be updated by continuously improving speed and noise minimization.

Additional automatic optimizations the platform may perform include updating the genetic and/or chemical perturbations applied to the live biological cells, and updating the biological protocols associated with the live biological cells. In some embodiments, updates to the biological protocols include cell culture condition optimization, cell culture plate optimization (e.g., plate size, plate material, etc.), cell proliferation optimization (e.g., optimization of the timing of culture passaging), and optimization of cell differentiation steps. The platform does not require any complex biochemistry optimization to operate.

Overall, the autonomous cell imaging and modeling platform provides a continuously optimized automatic imaging and modeling setup, which is compatible with the studying and control of various cellular processes. The autonomous, label-free imaging system improves over time and operates in a distributed setup allowing horizontal scaling. Therefore, the platform enables the multi-scale study of dynamic cellular processes at rapid time and spatial frequencies, without destroying the samples. The platform minimizes the need for use or optimization of complex biochemical assays for staining and the identification of biomarkers. It also allows for the propagation of information across independent biochemical experiments, and reduces the need to repeat complex staining procedures.

In some aspects, provided herein is a method of determining an impact of a therapeutic agent on diseased cells, comprising: obtaining a first plurality of images captured at a first plurality of time points of one or more untreated diseased live biological cells expressing a disease phenotype; obtaining a second plurality of images captured at a second plurality of time points of one or more treated diseased live biological cells expressing the disease phenotype that has been treated with the therapeutic agent; inputting the first plurality of images into a trained machine-learning model to obtain a first plurality of embeddings representing positional and morphological changes over time in particular cellular substructures of the one or more untreated diseased live biological cells; inputting the second plurality of images into the trained machine-learning model to obtain a second plurality of embeddings representing positional and morphological changes over time in particular cellular substructures of the one or more treated diseased live biological cells; and determining, from at least a subset of the first plurality of embeddings and the second plurality of embeddings, the impact of the therapeutic agent on the reversion of the one or more treated diseased cells from a diseased state.

In some embodiments, the method further comprises obtaining a third plurality of images captured at a third plurality of time points of one or more healthy live biological cells; inputting the third plurality of images into the trained machine-learning model to obtain a third plurality of embeddings representing positional and morphological changes over time in particular cellular substructures of the one or more healthy live biological cells; and determining, from at least a subset of the first plurality of embeddings, the second plurality of embeddings, and the third plurality of embeddings, the impact of the therapeutic agent on the reversion of the one or more treated cells from the diseased state to the healthy state.

In some embodiments, the one or more treated diseased live biological cells are a first set of treated diseased live biological cells and are treated with a first dosage of the therapeutic agent, the method further comprising: obtaining a fourth plurality of images captured at a fourth plurality of time points of a second set of treated diseased live biological cells expressing the disease phenotype that has been treated with a second dosage of the therapeutic agent; inputting the fourth plurality of images into the trained machine-learning model to obtain a fourth plurality of embeddings representing positional and morphological changes over time in particular cellular substructures of the second set of treated diseased live biological cells; and comparing the impact of the first dosage and the second dosage based on at least a subset of the first plurality of embeddings, the second plurality of embeddings, and the fourth plurality of embeddings.

In some embodiments, the one or more treated diseased live biological cells are a first set of treated diseased live biological cells and wherein the therapeutic agent is a first therapeutic agent, the method further comprising: obtaining a fifth plurality of images captured at a fifth plurality of time points of a third set of treated diseased cells expressing the disease phenotype that has been treated with a second therapeutic agent; inputting the fifth plurality of images into the trained machine-learning model to obtain a fifth plurality of embeddings representing positional and morphological changes over time in particular cellular substructures of the third set of treated diseased live biological cells; and comparing the impact of the first therapeutic agent and the second therapeutic agent based on at least a subset of the first plurality of embeddings, the second plurality of embeddings, and the fifth plurality of embeddings.

In some embodiments, the first plurality of time points are the same as the second plurality of time points.

In some embodiments, the first plurality of time points are different from the second plurality of time points.

In some embodiments, the therapeutic agent is a chemical treatment, a genetic treatment, or any combination thereof.

In some embodiments, the method further comprises: determining one or more dose administration intervals for administering the therapeutic agent based on the second plurality of embeddings.

In some embodiments, the method further comprises: providing a medical recommendation or administering the therapeutic agent to a patient.

In some embodiments, the first plurality of images and the second plurality of images comprise phase images.

In some embodiments, the first plurality of images and the second plurality of images are generated from fluorescence images or autofluorescence images.

In some embodiments, the trained machine-learning model is a self-supervised machine-learning model.

In some embodiments, the trained machine-learning model is trained using unlabeled data.

In some embodiments, the trained machine-learning model is pre-trained using unlabeled images that do not depict biological samples.

In some embodiments, the trained machine-learning model is retrained using unlabeled images of biological samples.

In some embodiments, evaluating the impact of the therapeutic agent comprises: inputting the first plurality of embeddings into a classifier to obtain a first plurality of disease scores; and inputting the second plurality of embeddings into the classifier to obtain a second plurality of disease scores.

In some embodiments, the method further comprises: generating a first time trend based on the first plurality of disease scores; generating a second time trend based on the second plurality of disease scores; and comparing the first time trend and the second time trend.

In some embodiments, the method further comprises: generating a first plurality of distributions based on the first plurality of disease scores; generating a second plurality of distributions based on the second plurality of disease scores; and comparing the first plurality of distributions and the second plurality of distributions.

In some embodiments, the classifier is a logistic regression classifier.

In some aspects, provided herein is a non-transitory computer-readable storage medium storing one or more programs for determining an impact of a therapeutic agent on diseased cells, the one or more programs comprising instructions, which when executed by one or more processors of an electronic device, cause the electronic device to: obtain a first plurality of images captured at a first plurality of time points of one or more untreated diseased live biological cells expressing a disease phenotype; obtain a second plurality of images captured at a second plurality of time points of one or more treated diseased live biological cells expressing the disease phenotype that has been treated with the therapeutic agent; input the first plurality of images into a trained machine-learning model to obtain a first plurality of embeddings representing positional and morphological changes over time in particular cellular substructures of the one or more untreated diseased live biological cells; input the second plurality of images into the trained machine-learning model to obtain a second plurality of embeddings representing positional and morphological changes over time in particular cellular substructures of the one or more treated diseased live biological cells; and determine, from at least a subset of the first plurality of embeddings and the second plurality of embeddings, the impact of the therapeutic agent on the reversion of the one or more treated diseased cells from a diseased state.

In some aspects, provided herein is a system for determining an impact of a therapeutic agent on diseased cells, comprising: one or more processors; a memory; and one or more programs, wherein the one or more programs are stored in the memory and configured to be executed by the one or more processors, the one or more programs including instructions for: obtaining a first plurality of images captured at a first plurality of time points of one or more untreated diseased live biological cells expressing a disease phenotype; obtaining a second plurality of images captured at a second plurality of time points of one or more treated diseased live biological cells expressing the disease phenotype that has been treated with the therapeutic agent; inputting the first plurality of images into a trained machine-learning model to obtain a first plurality of embeddings representing positional and morphological changes over time in particular cellular substructures of the one or more untreated diseased live biological cells; inputting the second plurality of images into the trained machine-learning model to obtain a second plurality of embeddings representing positional and morphological changes over time in particular cellular substructures of the one or more treated diseased live biological cells; and determining, from at least a subset of the first plurality of embeddings and the second plurality of embeddings, the impact of the therapeutic agent on the reversion of the one or more treated diseased cells from a diseased state.

In some aspects, provided herein is a method of modeling a progression of a disease of interest having a plurality of disease states, comprising: obtaining a first set of images captured at a first plurality of time points of a first non-zero concentration of diseased live biological cells expressing a first disease state of the disease; obtaining a second set of images captured at a first plurality of time points of a second non-zero concentration of diseased live biological cells expressing a second disease state of the disease; inputting the first set of images into a trained machine-learning model to obtain a first set of embeddings representing positional and morphological characteristics in particular cellular substructures of the first non-zero concentration of diseased live biological cells; inputting the second set of images into the trained machine-learning model to obtain a second set of embeddings representing positional and morphological characteristics in particular cellular substructures of the second non-zero concentration of diseased live biological cells; generating the disease model based on the first set of embeddings and the second set of embeddings; and modeling a progression of the disease based on the disease model.

In some embodiments, generating a disease model comprises: mapping the first set of embeddings and the second set of embeddings into a topological space.

In some embodiments, the method further comprises: identifying a location of a first cluster of embeddings based on the first set of embeddings in the topological space; generating a representation of the first disease state based on the location of the first cluster; identifying a location of a second cluster of embeddings based on the second set of embeddings in the topological space; and generating a representation of the second disease state based on the location of the second cluster.

In some embodiments, the first set of embeddings and the second set of embeddings are time-stamped in the topological space.

In some embodiments, the method further comprises: applying a therapeutic agent to the first non-zero concentration of diseased live biological cells; obtaining a plurality of images captured at a plurality of time points of the first non-zero concentration of diseased live biological cells; inputting the plurality of images into the trained machine-learning model to obtain a plurality of embeddings representing positional and morphological changes over time in particular cellular substructures of the first non-zero concentration of diseased live biological cells; and determining, from at least a subset of the plurality of embeddings, an impact of the therapeutic agent on the reversion of the first non-zero concentration of diseased live biological cells from a diseased state.

In some embodiments, the therapeutic agent is a chemical treatment, a genetic treatment, or any combination thereof.

In some embodiments, the method further comprises: determining a dosage for the therapeutic agent based on the plurality of embeddings.

In some embodiments, the method further comprises: determining one or more dose administration intervals for administering the therapeutic agent based on the plurality of embeddings.

In some embodiments, the method further comprises: providing a medical recommendation or administering the therapeutic agent to a patient having the disease.

In some embodiments, evaluating the treatment candidate comprises: inputting the plurality of embeddings to a classifier to obtain a plurality of disease scores; and generating a time trend based on the plurality of disease scores.

In some embodiments, evaluating the treatment candidate comprises: inputting the plurality of embeddings to a classifier to obtain a plurality of disease scores; and generating a plurality of distributions based on the plurality of disease scores.

In some embodiments, the classifier is a logistic regression model.

In some embodiments, the first set of images and the second set of images comprise phase images.

In some embodiments, the first set of images and the second set of images are generated based on fluorescence images or autofluorescence images.

In some embodiments, the trained machine-learning model is a self-supervised machine-learning model.

In some embodiments, the trained machine-learning model comprises a neural network.

In some embodiments, the trained machine-learning model is pre-trained using unlabeled images that do not depict biological samples.

In some embodiments, the trained machine-learning model is configured to be retrained using unlabeled images of biological samples.

In some aspects, provided herein is a system for modeling a progression of a disease of interest having a plurality of disease states, comprising: one or more processors; a memory; and one or more programs, wherein the one or more programs are stored in the memory and configured to be executed by the one or more processors, the one or more programs including instructions for: obtaining a first set of images captured at a first plurality of time points of a first non-zero concentration of diseased live biological cells expressing a first disease state of the disease; obtaining a second set of images captured at a first plurality of time points of a second non-zero concentration of diseased live biological cells expressing a second disease state of the disease; inputting the first set of images into a trained machine-learning model to obtain a first set of embeddings representing positional and morphological characteristics in particular cellular substructures of the first non-zero concentration of diseased live biological cells; inputting the second set of images into the trained machine-learning model to obtain a second set of embeddings representing positional and morphological characteristics in particular cellular substructures of the second non-zero concentration of diseased live biological cells; generating the disease model based on the first set of embeddings and the second set of embeddings; and modeling a progression of the disease based on the disease model.

In some aspects, provided herein is a non-transitory computer-readable storage medium storing one or more programs for modeling a progression of a disease of interest having a plurality of disease states, the one or more programs comprising instructions, which when executed by one or more processors of an electronic device having a display, cause the electronic device to perform the operations of: obtaining a first set of images captured at a first plurality of time points of a first non-zero concentration of diseased live biological cells expressing a first disease state of the disease; obtaining a second set of images captured at a first plurality of time points of a second non-zero concentration of diseased live biological cells expressing a second disease state of the disease; inputting the first set of images into a trained machine-learning model to obtain a first set of embeddings representing positional and morphological characteristics in particular cellular substructures of the first non-zero concentration of diseased live biological cells; inputting the second set of images into the trained machine-learning model to obtain a second set of embeddings representing positional and morphological characteristics in particular cellular substructures of the second non-zero concentration of diseased live biological cells; generating the disease model based on the first set of embeddings and the second set of embeddings; and modeling a progression of the disease based on the disease model.

In some aspects, provided herein is a method of modeling a characteristic of interest of a cell culture comprising one or more live biological cells, comprising: obtaining a first set of one or more images capturing the cell culture at a first time point; inputting the first set of one or more images into a trained machine-learning model to obtain a first set of embeddings representing positional and morphological characteristics in particular cellular substructures of the cell culture; evaluating the characteristic of interest of the cell culture corresponding to the first time point based on the first set of embeddings to obtain a first set of one or more values; obtaining a second set of one or more images capturing the cell culture at a second time point; inputting the second set one or more images into the trained machine-learning model to obtain a second set of embeddings representing positional and morphological characteristics in particular cellular substructures of the cell culture; evaluating the characteristic of interest of the cell culture corresponding to the second time point based on the second set of embeddings to obtain a second set of one or more values; and determining, from the first set of one or more values and the second set of one or more values, a change of the characteristic of interest in the cell culture.

In some embodiments, the characteristic of interest is cell proliferation of the cell culture, wherein: i) the first set of one or more values indicates a predicted first proliferation level; ii) the second set of one or more values indicates a predicted second proliferation level; and iii) a rate of proliferation of the cell culture is determined from the predicted first cell proliferation level and the predicted second cell proliferation level.

In some embodiments, the method further comprises: determining the in vitro and/or metabolic fitness of the cell culture based on the predicted first cell proliferation level and the predicted second cell proliferation level.

In some embodiments, the method further comprises: comparing the rate of proliferation to a predefined threshold.

In some embodiments, the method further comprises: if the rate of proliferation exceeds the predefined threshold: determining that the rate of proliferation is an abnormal proliferation rate; and terminating growth of the cell culture before a predefined endpoint of cell growth.

In some embodiments, the method further comprises: predicting the confluence of the cell culture for a third time point after the second time point based on the rate of proliferation of the cell culture.

In some embodiments, the method further comprises: determining timing for passaging of the cell culture based on the predicted confluence of the cell culture.

In some embodiments, the method further comprises: determining timing for passaging of the cell culture based on the rate of proliferation.

In some embodiments, the machine-learning model is a first machine-learning model, and wherein predicting the cell proliferation level comprises: inputting the first set of embeddings into a second machine-learning model to obtain the cell proliferation level corresponding to the first time point; and inputting the second set of embeddings into the second machine-learning model to obtain the cell proliferation level corresponding to the second time point.

In some embodiments, the method further comprises: generating a time trend based on the predicted first cell proliferation level and the predicted second cell proliferation level.

In some embodiments, the second machine-learning model is a linear regression classifier.

In some embodiments, the second machine-learning model is trained using a set of embeddings and a corresponding set of cell proliferation levels.

In some embodiments, the characteristic of interest is health of the cell culture, wherein: i) the first set of one or more values indicates a predicted first cell health level; ii) the second set of one or more values indicates a predicted second cell health level; and iii) a change of the health level of the cell culture is determined from the predicted first cell health level and the predicted second cell health level.

In some embodiments, the characteristic of interest is development of the cell culture, wherein: i) the first set of one or more values indicates a predicted first cell development level; ii) the second set of one or more values indicates a predicted second cell development level; and iii) a change of the development level of the cell culture is determined from the predicted first cell development level and the predicted second cell development level.

In some embodiments, the first set of one or more of images and the second set of one or more images comprise phase images.

In some embodiments, the first set of one or more of images and the second set of one or more images are generated from fluorescence images or autofluorescence images.

In some embodiments, the trained machine-learning model is a self-supervised machine-learning model.

In some embodiments, the trained machine-learning model is trained using unlabeled images of biological samples.

In some embodiments, the one or more live biological cells are mammalian cells.

In some embodiments, the one or more live biological cells are healthy cells.

In some embodiments, the one or more live biological cells are diseased cells.

In some embodiments, the method further comprises, prior to obtaining a first set of one or more images: applying a perturbation and/or a therapeutic agent to the cell culture.

In some embodiments, the perturbation and/or the therapeutic agent is a chemical treatment, a genetic treatment, or any combination thereof.

In some aspects, provided herein is a non-transitory computer-readable storage medium storing one or more programs for modeling a characteristic of interest of a cell culture comprising one or more live biological cells, the one or more programs comprising instructions, which when executed by one or more processors of an electronic device having a display, cause the electronic device to perform the operations of: obtaining a first set of one or more images capturing the cell culture at a first time point; inputting the first set of one or more images into a trained machine-learning model to obtain a first set of embeddings representing positional and morphological characteristics in particular cellular substructures of the cell culture; evaluating the characteristic of interest of the cell culture corresponding to the first time point based on the first set of embeddings to obtain a first set of one or more values; obtaining a second set of one or more images capturing the cell culture at a second time point; inputting the second set one or more images into the trained machine-learning model to obtain a second set of embeddings representing positional and morphological characteristics in particular cellular substructures of the cell culture; evaluating the characteristic of interest of the cell culture corresponding to the second time point based on the second set of embeddings to obtain a second set of one or more values; and determining, from the first set of one or more values and the second set of one or more values, a change of the characteristic of interest in the cell culture.

In some aspects, provided herein is a system for modeling a characteristic of interest of a cell culture comprising one or more live biological cells, comprising: one or more processors; a memory; and one or more programs, wherein the one or more programs are stored in the memory and configured to be executed by the one or more processors, the one or more programs including instructions for: obtaining a first set of one or more images capturing the cell culture at a first time point; inputting the first set of one or more images into a trained machine-learning model to obtain a first set of embeddings representing positional and morphological characteristics in particular cellular substructures of the cell culture; evaluating the characteristic of interest of the cell culture corresponding to the first time point based on the first set of embeddings to obtain a first set of one or more values; obtaining a second set of one or more images capturing the cell culture at a second time point; inputting the second set one or more images into the trained machine-learning model to obtain a second set of embeddings representing positional and morphological characteristics in particular cellular substructures of the cell culture; evaluating the characteristic of interest of the cell culture corresponding to the second time point based on the second set of embeddings to obtain a second set of one or more values; and determining, from the first set of one or more values and the second set of one or more values, a change of the characteristic of interest in the cell culture.

In some aspects, provided herein is a method for identifying one or more cell culture conditions for progressing one or more live biological cells towards a desired cell state, comprising: performing a plurality of cell culture condition identification cycles on the one or more live biological cells until a condition is met, wherein each cell culture condition identification cycle comprises: obtaining a set of one or more images capturing the one or more live biological cells; determining, from at least a subset of the set of images, a cell state of the one or more live biological cells; identifying a new cell culture condition for progressing the one or more live biological cells towards the desired cell state, by inputting the current cell state and the desired cell state into a trained machine-learning model; and applying the new cell culture condition to the one or more live biological cells; and identifying the one or more cell culture conditions, based on the outcomes of the plurality of cell culture condition identification cycles, for use in progressing live biological cells towards the desired cell state in future cell cultures.

In some embodiments, the one or more live biological cells are a first set of one or more live biological cells that are deposited in a first well, and the plurality of cell culture condition identification cycles is a first plurality of cell culture condition identification cycles, the method further comprising: depositing a second set of one or more live biological cells in a second well; performing a second plurality of cell culture condition identification cycles on the second set of one or more live biological cells, wherein the second plurality of cell culture condition identification cycles is different from the first plurality of cell culture condition identification cycles; and prioritizing one or more cell culture conditions in the first plurality of cell culture condition identification cycles and the second plurality of cell culture condition identification cycles based on the outcomes of the first plurality of cell culture condition identification cycles and the second plurality of cell culture condition identification cycles.

In some embodiments, the time frame for performing the first plurality of cell culture condition identification cycles overlaps with the time frame for performing the second plurality of cell culture condition identification cycles.

In some embodiments, the first well and the second well belong to the same multi-well plate.

In some embodiments, the differences between the first plurality of cell culture condition identification cycles and the second plurality of cell culture condition identification cycles comprise cell culture medium ingredient differences, cell culture temperature differences, cell culture pressure exposure differences, and/or cell culture medium light exposure differences.

In some embodiments, the condition is met when the desired cell state is achieved.

In some embodiments, the condition is met when a predefined number of cell culture condition identification cycles are performed.

In some embodiments, the trained machine-learning model is an active-learning machine-learning model.

In some embodiments, each cell culture condition identification cycle further comprises: prompting the user to provide one or more user inputs about the state of the one or more live biological cells after the new cell culture condition is applied; and retraining the active-learning machine-learning model based on the user inputs.

In some embodiments, the user is an individual.

In some embodiments, the trained machine-learning model is a reinforcement-learning machine-learning model.

In some embodiments, each cell culture condition identification cycle further comprises: determining the cell state of the one or more live biological cells after the new cell culture condition applied; and retraining the reinforcement-learning machine-learning model based on the determined cell state.

In some embodiments, the set of one or more images comprise phase images.

In some embodiments, the set of one or more images are generated based on fluorescence images or autofluorescence images.

In some embodiments, the one or more live biological cells are induced pluripotent stem cells.

In some embodiments, the desired cell state is a non-pluripotent cell state.

In some embodiments, the one or more live biological cells are healthy cells.

In some embodiments, the desired cell state is a diseased cell state.

In some embodiments, the new cell culture condition is a perturbagen.

In some embodiments, the perturbagen is a chemical treatment, a genetic treatment, or any combination thereof.

In some embodiments, the new cell culture condition is a therapeutic agent.

In some embodiments, the therapeutic agent is a chemical treatment, a genetic treatment, or any combination thereof.

In some embodiments, the new cell culture condition is a temperature, pressure, and/or light exposure.

In some embodiments, the applying the new type of cell culture condition to the one or more live biological cells is automated by one or more electronic devices.

In some embodiments, the one or more live biological cells are mammalian cells.

In some aspects, provided herein is a non-transitory computer-readable storage medium storing one or more programs for identifying one or more cell culture conditions for progressing one or more live biological cells towards a desired cell state, the one or more programs comprising instructions, which when executed by one or more processors of an electronic device having a display, cause the electronic device to perform the operations of: performing a plurality of cell culture condition identification cycles on the one or more live biological cells until a condition is met, wherein each cell culture condition identification cycle comprises: obtaining a set of one or more images capturing the one or more live biological cells; determining, from at least a subset of the set of images, a cell state of the one or more live biological cells; identifying a new cell culture condition for progressing the one or more live biological cells towards the desired cell state, by inputting the current cell state and the desired cell state into a trained machine-learning model; and applying the new cell culture condition to the one or more live biological cells; and identifying the one or more cell culture conditions, based on the outcomes of the plurality of cell culture condition identification cycles, for use in progressing live biological cells towards the desired cell state in future cell cultures.

In some aspects, provided herein is a system for determining an impact of a therapeutic agent on diseased cells, comprising: one or more processors; a memory; and one or more programs, wherein the one or more programs are stored in the memory and configured to be executed by the one or more processors, the one or more programs including instructions for: performing a plurality of cell culture condition identification cycles on the one or more live biological cells until a condition is met, wherein each cell culture condition identification cycle comprises: obtaining a set of one or more images capturing the one or more live biological cells; determining, from at least a subset of the set of images, a cell state of the one or more live biological cells; identifying a new cell culture condition for progressing the one or more live biological cells towards the desired cell state, by inputting the current cell state and the desired cell state into a trained machine-learning model; and applying the new cell culture condition to the one or more live biological cells; and identifying the one or more cell culture conditions, based on the outcomes of the plurality of cell culture condition identification cycles, for use in progressing live biological cells towards the desired cell state in future cell cultures.

DESCRIPTION OF THE FIGURES

Various aspects of the disclosure are set forth with particularity in the appended claims. The file of this patent contains at least one drawing/photograph executed in color. Copies of this patent with color drawing(s)/photograph(s) will be provided by the Office upon request and payment of the necessary fee, A better understanding of the features and advantages of the present disclosure will be obtained by reference to the following detailed description that sets forth illustrative embodiments, in which the principles of the disclosure are utilized, and the accompanying drawings of which:

FIG. 17A illustrates an exemplary method for training the machine-learning model of FIG. 15, in accordance with some embodiments FIG. 17B illustrates an exemplary method for continuously updating the machine-learning model of FIG. 15, in accordance with some embodiments.

FIG. 18 illustrates an exemplary electronic device, in accordance with some embodiments.

FIGS. 20A-20D illustrate visualizations of embeddings derived from images of neurological cells and phase images of the neurological cells, in accordance with some embodiments.

FIG. 22 illustrate phase images and filtered images of healthy neurological cells and diseased neurological cells, in accordance with some embodiments.

FIGS. 23A-23E illustrate visualizations of embeddings derived from phase images and the phase images of neurological cells after different amounts of differentiation have been performed, in accordance with some embodiments.

FIG. 26 illustrates images extracted from a video depicting the movement of objects within neurological cells, in accordance with some embodiments.

DETAILED DESCRIPTION

Figure 1:
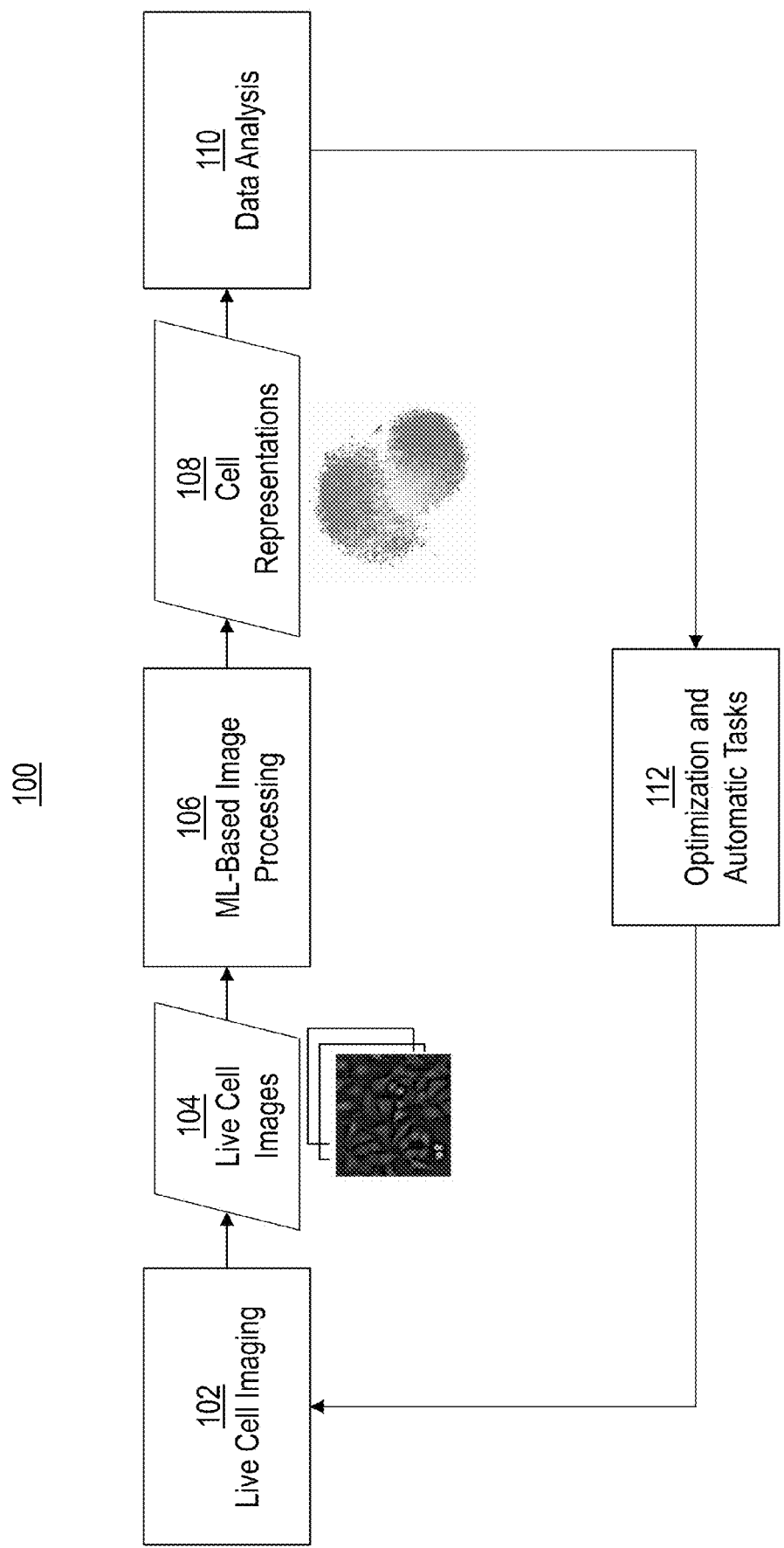
FIG. 1 illustrates an exemplary autonomous cell imaging and modeling system, in accordance with some embodiments.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Disclosed herein are methods, systems, electronic devices, non-transitory storage media, and apparatuses directed to providing an autonomous cell imaging and modeling platform. The autonomous cell imaging and modeling platform can be applied to evaluate various cellular processes, such as cellular differentiation, optimization of cell culture (e.g., in-plate cytometry), disease modeling, histopathology imaging, and genetic and chemical screening, using a dynamic universal imaging system. In some embodiments, the platform comprises a set of label-free computational imaging techniques, self-supervised learning models, and robotic devices configured in an autonomous imaging system to study positional and morphological characteristics in particular cellular substructures of a cell culture in an efficient and non-destructive manner over time.

The autonomous cell imaging and modeling platform provides numerous practical applications related to the studying and control of cellular processes. In some embodiments, the system can continuously generate high-content images of a set of live biological cells in a non-destructive way and analyze the images efficiently using machine-learning techniques (e.g., self-supervised machine-learning models) to evaluate the impact of a therapeutic agent (e.g., a chemical treatment, a genetic treatment). In some embodiments, the system can generate high-content images of different sets of live biological cells corresponding to different disease states, convert the high-content images to lower-dimensional embeddings, and generate a disease model in a topological space, which can be used to model the progression of a disease. In some embodiments, the system can continuously generate high-content images of a cell culture in a non-destructive way and analyze the images to study a characteristic of interest of the cell culture such as the cell proliferation rate, cell health, etc. In some embodiments, the system can identify conditions for progressing cells towards a desired cell state in an efficient manner. In some embodiments, the system may comprise optimization steps that may identify combinatorial treatment and drug synergy in chemical and genetic screens.

In some embodiments, the autonomous cell imaging and modeling platform comprises a plurality of stages. In some embodiments, the platform comprises a first autonomous imaging stage. In some embodiments, the imaging stage provides label-free imaging (i.e., does not rely on fluorescence dyes to label different cellular components), such as quantitative phase imaging ("QPI"). In some embodiments, QPI can be accomplished using bright-field and other low resource, non-destructive imaging techniques to recreate high content images with sufficient richness and depth for downstream processing. For example, one or more machine-learning models can be configured to transform images of a first modality (e.g., bright-field images) into images of a second modality (e.g., phase images). Accordingly, phase images can be generated at scale and in a low-cost and non-destructive manner. In some embodiments, the machine-learning model is a generative adversarial network model comprising a discriminator and a generator, and can be trained using ground truth images of the first modality and images of the second modality. Additional information of the image transformation models can be found in U.S. application Ser. No. 17/480,047 titled "BIOLOGICAL IMAGE TRANSFORMATION USING MACHINE-LEARNING MODELS," which issued as U.S. Pat. No. 11,423,256 on Aug. 23, 2022, and which is incorporated herein by reference in its entirety. The imaging stage may generate phase images depicting the positional and morphological characteristics in particular cellular substructures. In some embodiments, the imaging stage is compatible with low photo-toxicity fluorescence and autofluorescence multi spectral imaging techniques. The imaging stage may generate fluorescence images and/or autofluorescence images of the live biological cells. In some embodiments, the images of live biological cells (e.g., phase images, fluorescence images, autofluorescence images, etc.) are captured at the imaging stage using a microscope according to an optical setup, which can be manually and/or automatically configured.

In some embodiments, the imaging stage is configured to input the fluorescence images and/or autofluorescence images into the machine-learning model configured to transform images of a first modality into images of a second modality (e.g., phase images). In some embodiments, the machine-learning model is a generative adversarial network model comprising a discriminator and a generator, and can be trained using ground truth phase images, fluorescence images, and autofluorescence images.

As described below, the imaging stage provides a number of technical advantages. It provides stability of some core imaging modalities, including the QPI modality and the autofluorescence modality, which guarantee access to morphology and metabolic state, respectively. The imaging stage captures both 2D and 3D phenotypic detail, which results in richer disease progression arcs and richer regression arcs of disease states resulting from cell treatments. It also allows for continuous improvement of the imaging setup for speed and noise minimization. The imaging stage is also associated with extremely low batch effects, as the state of the system can be adapted in order to guarantee stable image statistics.

The time dependent representations (e.g., continuous images) created by the imaging stage enable the study of biological processes without sample destruction, in contrast with classical analytical methods such as immunostaining or RNA sequencing. Because the imaging stage directly analyzes the state of the live biological cells without destroying the cells, the platform circumvents the need for biomarkers to characterize disease states. As a consequence, not only can genetic and chemical screen efforts start earlier, they can also be performed more rapidly, with minimal effort.

The autonomous cell imaging and modeling platform provided herein can comprise a second machine-learning-based stage. At the second stage, an exemplary system (e.g., one or more electronic devices) performs machine-learning-based image processing on the high-content images of the live biological cells to obtain cell representations (e.g., embeddings). An embedding is a vector representation of a phenotypic state of the live biological cells. The embedding captures rich semantic information of the imaging data (e.g., features of the microscopic structure of tissues reflected in the image), while excluding information that is not relevant to downstream analyses (e.g., orientation of the image).

In some embodiments, the system deploys self-supervised learning (SSL) techniques in which the machine-learning model(s) learn from unlabeled sample data. In some embodiments, the platform can input each image of live biological cells into a trained self-supervised learning model, which is configured to receive an image and output an embedding (i.e., a vector) representing the image in a latent space. The embedding can be a vector representation of the input image in the latent space. Translating an input image into an embedding can significantly reduce the size and dimension of the original data. The lower-dimension embedding can be used for downstream processing, as described herein. In some embodiments, the self-supervised model naturally generates a space-time topological space where directionality is available. For example, each image is transformed into an embedding, which can be mapped into a location in the topological space and time-stamped with the time the image was captured. Accordingly, directionality over space and/or time can be obtained across multiple embeddings.

Embeddings may be generated continuously in the second stage of the platform from the images of the live biological cells. These dynamic embeddings have various advantages. For example, the dynamic embedding may be used for translation tasks (e.g., generating both imaging and sequence information for a sample), for optimizing chemical or genetic treatment dosing strategies for treating disease, for rapidly prioritizing hits from genome wide association studies (GWAS) based on in vitro measurements in later stages of the platform.

In some embodiments, the platform comprises a third stage for data analysis. In some embodiments, the embeddings generated in the second stage are used for downstream tasks. In some embodiments, the embeddings can be used to determine the impact of a therapeutic agent (e.g., a chemical treatment, a genetic treatment) in slowing down or reversing the progression of a disease by detecting shifts in cell morphology classification. In some embodiments, the embeddings can be used to generate a disease model (e.g., evaluation of toxicity). In some embodiments, the embeddings can be used to study a characteristic of interest of a cell culture, such as proliferation rate, cell health, cell development, etc., which can be then used to optimize the culture conditions. In some embodiments, the embeddings can be used to identify conditions for progressing cells towards a desired cell state and identify combinatorial treatment and drug synergy in chemical and genetic screens.

The platform may comprise a fourth stage for optimization and performing automatic tasks. The speed and stability of the platform enables the scalability necessary for the implementation of advanced machine-learning algorithms, such as reinforcement-learning, continuous-learning, and active-learning algorithms. Therefore, the platform may be continuously updated at each stage to optimize the experimental process. In some embodiments, the imaging paradigms are updated to improve the performance of core imaging modalities, such as the QPI modality and the autofluorescence modality, which guarantee access to morphology and metabolic state, respectively. For example, the imaging modalities may be updated by continuously improving speed and noise minimization.

Additional automatic optimizations the platform may perform include updating the genetic and/or chemical perturbations applied to the live biological cells, and updating the biological protocols associated with the live biological cells. In some embodiments, updates to the biological protocols include cell culture condition optimization, such as cell culture medium optimization (e.g., optimization of cell culture medium ingredients and concentrations of ingredients), cell culture plate optimization (e.g., plate size, plate material, etc.), cell proliferation optimization (e.g., optimization of the timing of culture passaging), pressure, light, and heat exposure of the cells during culturing, and optimization of cell differentiation steps. The platform does not require any complex biochemistry optimization to operate.

Overall, the autonomous cell imaging and modeling platform provides a continuously optimized automatic imaging and modeling setup, which is compatible with the studying and control of various cellular processes. The autonomous, label-free imaging system improves over time and operates in a distributed setup allowing horizontal scaling. Therefore, the platform enables the multi-scale study of dynamic cellular processes at rapid time and spatial frequencies, without destroying the samples. The platform minimizes the optimization of complex biochemical assays for staining and the identification of biomarkers. It also allows for the propagation of information across independent biochemical experiments, and reduces the need to repeat complex staining procedures.

The following description sets forth exemplary methods, parameters, and the like. It should be recognized, however, that such description is not intended as a limitation on the scope of the present disclosure but is instead provided as a description of exemplary embodiments.

Although the following description uses terms "first," "second," etc. to describe various elements, these elements should not be limited by the terms. These terms are only used to distinguish one element from another. For example, a first graphical representation could be termed a second graphical representation, and, similarly, a second graphical representation could be termed a first graphical representation, without departing from the scope of the various described embodiments. The first graphical representation and the second graphical representation are both graphical representations, but they are not the same graphical representation.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

FIG. 1 illustrates an exemplary autonomous cell imaging and modeling system, in accordance with some embodiments. Process 100 is performed, for example, at least partially using one or more electronic devices. While portions of process 100 are described herein as being performed by particular devices, it will be appreciated that process 100 is not so limited. In process 100, some blocks are, optionally, combined, the order of some blocks is, optionally, changed, and some blocks are, optionally, omitted. In some examples, additional steps may be performed in combination with the process 100. Accordingly, the operations as illustrated (and described in greater detail below) are exemplary by nature and, as such, should not be viewed as limiting.

At block 102, the system obtains high content images 104 of live biological cells (e.g., in vitro cell cultures) using techniques that do not destroy the imaged live biological cells. As described in detail below, the imaging paradigm in block 102 provides a number of technical advantages. It provides stability of some core imaging modalities, including the QPI modality and the autofluorescence modality, which guarantee access to morphology and metabolic state, respectively. It allows for continuous improvement of the imaging setup for speed and noise minimization. It is also associated with extremely low batch effects, as the state of the system can be adapted in order to guarantee stable image statistics.

The live biological cells may be mammalian cells. In some embodiments, the cells are healthy cells. In some embodiments, the healthy cells have not been previously treated (e.g., with a genetic perturbagen or a therapeutic agent). In some embodiments, the healthy cells have been previously treated with either a genetic perturbagen or a therapeutic agent, which may be determined in previous iteration(s) of the workflow as described herein. In some embodiments, the cells are diseased cells. For example, the diseased cells may be a disease model of steatohepatitis, nonalcoholic steatohepatitis (NASH), or amyotrophic lateral sclerosis (ALS). In some embodiments, the diseased cells have not been previously treated (e.g., with a genetic perturbagen or a therapeutic agent). In some embodiments, the diseased cells have been previously treated with either a genetic perturbagen or a therapeutic agent, which may be determined in previous iteration(s) of the workflow as described herein. In some embodiments, the diseased cells have been previously treated with both a genetic perturbagen and a therapeutic agent. In some embodiments, the genetic perturbagen is a chemical treatment, a genetic treatment, or any combination thereof. In some embodiments, the therapeutic agent is a chemical treatment, a genetic treatment, or any combination thereof. Images can be captured of the same live biological cells at any desired time interval, such as once per millisecond, once per second, once per minute, once per hour, once per day, once per week, etc.

In some embodiments, the system performs label-free imaging. In other words, the system performs imaging of the live biological cells without relying on fluorescence dyes to label different cellular components. In some embodiments, the system performs quantitative phase imaging ("QPI") to obtain phase images depicting the positional and morphological characteristics in particular cellular substructures. Because different components in cells shift differently based on the phase of light traveling through them, capturing these shifts through QPI allows sub-micron resolution observations. QPI provided by coherence controlled holographic microscopy produces images with enhanced information compared to ordinary light contrast microscopy and, due to inherent coherence gate effects, enables observation of live cells' activity even in scattering milieu such as a 3D collagen matrix. Further, QPI enables the observation of cells with minimum photo-toxicity. Thus, QPI can be used to speed up in vitro assay development and can provide unique insights on the dynamics of live biological processes. In some embodiments, QPI can be accomplished using bright-field and other low resource, non-destructive imaging techniques to recreate high content images with sufficient richness and depth for downstream processing. For example, one or more machine-learning models can be configured to transform images of a first modality (e.g., bright-field images) into images of a second modality (e.g., phase images). Accordingly, phase images can be generated at scale and in a low-cost and non-destructive manner. In some embodiments, the machine-learning model is a generative adversarial network model comprising a discriminator and a generator, and can be trained using ground truth images of the first modality and images of the second modality. Additional information of the image transformation models can be found in U.S. application Ser. No. 17/480,047 titled "BIOLOGICAL IMAGE TRANSFORMATION USING MACHINE-LEARNING MODELS," which issued as U.S. Pat. No. 11,423,256 on Aug. 23, 2022, and which is incorporated herein by reference in its entirety.

In some embodiments, the system uses low photo-toxicity fluorescence and autofluorescence multi spectral imaging techniques to obtain fluorescence images and/or autofluorescence images of the live biological cells. In some embodiments, the system can input the fluorescence images and/or autofluorescence images into a machine-learning model configured to transform images of a first modality into images of a second modality (e.g., phase images). In some embodiments, the machine-learning model is a generative adversarial network model comprising a discriminator and a generator, and can be trained using ground truth phase images, fluorescence images, and autofluorescence images. In some embodiments, the images of live biological cells (e.g., phase images, fluorescence images, autofluorescence images, etc.) are captured using a microscope according to an optical setup. The optical setup can include an illumination pattern for illuminating the live biological cells. In some embodiments, the illumination pattern can be determined dynamically during the process 100. Additional information of the image transformation model and the identification of the optical setup can be found in U.S. application Ser. No. 17/480,047 titled "BIOLOGICAL IMAGE TRANSFORMATION USING MACHINE-LEARNING MODELS," which issued as U.S. Pat. No. 11,423,256 on Aug. 23, 2022, and which is incorporated herein by reference in its entirety.

In some embodiments, the system uses various phase imaging optical techniques (e.g., quantitative phase contrast (QPC), Quadriwave lateral shearing interferometry, spatial light modulator or SLM) to purposefully induce aberrations and retrieve ground truth quantitative phase information. In some embodiments, the system uses a set of commercially available live cell compatible dyes (or reporter lines) for fast determination of cell stress (e.g., apoptosis, necrosis, position in cell cycle, mitochondrial and ER stress, etc.)

At block 106, the system performs machine-learning-based image processing on the high content images 104 of the live biological cells to obtain cell representations 108. In some embodiments, the system deploys self-supervised learning (SSL) techniques in which the machine-learning model(s) learn from unlabeled sample data, as described in detail herein. For example, the system can input each image of live biological cells into a trained self-supervised learning model, which is configured to receive an image and output an embedding (i.e., a vectors) representing the image in a latent space. The embedding can be a vector representation of the input image in the latent space. Translating an input image into an embedding can significantly reduce the size and dimension of the original data. The lower-dimension embeddings can be used for downstream processing, as described herein.

By obtaining embeddings 108 from the images 104, the self-supervised model can generate a space-time topological space where directionality is available. For example, each image is transformed into an embedding, which can be mapped into a location in the topological space and time-stamped with the time the image was captured. Accordingly, directionality over space and/or time can be obtained across multiple embeddings in the topological space.

In some embodiments, the self-supervised learning model is a DINO Vision Transformer, a SimCLR model, or any other model that learns from unlabeled sample data. In some embodiments, the unsupervised machine-learning model is a trained contrastive learning algorithm. Contrastive learning can refer to a machine learning technique used to learn the general features of a dataset without labels by teaching the model which data points are similar or different. Contrastive learning models can extract embeddings from imaging data that are linearly predictive of labels that might otherwise be assigned to such data. A suitable contrastive learning model is trained by minimizing a contrastive loss, which maximizes the similarity between embeddings from different augmentations of the same sample image and minimizes the similarity between embeddings of different sample images. For example, the model can extract embeddings from images that are invariant to rotation, flipping, cropping and color jittering.

Before the self-supervised model is used to process input images (e.g., images 104), it needs to be trained. In some embodiments, the trained self-supervised learning model is pre-trained using unlabeled images that do not depict biological samples. In some embodiments, the model is retrained or fine-tuned using unlabeled images of biological samples, such as phase images. In some embodiments, the model is continuously updated on all imaging experiments to gather information about all existing cell types, perturbations and imaging conditions.

Figure 2:
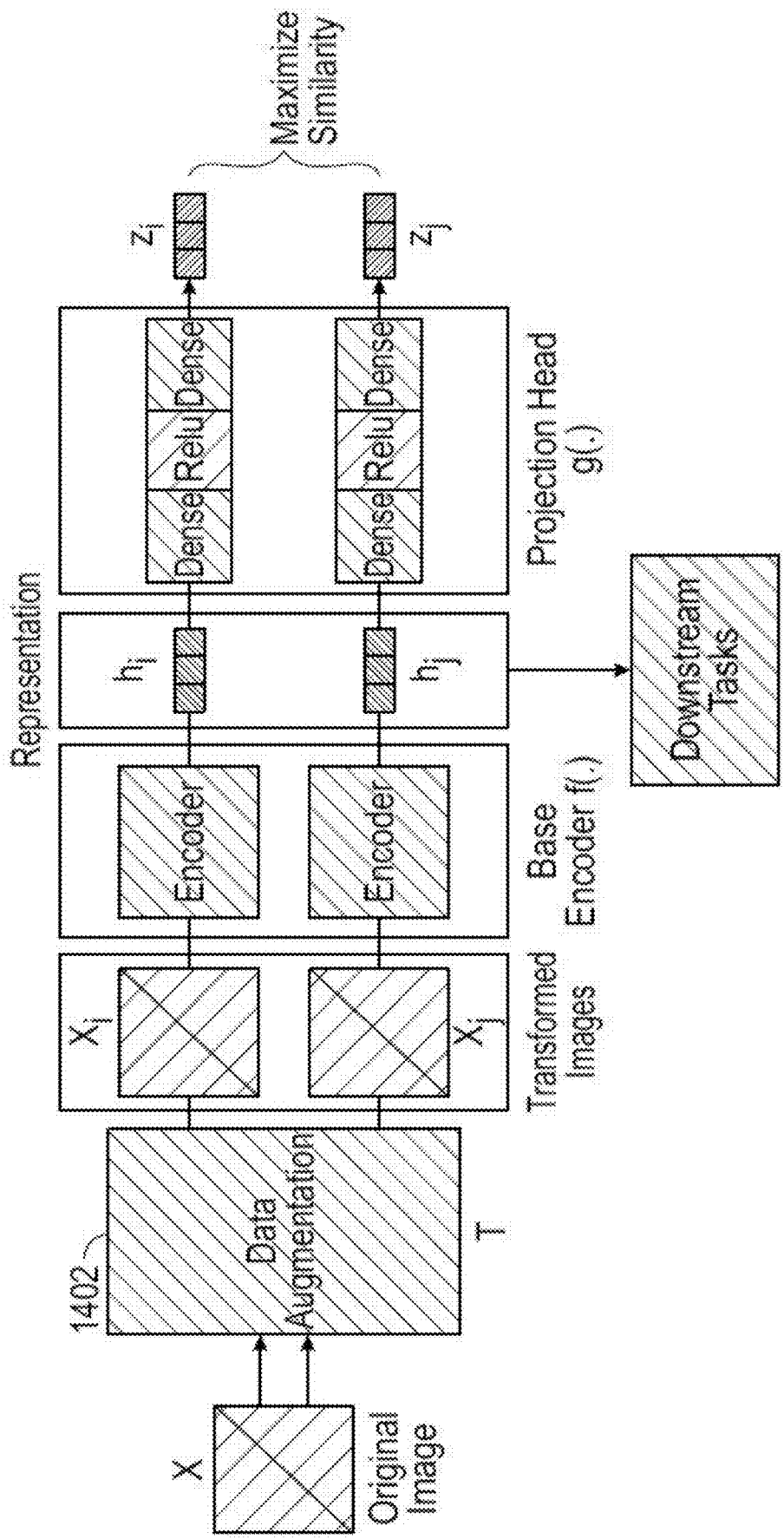
FIG. 2 illustrates training of an exemplary contrastive learning algorithm, in accordance with some embodiments.

FIG. 2 illustrates training of an exemplary contrastive learning algorithm, in accordance with some embodiments. The model used in FIG. 1 can be one of the encoders in FIG. 2. During training, an original image X is obtained. Data transformation or augmentation can be applied to the original image X to obtain two augmented images $X_i$ and $X_j$. For example, the system can randomly apply two separate data augmentation operators (e.g., crop, flip, color jitter, grayscale, blur) to obtain $X_i$ and $X_j$.

Each of the two augmented images $X_i$ and $X_j$ is passed through an encoder to obtain respective vector representations in a latent space. In the depicted example, the two encoders have shared weights. In some examples, each encoder is implemented as a neural network. For example, an encoder can be implemented using a variant of the residual neural network ("ResNet") architecture. As shown, the two encoders output $h_i$ (vector outputted by the encoder from $X_i$) and $h_j$ (vector outputted by the encoder from $X_j$).

The two vector representations $h_i$ and $h_j$ are passed through a projection head to obtain two projections $z_i$ and $z_j$. In some examples, the projection head comprises a series of non-linear layers (e.g., Dense—Relu—Dense layers) to apply non-linear transformation on the vector representation to obtain the projection. The projection head amplifies the invariant features and maximizes the ability of the network to identify different transformations of the same image.

During training, the similarity between the two projections $z_i$ and $z_j$ for the same image is maximized. For example, a loss is calculated based on $z_i$ and $z_j$, and the encoder is updated based on the loss to maximize a similarity between the two latent representations. In some examples, to maximize agreement (i.e., similarity) between the z-projections, the system can define the similarity metric as cosine similarity:

$$sim(u, v) = \frac{u^T v}{\|u\|\|v\|}$$

In some examples, the system trains the network by minimizing the normalized temperature-scaled cross-entropy loss:

$$\ell_{i,j} = -\log \frac{\exp(sim(z_i, z_j)/\tau)}{\sum_{k=1}^{2N} \mathbb{1}_{[k \neq i]} \exp(sim(z_i, z_k)/\tau)}$$

where $\tau$ denotes an adjustable temperature parameter. Accordingly, via training, the encoder learns to output a vector representation that preserves the invariant features of the input image while minimizing image-specific characteristics (e.g., imaging angle, resolution, artifacts).

In some embodiments, the self-supervised model can be trained using non-microscopy images and then used to process live cell images in block 106 in FIG. 1. In some embodiments, the model is first trained using non-microscopy images, then fine-tuned (e.g., retrained) using live cell images for a number of epochs, and then used to process input live cell images in block 106 in FIG. 1. In some embodiments, the live cell images used to fine-tune the model can be selected from the images 104 in FIG. 1. In other words, the live cell images may be first used to train the model, and then inputted into the trained model to obtain embeddings.

In some embodiments, the self-supervised machine-learning model is configured to support various physical and biological constraints. In some embodiments, the model can be configured to support local stationarity of the embedding representations. In some embodiments, the model can be configured to be compatible with time sub-sampling. For example, the system can derive an embedding for $t_1$ based on an embedding of an image at to and an embedding of an image at $t_2$, for example, by using interpolation. In some embodiments, the model can be configured to be compatible with various physics models such as energy-based models for fluid dynamics. In some embodiments, the model uses an attention mechanism to track image subparts, such as cellular substructures.

In some embodiments, at block 106, the system performs segmentation on the live cell images, (e.g., cell detection, nucleus detection). In some embodiments, the system performs quality control on the live cell images to obtain quality control measures, which can be used to remove artifacts, determine which live cell images are used for downstream processing in 110, etc.

At block 110, the system performs data analysis. In some embodiments, the embeddings can be used to determine the impact of a therapeutic agent (e.g., a chemical treatment, a genetic treatment) in slowing down or reversing the progression of a disease by detecting shifts in cell morphology classification. In some embodiments, the embeddings can be used to generate a disease model (e.g., evaluation of toxicity). In some embodiments, the embeddings can be used to study a characteristic of interest of a cell culture, such as proliferation rate, cell health, cell development, etc., which can be then used to optimize the culture conditions, either in real time for the cell culture under study from which the embeddings were generated or in subsequent cell cultures. In some embodiments, the embeddings can be used to identify conditions for progressing cells towards a desired cell state and identify combinatorial treatment and drug synergy in chemical and genetic screens.

At block 112, the system performs optimization and automatic tasks. Automation of the system allows for monitoring of the live biological cells by continuous imaging using any of the imaging techniques described herein. In some embodiments, the system comprises one or more electronic devices (e.g., robotic devices) that automatically apply, for example, therapeutic agents and/or perturbagens to the live biological cells across multiple cycles.

The system may automatically optimize each step of the process illustrated in FIG. 1. In some embodiments, the imaging paradigm in block 102 is updated to improve the performance of core imaging modalities, such as the QPI modality and the autofluorescence modality, which enhance access to morphology and metabolic state, respectively. The imaging setup benefits from local improvement as the acquisition parameters are shared across the imaging paradigm. For example, the system may optimize the imaging modalities by continuously improving speed and noise minimization. Furthermore, the state of the system can be adapted in order to guarantee stable image statistics. In some embodiments, the images of live biological cells (e.g., bright-field images, phase images, fluorescence images, autofluorescence images, etc.) are captured using a microscope according to an optical setup that can be dynamically optimized. The optical setup can include an illumination pattern for illuminating the live biological cells. In some embodiments, an illumination pattern can indicate whether each illumination emitter of an illumination source (e.g., each LED on a LED array) is to be turned on or off and the intensity of each illumination emitter. In some embodiments, the illumination pattern can be determined dynamically based on one or more machine-learning models. For example, a machine-learning model can be configured to generate phase images based on images of other modalities (e.g., bright-field images). The model can include an attention layer comprising a plurality of weights corresponding to the intensities of a plurality of illumination emitters (e.g., a plurality of weights corresponding to the intensities of a plurality of LEDs on the LED array). While the model is trained and/or used, the system can determine an optimal illumination pattern based on the performance of the model under varying illumination patterns. Additional information of the image transformation model and the identification of the optical setup can be found in U.S. application Ser. No. 17/480,047 titled "BIOLOGICAL IMAGE TRANSFORMATION USING MACHINE-LEARNING MODELS," which issued as U.S. Pat. No. 11,423,256 on Aug. 23, 2022, and which is incorporated herein by reference in its entirety.

Additional automatic optimizations the system may perform includes updating the genetic and/or chemical perturbations applied to the live biological cells. In some embodiments, the system can make decisions regarding the application of perturbations based on the images captured at block 102. For example, if a particular perturbagen pushes the live cells towards a desired cell state (e.g., a healthy cell state), the system may update a subsequent perturbation based on this information. These images can also inform the system of updates to the biological protocols associated with the live biological cells. In some embodiments, updates to the biological protocols include cell culture condition optimization, cell culture plate optimization (e.g., plate size, plate material, etc.), cell proliferation optimization (e.g., optimization of the timing of culture passaging), and optimization of cell differentiation steps.

It should be appreciated by one of ordinary skill in the art that the autonomous platform can be configured to process other types of image data (e.g., MRI, X-ray, CT scan), as well as non-image data, such as electrophysiological data, that are amenable to QPC analysis and modeling for biological subject matter.

Figure 3:
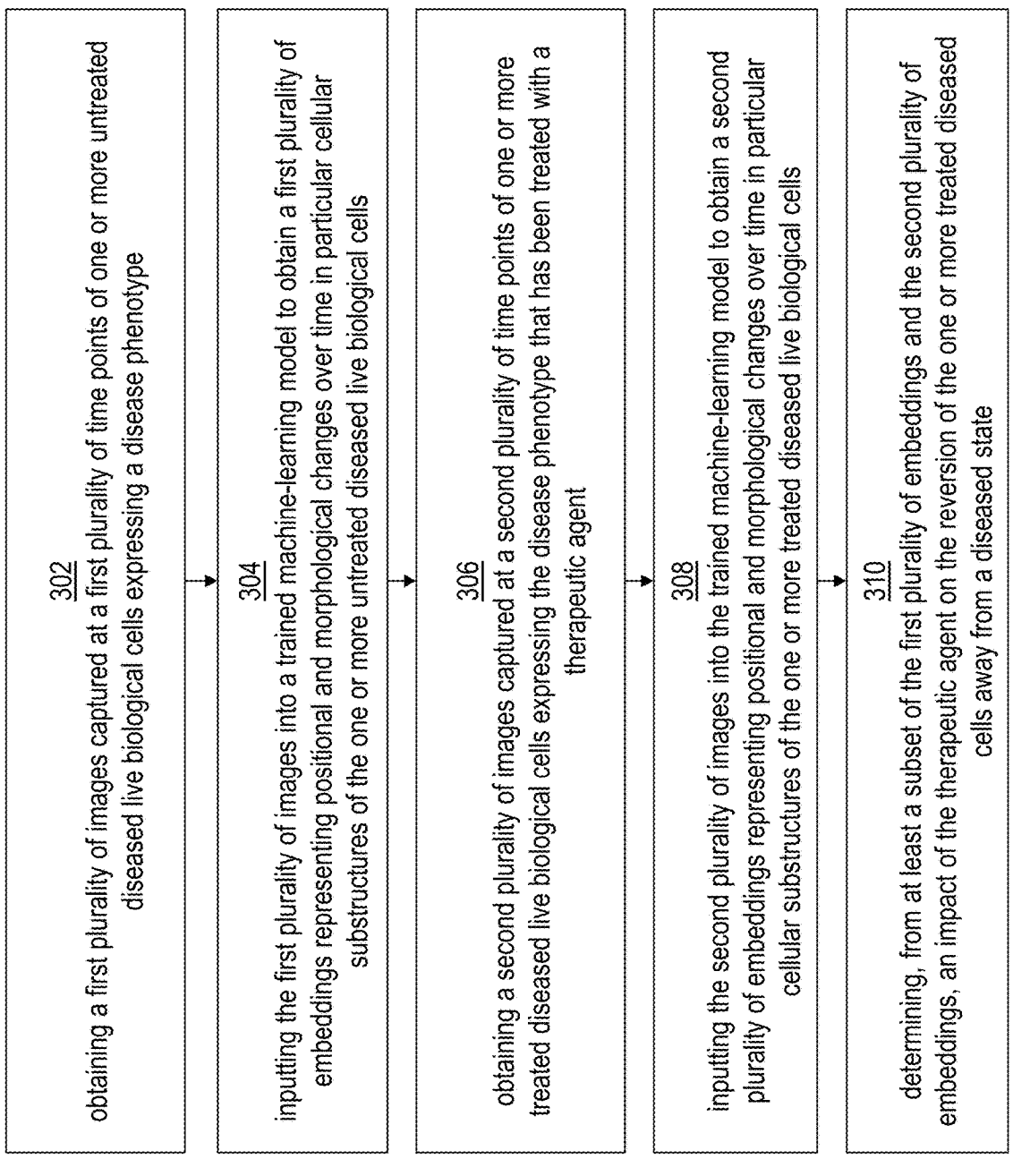
FIG. 3 illustrates an exemplary process for determining the impact of a therapeutic treatment on diseased cells, in accordance with some embodiments.

FIG. 3 illustrates an exemplary process for determining the impact of a therapeutic treatment on diseased cells, in accordance with some embodiments. Process 300 is performed, for example, using one or more electronic devices implementing a software platform. In some examples, process 300 is performed using one or more electronic devices. In some embodiments, process 300 is performed using a client-server system, and the blocks of process 300 are divided up in any manner between the server and one or more client devices. Thus, while portions of process 300 are described herein as being performed by particular devices, it will be appreciated that process 300 is not so limited. In process 300, some blocks are, optionally, combined, the order of some blocks is, optionally, changed, and some blocks are, optionally, omitted. In some examples, additional steps may be performed in combination with the process 300. Accordingly, the operations as illustrated (and described in greater detail below) are exemplary by nature and, as such, should not be viewed as limiting.

At block 302, an exemplary system (e.g., one or more electronic devices) obtains a first plurality of images of one or more untreated diseased live biological cells expressing a disease phenotype. The first plurality of images is captured at a first plurality of time points without destroying the one or more untreated diseased live biological cells.

Figure 4:
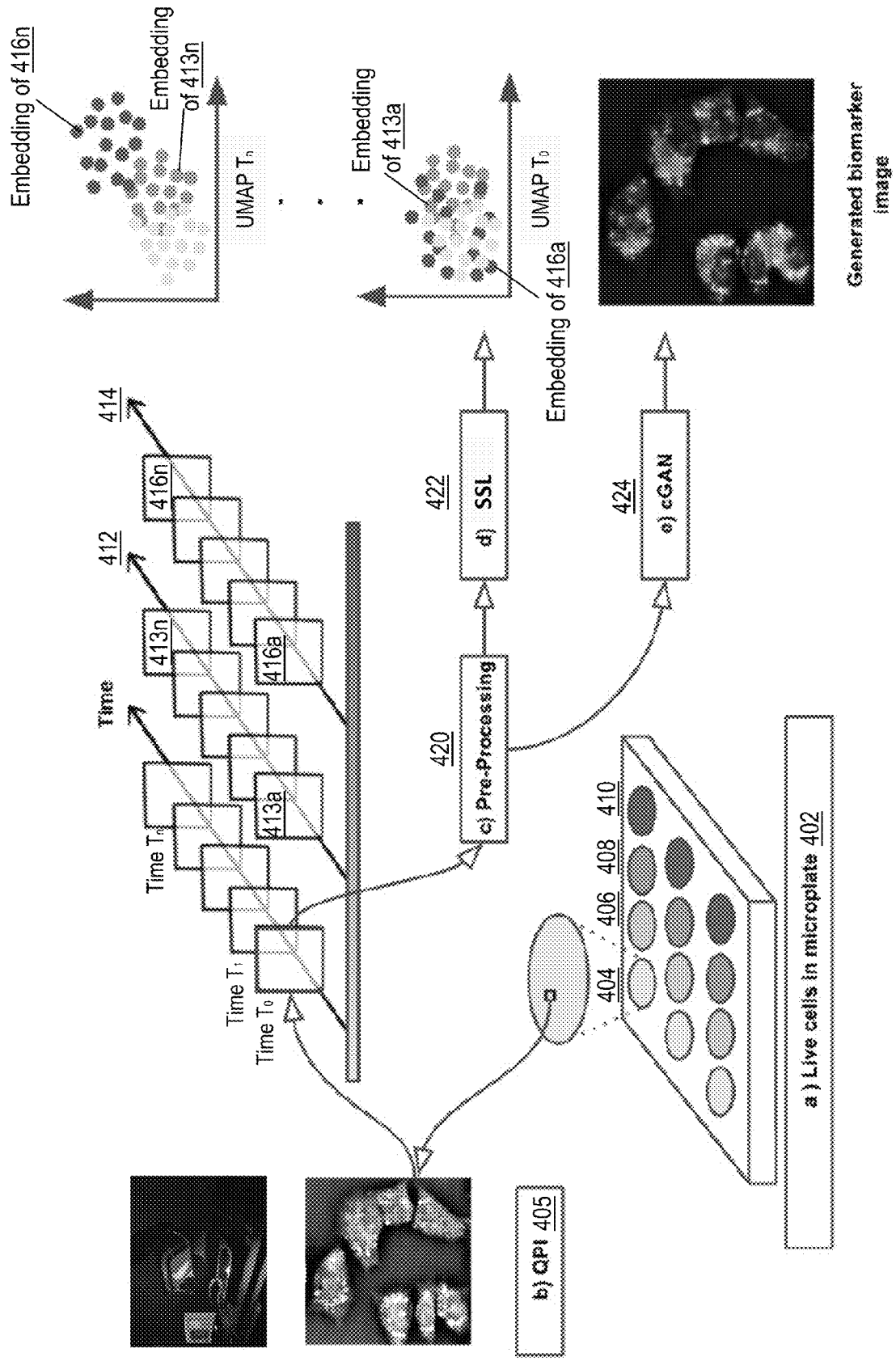
FIG. 4 illustrates an exemplary process for determining the impact of a therapeutic treatment on diseased cells, in accordance with some embodiments.

FIG. 4 illustrates an exemplary process 300, in accordance with some embodiments. With reference to step 402, one or more untreated diseased live biological cells can be cultured in one or more wells 410 of a microplate for continuous imaging. As described below, other wells in the microplate can be used to culture different types of cells. For example, wells 404 can be used to culture healthy live biological cells; wells 406 and 408 can be used to culture diseased cells with different therapeutic agents applied; wells 406 and 408 alternatively can be used to culture diseased cells with different dosages of the same therapeutic agents applied.

With reference to step 405 in FIG. 4, the wells can be imaged using QPI techniques to obtain phase images. In some embodiments, the system uses low photo-toxicity fluorescence and autofluorescence multi spectral imaging techniques to obtain fluorescence images and/or autofluorescence images of the live biological cells. In some embodiments, the system can capture a combination of phase images, fluorescence images, and/or autofluorescence images at a given time.

With reference to step 414 in FIG. 4, the system can obtain a plurality of images including images 416a through 416n (e.g., of diseased live biological cells in wells 410) over time at a plurality of time points $T_0, T_1, \ldots,$ and $T_n$. The imaging techniques used do not cause destruction of the imaged live cells. Accordingly, the live biological cells in the various wells can be continuously imaged and monitored over time.

With reference to step 420 in FIG. 4, the system can perform pre-processing on some or all of the live cell images. In some embodiments, the preprocessing comprises performing segmentation on the live cell images (e.g., cell detection, nucleus detection). In some embodiments, the system performs quality control on the live cell images to obtain quality control measures, which can be used to remove artifacts, determine which live cell images are used for downstream processing, etc. In some embodiments, the system can input the images (e.g., fluorescence images and/or autofluorescence images) into a machine-learning model configured to transform images of a first modality into images of a second modality (e.g., phase images). In some embodiments, the machine-learning model is a generative adversarial network model comprising a discriminator and a generator, and can be trained using ground truth phase images, fluorescence images, and autofluorescence images. In some embodiments, the images of live biological cells (e.g., phase images, fluorescence images, autofluorescence images, etc.) are captured using a microscope according to an optical setup. The optical setup can include an illumination pattern for illuminating the live biological cells. In some embodiments, the illumination pattern can be determined dynamically during the process 300. Additional information of the image transformation model and the identification of the optical setup can be found in U.S. application Ser. No. 17/480,047 titled "BIOLOGICAL IMAGE TRANSFORMATION USING MACHINE-LEARNING MODELS," which issued as U.S. Pat. No. 11,423,256 on Aug. 23, 2022, and which is incorporated herein by reference in its entirety.

In some embodiments, the system uses various phase imaging optical techniques (e.g., QPC, Quadriwave lateral shearing interferometry, spatial light modulator or SLM) to reduce known aberrations and retrieve ground truth quantitative phase information. In some embodiments, the system uses a set of commercially available live cell compatible dyes (or reporter lines) for fast determination of cell stress (e.g., apoptosis, necrosis, position in cell cycle, mitochondrial and ER stress, etc.).

Turing back to FIG. 3, at block 304, the system inputs the first plurality of images into a trained machine-learning model to obtain a first plurality of embeddings representing positional and morphological changes over time in particular cellular substructures of the one or more untreated diseased live biological cells. In the depicted example in FIG. 4, at step 422, the system inputs each image of diseased live cells in well 410, including images 416a and 416n, into a trained machine-learning model to obtain a corresponding embedding. For example, the system can input each image into a trained self-supervised learning model, which is configured to receive an image and output an embedding (i.e., a vector) representing the image in a latent space. In some embodiments, the self-supervised learning model is a DINO Vision Transformer, a SimCLR model, or any other model that learns from unlabeled sample data.

Each embedding can be plotted in a latent space. For example, the embedding corresponding to image 416a captured at $T_0$ can be plotted as a point in the UMAP corresponding to $T_0$. Similarly, the embedding corresponding to image 416n captured at $T_n$ can be plotted as a point in the UMAP corresponding to $T_n$. Translating an input image into an embedding can significantly reduce the size and dimension of the original data. The lower-dimension embedding can be used for downstream processing, as described herein.

In some embodiments (not depicted), the embeddings corresponding to different times (e.g., $T_0$-$T_n$) can be plotted in a single space-time topological space where directionality is available. For example, each image is transformed into an embedding, which can be mapped into a location in the topological space and time-stamped with the time the image was captured. Accordingly, directionality over space and/or time can be obtained across multiple embeddings in the single space-time topological space.

Turning back to FIG. 3, at block 306, the system obtains a second plurality of images of one or more treated diseased live biological cells expressing the disease phenotype that has been treated with a therapeutic agent. The second plurality of images is captured at a second plurality of time points without destroying the one or more treated diseased live biological cells. In the depicted example in FIG. 4, wells 406 can be used to culture diseased cells with a particular therapeutic agent applied. With reference to step 412, the system can obtain a plurality of images (e.g., of treated diseased cells in wells 406) over time at a plurality of time points $T_0$, $T_1$, . . . , and $T_n$.

At block 308, the system inputs the second plurality of images into the trained machine-learning model to obtain a second plurality of embeddings representing positional and morphological changes over time in particular cellular substructures of the one or more treated diseased live biological cells. As discussed above, the system can input each image of live biological cells into a trained self-supervised learning model, which is configured to receive an image and output an embedding (i.e., a vector) representing the image in a latent space. Each embedding can be plotted in a latent space. For example, in the depicted example in FIG. 4, the embedding corresponding to image 413a captured at $T_0$ can be plotted as a point in the UMAP corresponding to $T_0$. Similarly, the embedding corresponding to image 413n captured at $T_n$ can be plotted as a point in the UMAP corresponding to $T_n$.

Figure 5A:
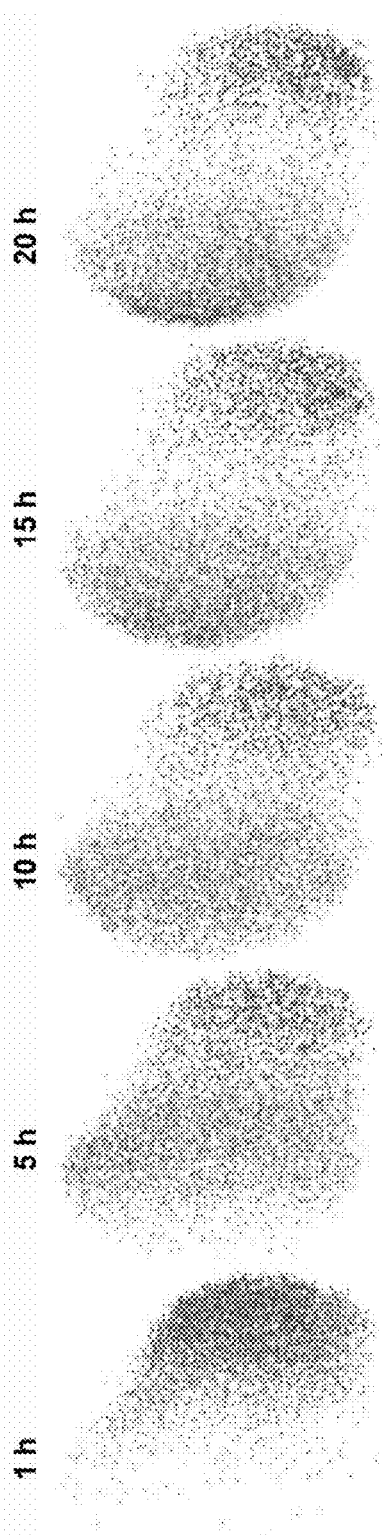
FIG. 5A illustrates exemplary UMAPs corresponding to different time points, in accordance with some embodiments.
Figure 5B:
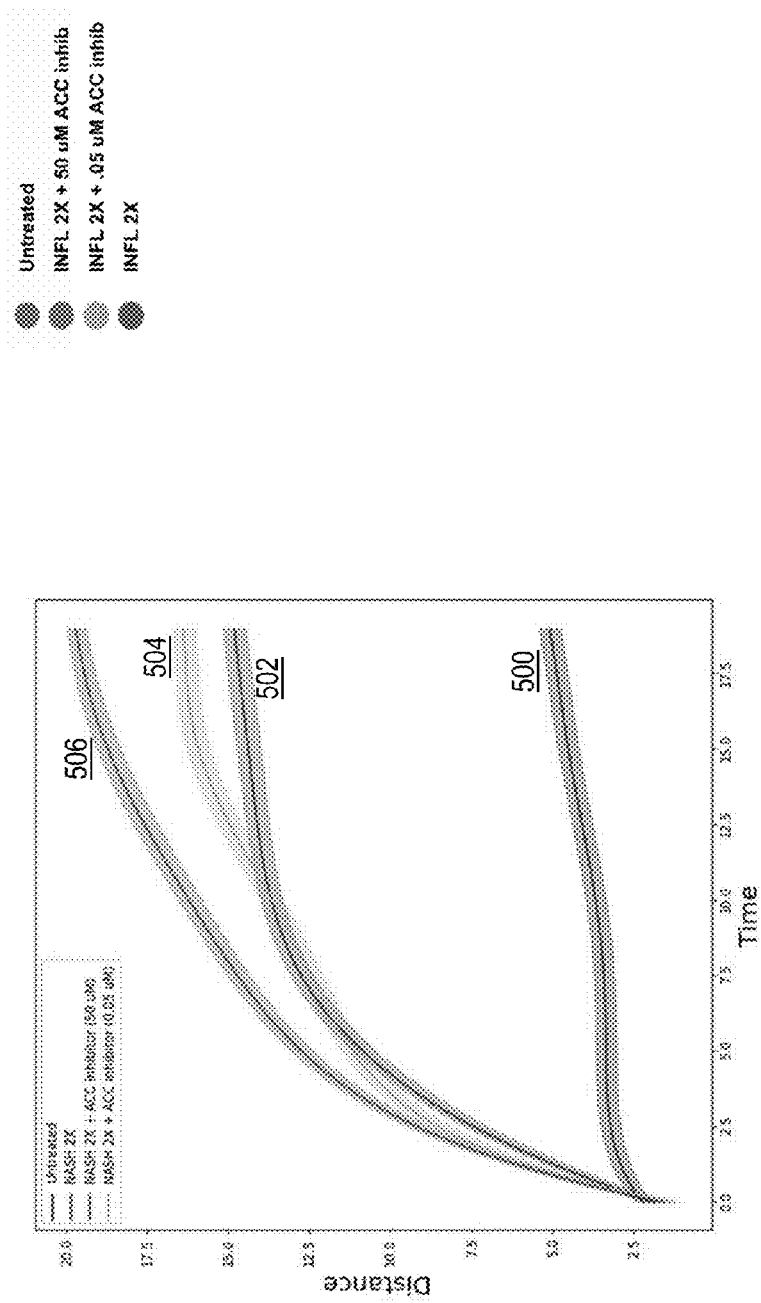
FIG. 5B illustrates evaluating therapeutic treatments (e.g., chemical treatments) by generating time trends, in accordance with some embodiments.
Figure 5C:
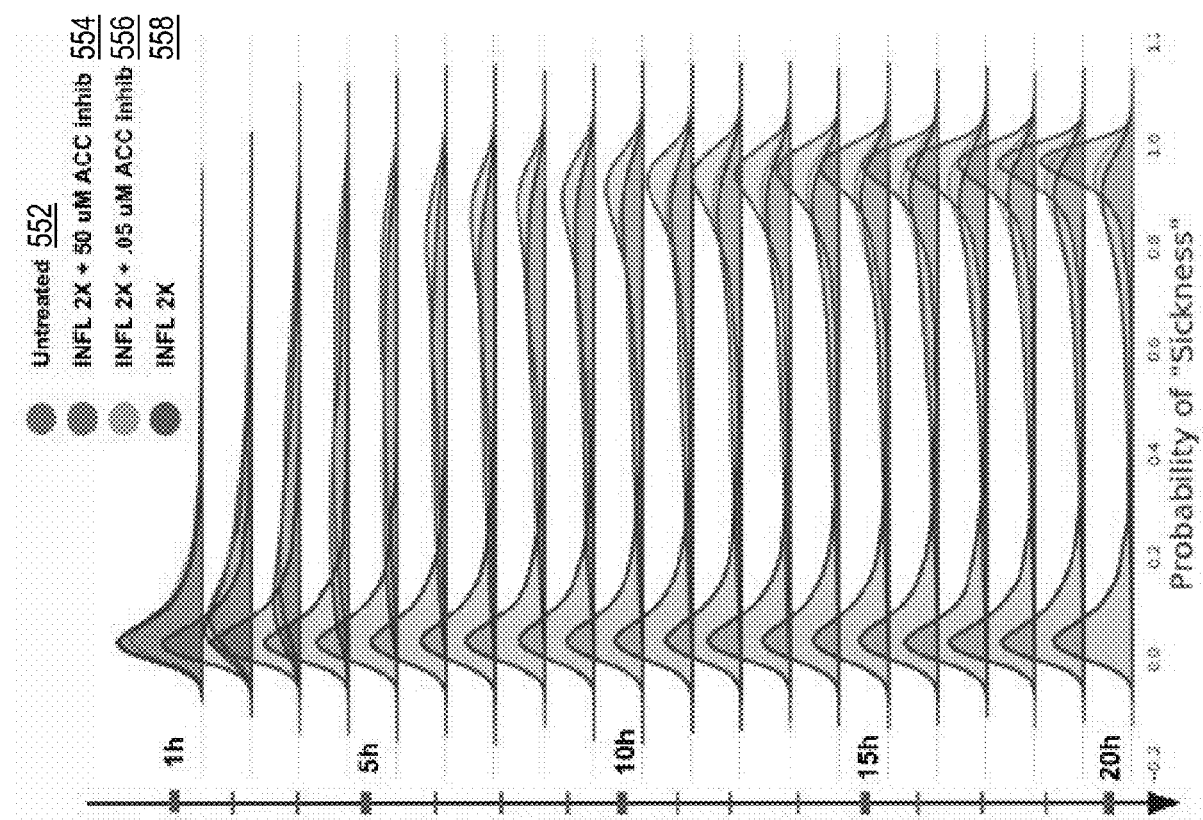
FIG. 5C illustrates evaluating therapeutic treatments by generating distributions, in accordance with some embodiments.

Turning back to block 310 in FIG. 3, the system determines, from at least a subset of the first plurality of embeddings and the second plurality of embeddings, an impact of the therapeutic agent on the reversion of the one or more treated diseased cells away from a diseased state. An exemplary process for this determination is illustrated in FIGS. 5A-5C. FIG. 5A illustrates exemplary UMAPs corresponding to different time points. For example, the UMAPs may be the UMAPs corresponding to $T_0$-$T_n$ in the process in FIG. 4. In FIG. 5A, each UMAP is a plot of embeddings corresponding to live cell images taken at a specific time point. Specifically, the first UMAP is a plot of embeddings corresponding to live cell images taken at Hour 1, the second UMAP is a plot of embeddings corresponding to live cell images taken at Hour 5, the third UMAP is a plot of embeddings corresponding to live cell images taken at Hour 10, the fourth UMAP is a plot of embeddings corresponding to live cell images taken at Hour 15, and the fifth UMAP is a plot of embeddings corresponding to live cell images taken at Hour 20.

In the depicted example in FIG. 5A, four types of cells are cultured in four separate wells: healthy live biological cells (e.g., in wells 404), diseased live biological cells with a first dosage of a therapeutic agent applied (e.g., in wells 406), diseased live biological cells with a second dosage of a therapeutic agent applied (e.g., in wells 408), and untreated diseased live biological cells (e.g., in wells 410). At Hour 1, one or more images are taken for each of the four wells, and the embeddings corresponding to the images are plotted in the first UMAP. The four wells are subsequently imaged at Hour 5, Hour 10, Hour 15, and Hour 20, thereby generating the UMAPS in FIG. 5A.

For example, in FIG. 5A, the UMAPs indicate that, over time, the embeddings corresponding to the healthy live biological cells remain largely stationary in the latent space (indicating a healthy state), while the embeddings corresponding to the untreated diseased live biological cells move farther and farther away from the healthy state. The UMAPs further indicate that, over time, the embeddings corresponding to the diseased cells treated with 50 um ACC inhibitor and the diseased cells treated with 0.05 um ACC inhibitor move slower away from the healthy state than the untreated diseased cells, thus suggesting that the ACC inhibitor treatments may be effectively slowing down the progression of the disease.

FIG. 5B illustrates evaluating therapeutic treatments (e.g., chemical treatments) by generating time trends, in accordance with some embodiments. The embeddings of the healthy live biological cells are provided to a classifier to obtain the corresponding disease scores. In some embodiments, the classifier is configured to receive an embedding and output a disease score. In some embodiments, the classifier is a regression classifier (e.g., logistic regression classifier). The disease scores for the healthy cells are plotted to obtain time trend 600. For example, the point on the time trend 500 at Hour 1 can be based on an average or mean of disease scores of embeddings corresponding to live cells imaged at Hour 1, and the width of the time trend 500 at Hour 1 can indicate the variance of the disease scores. The time trends 502, 504, and 506 can be generated in a similar manner.

Similar to FIG. 5A, the time trends indicate that, over time, the healthy live biological cells remain largely healthy (as shown by the time trend 500), while the untreated diseased live biological cells move farther and farther away from the healthy state (as shown by the increasing disease scores in time trend 506). The time trends further indicate that, over time, the diseased cells treated with 50 um ACC inhibitor and the diseased cells treated with 0.05 um ACC inhibitor move slower away from the healthy state, thus suggesting that the ACC inhibitors treatments may be effectively slowing down the progression of the disease. In FIG. 5B, it can be further observed that the dosage of 0.05 um ACC inhibitor outperforms the dosage of 50 um ACC inhibitor starting around Hour 10. It can be further observed that the treatment effect of 0.05 um ACC inhibitor plateaus at around Hour 15. Accordingly, the time trends can be used to select a dosage of the treatment and determine time intervals for administering the treatment (e.g., to administer the treatment at a first time point so that full effect can be observed by a second time point).

FIG. 5C illustrates evaluating therapeutic treatments by generating distributions, in accordance with some embodiments. The embeddings of the healthy live biological cells are provided to a classifier to obtain the corresponding disease scores. In some embodiments, the classifier is configured to receive an embedding and output a disease score. In some embodiments, the classifier is a regression classifier (e.g., logistic regression classifier). The disease scores for the healthy cells are plotted to obtain the distribution at Hour 1, Hour 5, . . . and Hour 20. The distributions for other cell types at a particular time point can be generated in a similar manner.

Similar to FIGS. 5A and 5B, the distributions in FIG. 5C indicate that, over time, the healthy live biological cells remain largely healthy (as shown by the location and shape of the distributions 552 over time), while the untreated diseased live biological cells move farther and farther away from the healthy state (as shown by the change in location and shape of the distributions 558 over time). The distributions further indicate that, over time, the diseased cells treated with 50 um ACC inhibitor (distribution 554) and the diseased cells treated with 0.05 um ACC inhibitor (distribution 556) move slower away from the healthy state, thus suggesting that the ACC inhibitor treatments may be effectively slowing down the progression of the disease.

Figure 6:
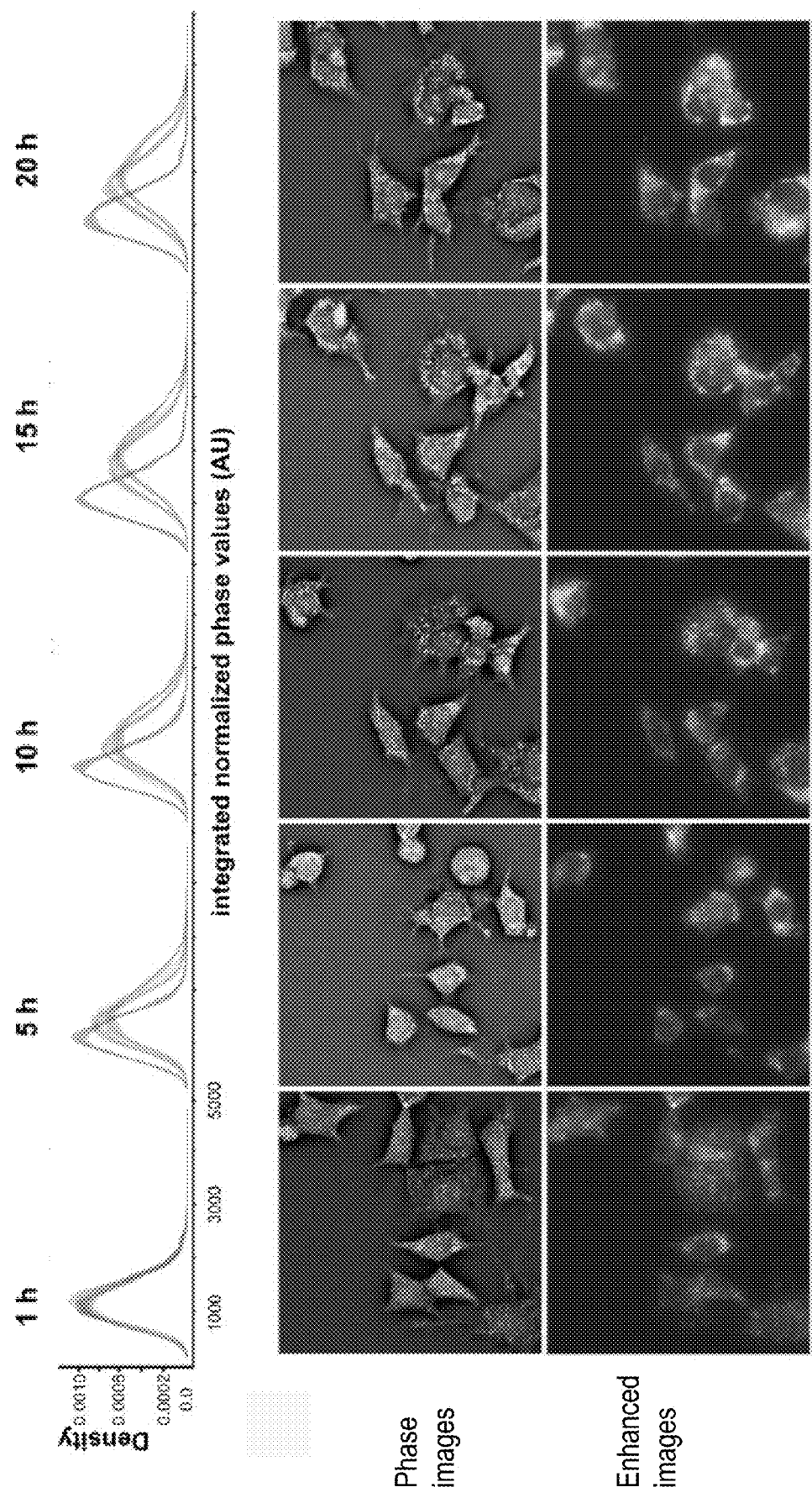
FIG. 6 illustrates phase images at different time points and the corresponding enhanced images with a biomarker, in accordance with some embodiments.

In addition to generating UMAPs, time trends, and distributions, the system can also process the phase images using a generative adversarial network (GAN) model to increase the interpretability of the results. The GAN model can be trained on fixed samples to translate static phase images to images depicting a biomarker (e.g., a lipid fluorescence biomarker). For example, at 424, the system can study the response of hepatocytes to inflammation stimulation (e.g., the effect of inflammation stimulation on lipid accumulation). Lipid accumulation implicated in multiple diseases, both due to decreased (e.g., lipodystrophy) and increased (e.g., NAFLD) lipid levels and lipid droplet accumulation in tissues. A common marker to measure lipid accumulation is BODIPY, a fluorescence marker that requires fixing the cells. As shown in FIG. 6, the phase images at different time points can be inputted into a trained GAN model to generate enhanced images with the biomarker (e.g., BODIPY images). The system can further detect intracellular lipid droplets in the enhanced images and determine integrated phase values of intracellular lipid droplets in the images over time. Accordingly, the system can use QPI to quantify and interpret lipid accumulation in live cells.

Accordingly, modeling of QPI of live hepatocytes can characterize their response to exposure to increased doses of an inflammation treatment, and therefore guide the selection of relevant exposures. The system can further evaluate the efficacy of a chemical treatment intended to reverse the inflammation, ACC inhibitor, and show that it reverts cell morphology closer to the untreated cells morphology. Accordingly, the combination of QPI imaging, self-supervised embedding and pre-trained models that predict fluorescent dyes, offers an efficient approach to establish in vitro models for chemical screening.

Figure 7:
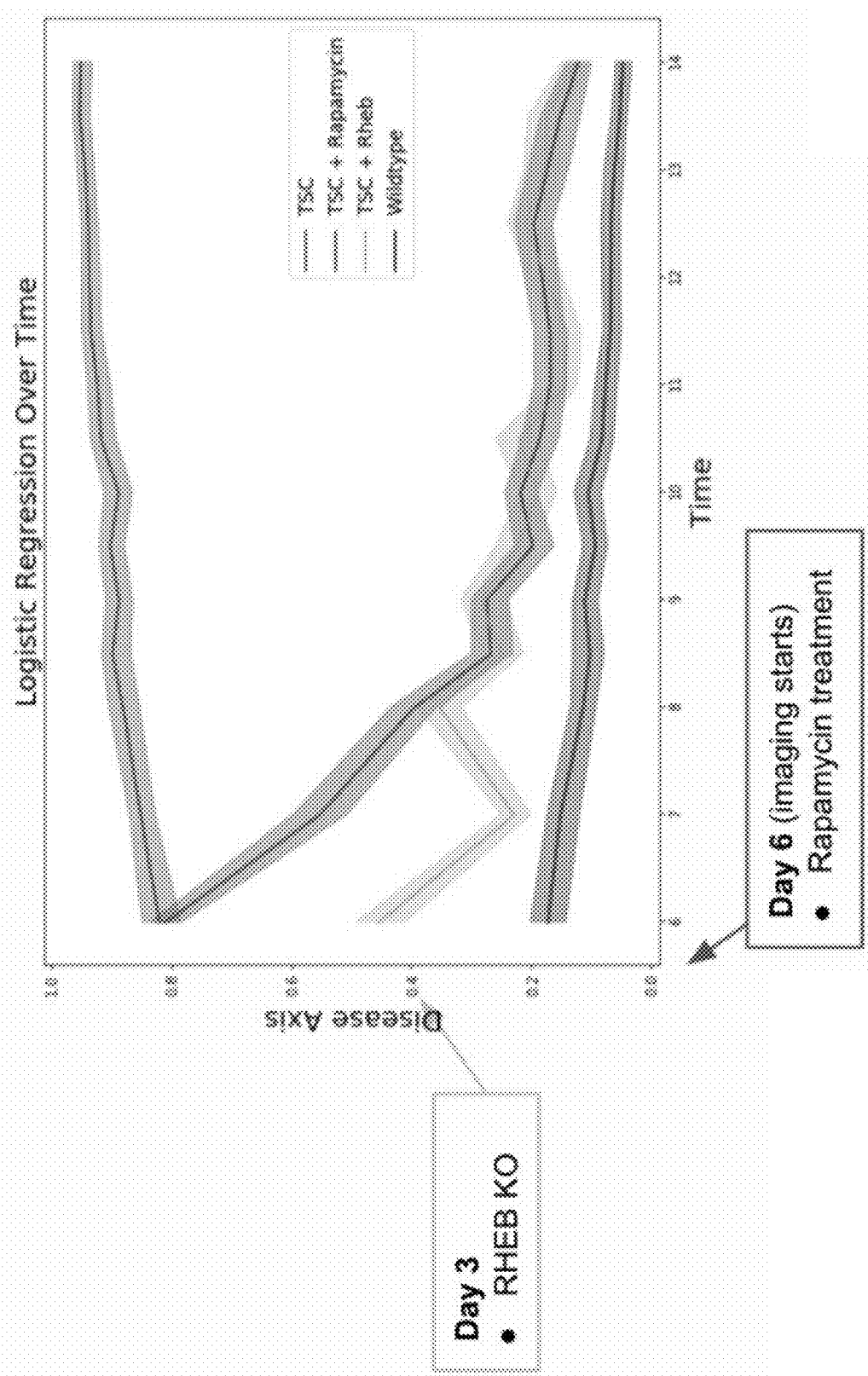
FIG. 7 illustrates evaluating therapeutic treatments (e.g., genetic treatments) by generating time trends, in accordance with some embodiments.

FIG. 7 illustrates evaluating therapeutic treatments (e.g., genetic treatments) by generating time trends, in accordance with some embodiments. In the depicted example in FIG. 7, four types of cells are cultured in four separate wells: healthy live biological cells (e.g., in wells 404), diseased live biological cells with a first therapeutic agent Rapamycin applied (e.g., in wells 406), diseased live biological cells with a second therapeutic agent RHEB KO applied (e.g., in wells 408), and untreated diseased live biological cells (e.g., in wells 410). One or more images are taken for each of the four wells at a plurality of time points. The time trends can be generated in a similar manner as described above with reference to FIG. 5B. Accordingly, the efficacy of the two treatments can be evaluated. The time trends can be used to select a treatment and determine time intervals for administering the treatment (e.g., to administer the treatment at a first time point so that full effect can be observed by a second time point).

Figure 8A:
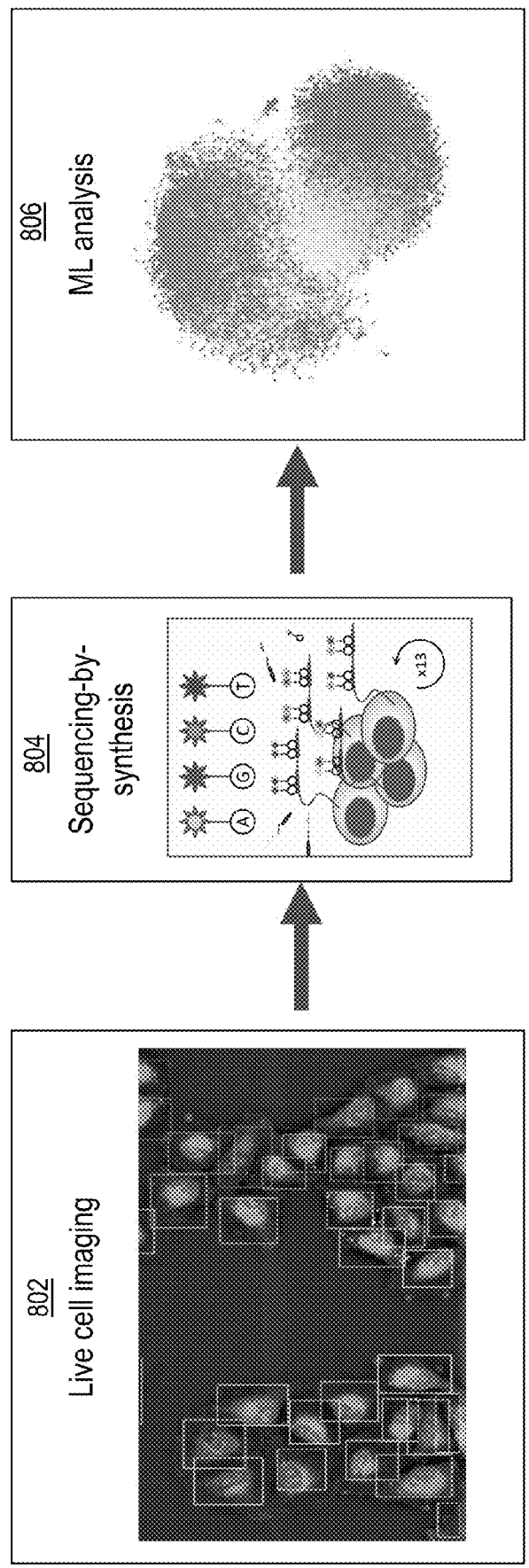
FIG. 8A illustrates an exemplary workflow for determining an impact of a therapeutic agent on diseased cells using a trained machine-learning model, in accordance with some embodiments.

FIG. 8A illustrates an exemplary workflow for determining an impact of a therapeutic agent (e.g., a genetic treatment) on diseased cells (e.g., cell stimulated to induce a biological pathway) using a trained machine-learning model, in accordance with some embodiments. The combination of live cell imaging, biological pathway stimulation, and introduction of genetic perturbations allows for mapping of the connectivity or independence of genetic pathways, thereby enabling the discovery of novel biological pathways. At 802, phase images (e.g., QPC images) are captured of live biological cells comprising one or more guide RNAs (gRNAs) targeting specific genes. Specifically, A549 live biological cells are transfected with the human CRISPR activation library (Calabrese P65-HSF) targeting genes in the nuclear factor Kappa B (NF-κB) pathway. An exemplary outline of the NF-κB pathway is shown in FIG. 8B.

In the example depicted in FIG. 8A, the cells are contacted with approximately 400 gRNAs targeting 30 genes in the NF-κB pathway for knockdown, with approximately 10 gRNAs/gene, and approximately 100 non-targeting gRNAs serving as controls. Each gRNA comprising a specific barcode sequence used to identify the targeted gene during downstream analyses. The QPC images are captured following stimulation with interleukin-1l3 (IL-1β) induced NF-κB pathway activation. Live QPC images are captured over a period of 19 hours, at a magnification of 20×, and 1 frame was captured at 45 minute intervals. The genetic barcodes identifying each gRNA perturbation can be identified at 804 using sequencing-by-synthesis, via pooled optical screening (e.g., pooled optical screening (POSH)) analysis of the live biological cells. POSH allows for matching of the specific gRNA barcode sequence, corresponding to a genetic treatment, with the QPC images. In some embodiments, the gRNA barcode, or a portion thereof, is sequenced in situ using sequencing-by-synthesis. It will be appreciated by one of skill in the art that other suitable sequencing methods, such as but not limited to, sequencing-by-ligation, sequencing-by-hybridization, sequencing-by-binding, RNAseq, single cell RNAseq (scRNAseq), fluorescent in situ sequencing (FISSEQ), and/or hybridization-based in situ sequencing. In some embodiments, the sequencing of the gRNA barcode sequence does not destroy the cells.

The live QPC images are inputted into a trained machine-learning model to obtain sets of embeddings 806 representing positional and morphological characteristics in particular cellular substructures of the one or more live cells stimulated with IL-1β (e.g., disease cells) following application of the genetic treatment. These embedding are used, for example, to determine an impact of the genetic treatment on the reversion of the one or more treated diseased cells away from a diseased state.

Figure 8C:
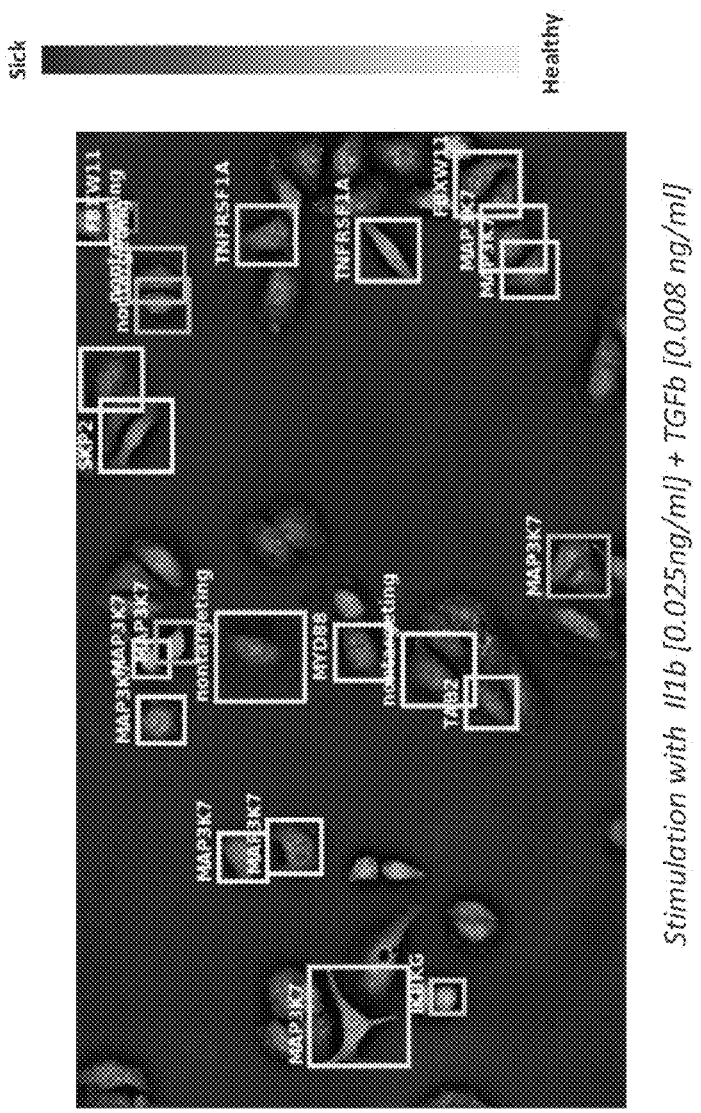
FIG. 8C illustrates QPC images of A549 cells stimulated with Interleukin-1β (IL-1β) and transforming growth factor-β (TGFβ), in accordance with some embodiments.
Figure 8B:
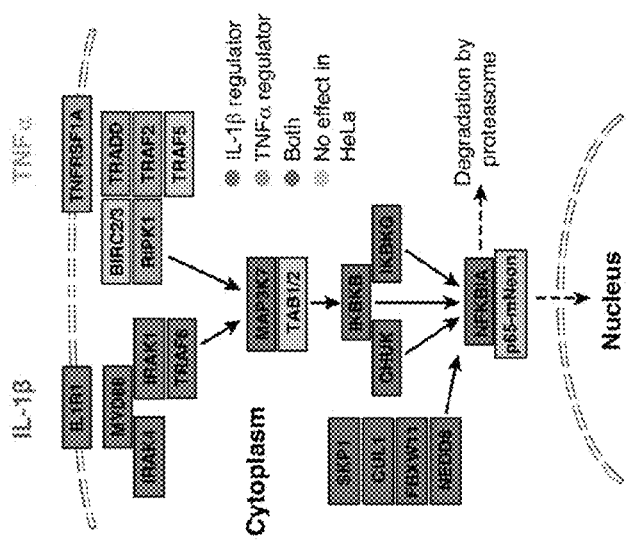
FIG. 8B illustrates an exemplary outline of the nuclear factor Kappa B (NF-κB) pathway, in accordance with some embodiments.

QPC images of the A549 cells of FIG. 8A stimulated with 0.025 ng/mL IL-1β and 0.008 ng/mL transforming growth factor-0 (TGFβ) are shown in FIG. 8C, in accordance with some embodiments. TGFβ stimulation is an alternative way to stress the cells and activate shared pathways with IL-1β. Combined treatment with TGFβ and IL-1β may strongly activate the NF-κB pathway to push the cells towards additional inflammation and/or allow for the detection of additional genes associated with the NF-κB pathway. As illustrated in the example depicted in FIG. 8C, live QPC images enable the detection and tracking of genetic treatments (e.g., perturbations) of NF-κB pathway genes with gRNAs following IL-1β stimulation. Each genetic perturbation introduced by a gRNA may be evaluated for an impact on the diseased cells over time. In FIG. 8C, the system evaluates the impact of the genetic perturbation over time directly by analyzing the QPC images. A particular cell may be scored as "healthy" or "sick". At this stage, the genetic barcodes identifying each gRNA perturbation can be identified using sequencing-by-synthesis, via pooled optical screening (e.g., POSH), as illustrated in 804 of FIG. 8A. In some embodiments, cells may be assigned continuous scores, to enable classification on a broader spectrum of sick versus healthy.

Figure 8D:
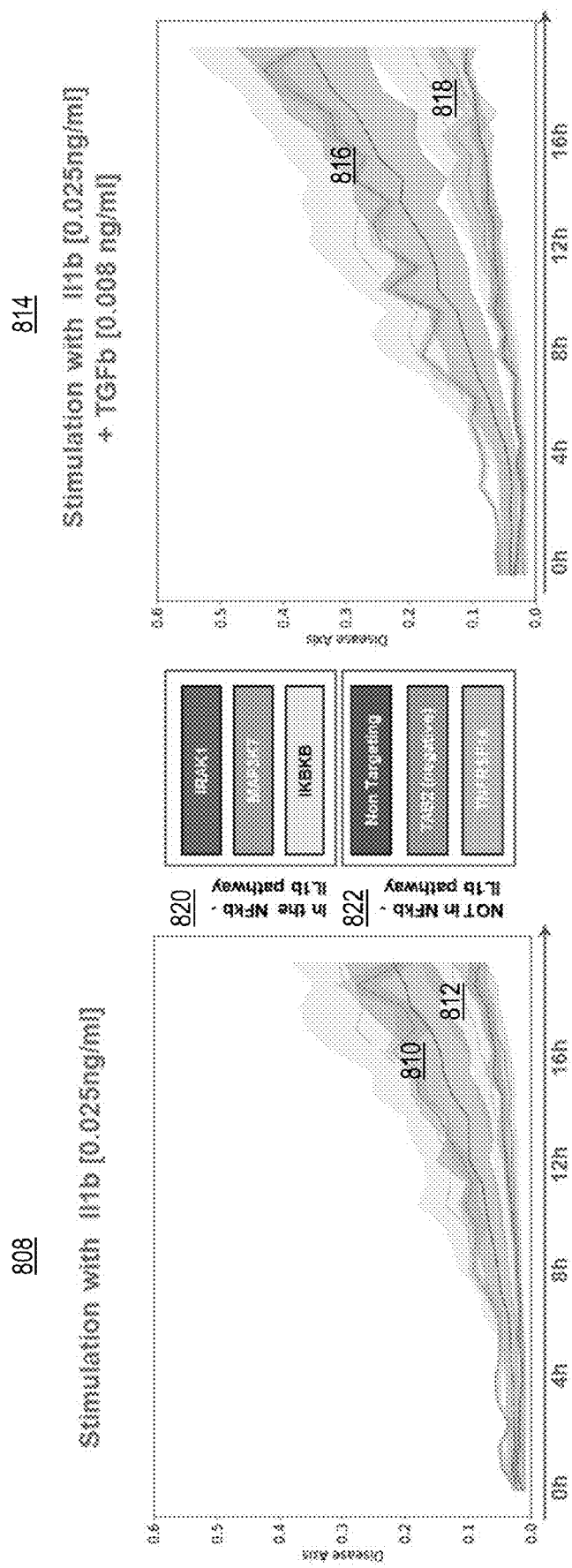
FIG. 8D illustrates evaluating genetic treatments by generating time trends, in accordance with some embodiments.

FIG. 8D illustrates evaluating genetic treatments (e.g., gRNA treatments) by generating time trends, in accordance with some embodiments. The embeddings of the live biological cells from FIG. 8C are inputted into a classifier to obtain the corresponding disease scores. In some embodiments, the classifier is configured to receive an embedding and output a disease score. In some embodiments, the classifier is a regression classifier (e.g., logistic regression classifier). The disease scores for live biological cells stimulated with IL-1β (e.g., diseased cells) are plotted to obtain time trends in graph 808, and the disease scores for live biological cells stimulated with IL-1β and TGFβ are plotted to obtain time trends in graph 814. The disease scores for cells treated with gRNAs targeting genes not in the NF-κB pathway 822 are plotted to obtain time trends 810 and 816, while the disease scores for cells treated with gRNAs targeting genes in the NF-κB pathway 820 are plotted to obtain time trends 812 and 818. For example, the time trend 810 at Hour 4 can be based on an average or mean of disease scores of live cells imaged at Hour 4, and the width of the time trend 810 at Hour 4 can indicate the variance of the disease scores. The time trends 812, 816, and 829 can be generated in a similar manner.

The time trends in FIG. 8D indicate that, over time, the live biological cells treated with gRNAs targeting NF-κB pathway genes 820 rescue the cells from IL-1β exposure (as shown by the time trend 812) and rescue the cells from a combination of IL-1β and TGFβ exposure (as shown by the trend 818), while the cells treated with gRNAs not targeting NF-κB pathway genes 822 move farther and farther away from the healthy state (as shown by the increasing disease scores in time trends 810 and 816). The time trends further indicate that, over time, the cells treated with gRNAs targeting NF-κB pathway genes move slower away from the healthy state, thus suggesting that these genetic perturbations may be effectively slowing down the progression of the disease resulting from IL-1β or combined IL-1β and TGFβ exposure. It can be further observed that the treatment effect of the gRNAs targeting NF-κB pathway genes plateaus at around Hour 15. Accordingly, time trends can be used to select a dosage of the treatment and determine time intervals for administering the treatment (e.g., to administer the treatment at a first time point so that full effect can be observed by a second time point).

Figure 9:
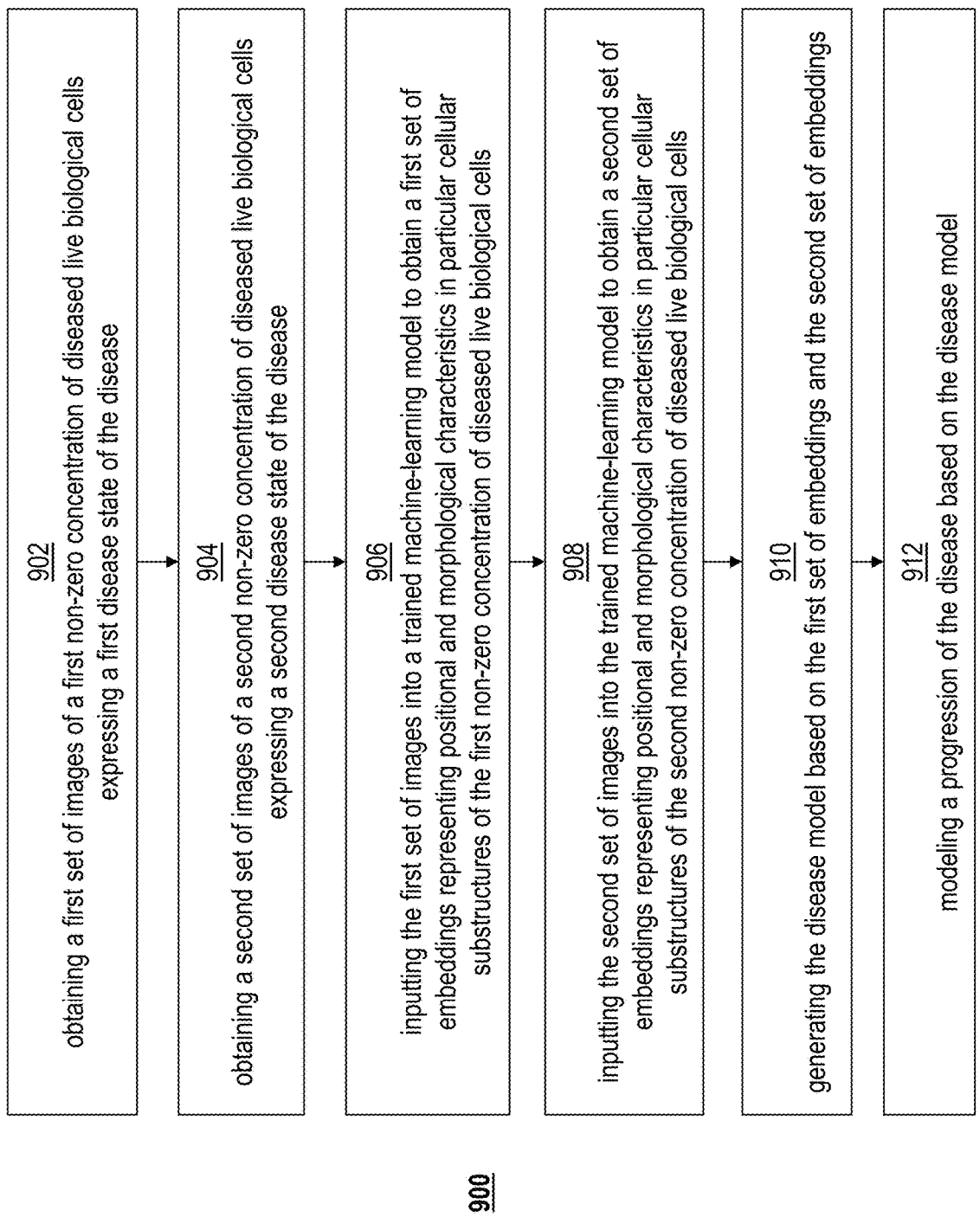
FIG. 9 illustrates an exemplary process for modeling a progression of the disease having a plurality of disease states, in accordance with some embodiments.

FIG. 9 illustrates an exemplary process for modeling a progression of the disease having a plurality of disease states, in accordance with some embodiments. Process 900 is performed, for example, using one or more electronic devices implementing a software platform. In some examples, process 900 is performed using one or more electronic devices. In some embodiments, process 900 is performed using a client-server system, and the blocks of process 900 are divided up in any manner between the server and one or more client devices. Thus, while portions of process 900 are described herein as being performed by particular devices, it will be appreciated that process 900 is not so limited. In process 900, some blocks are, optionally, combined, the order of some blocks is, optionally, changed, and some blocks are, optionally, omitted. In some examples, additional steps may be performed in combination with the process 900. Accordingly, the operations as illustrated (and described in greater detail below) are exemplary by nature and, as such, should not be viewed as limiting.

At block 902, an exemplary system (e.g., one or more electronic devices) obtains a first set of images of a first non-zero concentration of diseased live biological cells expressing a first disease state of the disease. At block 904, the system obtains a second set of images of a second non-zero concentration of diseased live biological cells expressing a second disease state of the disease. The images can be generated in a manner similar to FIG. 1 (102), FIG. 4 (402), or FIG. 5B (506). In some embodiments, the first set of images and the second set of images comprise phase images. In some embodiments, the first set of images and the second set of images are generated based on fluorescence images or autofluorescence images.

Figure 10:
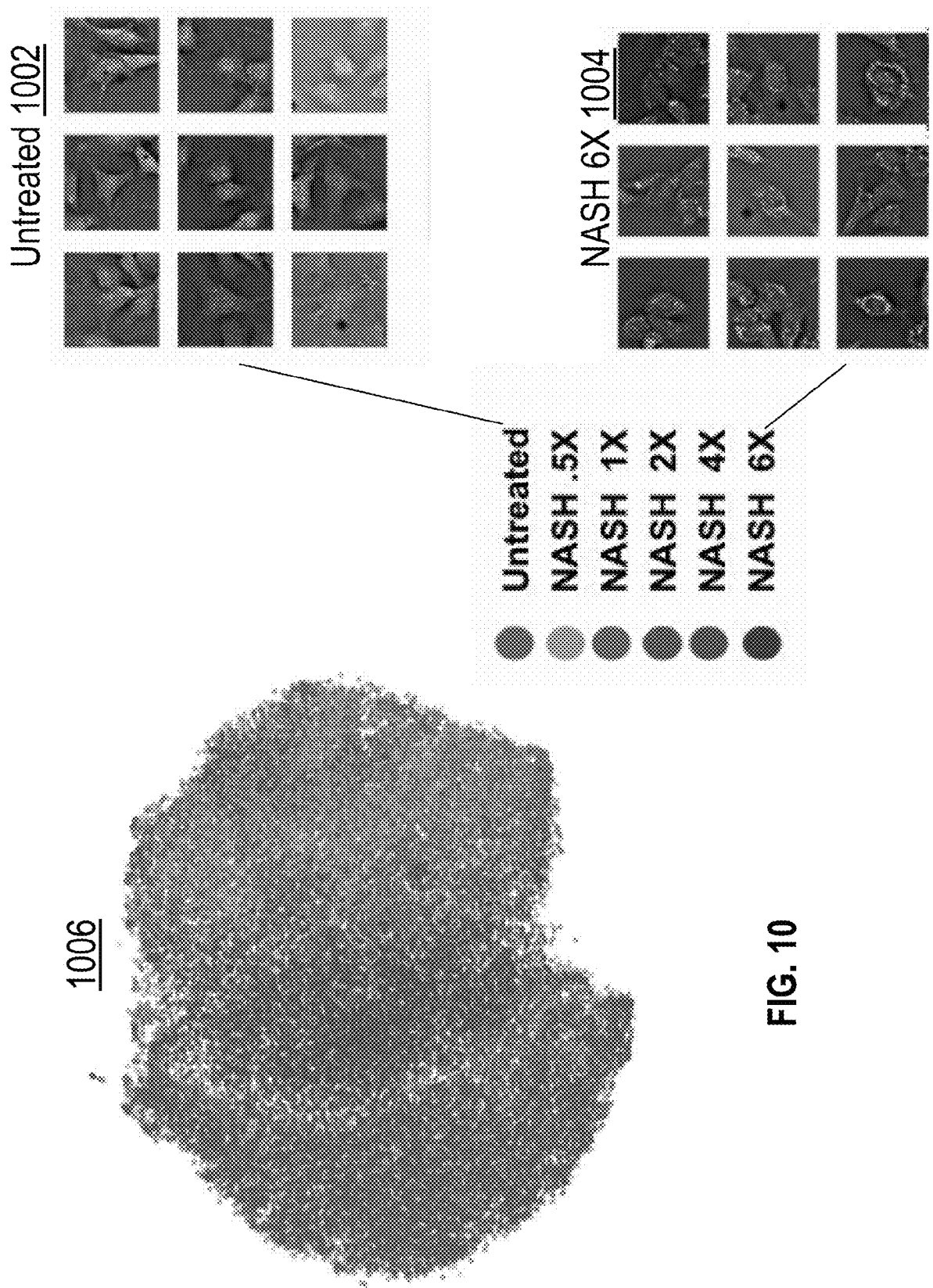
FIG. 10 illustrates an exemplary experiment for studying the response of hepatocytes to inflammation stimulation, in accordance with some embodiments.

FIG. 10 illustrates an exemplary experiment using process 900 for studying the response of hepatocytes to inflammation stimulation, in accordance with some embodiments. In the experiment, HepG2, a liver hepatocellular carcinoma cell line is used. Specifically, live cells are cultured in a control medium (i.e., "untreated"), for example, in a first well. Further, five non-zero concentrations (0.5×, 1×, 2×, 4×, 6×) of a reference inflammation stimulation cocktail ([Il1b] 50 ng/mL, [Tnfa] 25 ng/mL, [Tgfb] 8 ng/mL, [Sodium oleate] 65 uM, [Palmitic acid] 45 uM) are cultured, for example, in five separate wells. In the experiment, a batch of images is captured of cells in each well, thereby generating six batches of images. As examples, FIG. 10 depicts nine phase images of untreated live cells 1002 and nine phase images of a cell culture having 6× concentration of the inflammation simulation cocktail 1004.

At block 906, the system inputs the first set of images into a trained machine-learning model to obtain a first set of embeddings representing positional and morphological characteristics in particular cellular substructures of the first non-zero concentration of diseased live biological cells. At block 908, the system inputs the second set of images into the trained machine-learning model to obtain a second set of embeddings representing positional and morphological characteristics in particular cellular substructures of the second non-zero concentration of diseased live biological cells. In the example depicted in FIG. 10, the system can input the six batches of phase images of the various cell cultures into the model to obtain six batches of embeddings.

In some embodiments, the trained machine-learning model is a self-supervised machine-learning model similar to the model described with reference to FIG. 1 (106), FIG. 2, and FIG. 5C (552). In some embodiments, the trained machine-learning model comprises a neural network. In some embodiments, it can be pre-trained using unlabeled images that do not depict biological samples. In some embodiments, the trained machine-learning model is configured to be retrained using unlabeled images of biological samples.

At block 910, the system generates the disease model based on the first set of embeddings and the second set of embeddings. In some embodiments, generating the disease model comprises mapping the first set of embeddings and the second set of embeddings into a topological space. In some embodiments, the first set of embeddings and the second set of embeddings are time-stamped in the topological space. In the depicted example in FIG. 10, the six patches of embeddings are mapped into a UMAP 1006.

In some embodiments, the system can identify a location of a first cluster of embeddings based on the first set of embeddings in the topological space and generate a representation of the first disease state based on the location of the first cluster. The system can further identify a location of a second cluster of embeddings based on the second set of embeddings in the topological space and generate a representation of the second disease state based on the location of the second cluster. In the depicted example in FIG. 10, the six batches of embeddings can be observed to form six clusters in the UMAP 1006. Thus, the system can identify the locations of the six clusters, allowing discrimination between these simulations in the latent space and modeling of the progression of the disease.

At block 912, a progression of the disease may be modeled based on the generated disease model. In some embodiments, the system can further study a potential reversion of the observed phenotype by treating the cells with a therapeutic agent (a chemical treatment, a genetic treatment, or any combination thereof). FIGS. 8A-8D, described above, illustrates an experiment in which two dosages of a therapeutic agent are applied to cell cultures having 2× concentration of the inflammation simulation cocktail. As described above, the system is able to track over 20 hours the dose-dependent effect of the treatments. Moreover, using a cGAN trained to predict BODIPY, the system is able to detect a reduction in the lipid droplet contents of cells treated with 2× the INFL stimulation, as expected from the known mechanism of action of this drug. Thus, modeling of QPI of live hepatocytes can characterize their response to exposure to increased doses of an inflammation treatment, and therefore guide the selection of relevant exposure. The same methodology can be used to evaluate the efficacy of a chemical treatment intended to reverse the inflammation, ACC inhibitor, and show that it reverts cell morphology closer to the untreated cells morphology. Accordingly, the combination of QPI imaging, self-supervised embedding and pre-trained models that predict fluorescent dyes, offers an efficient approach to establish in vitro models for chemical screening.

Figure 11:
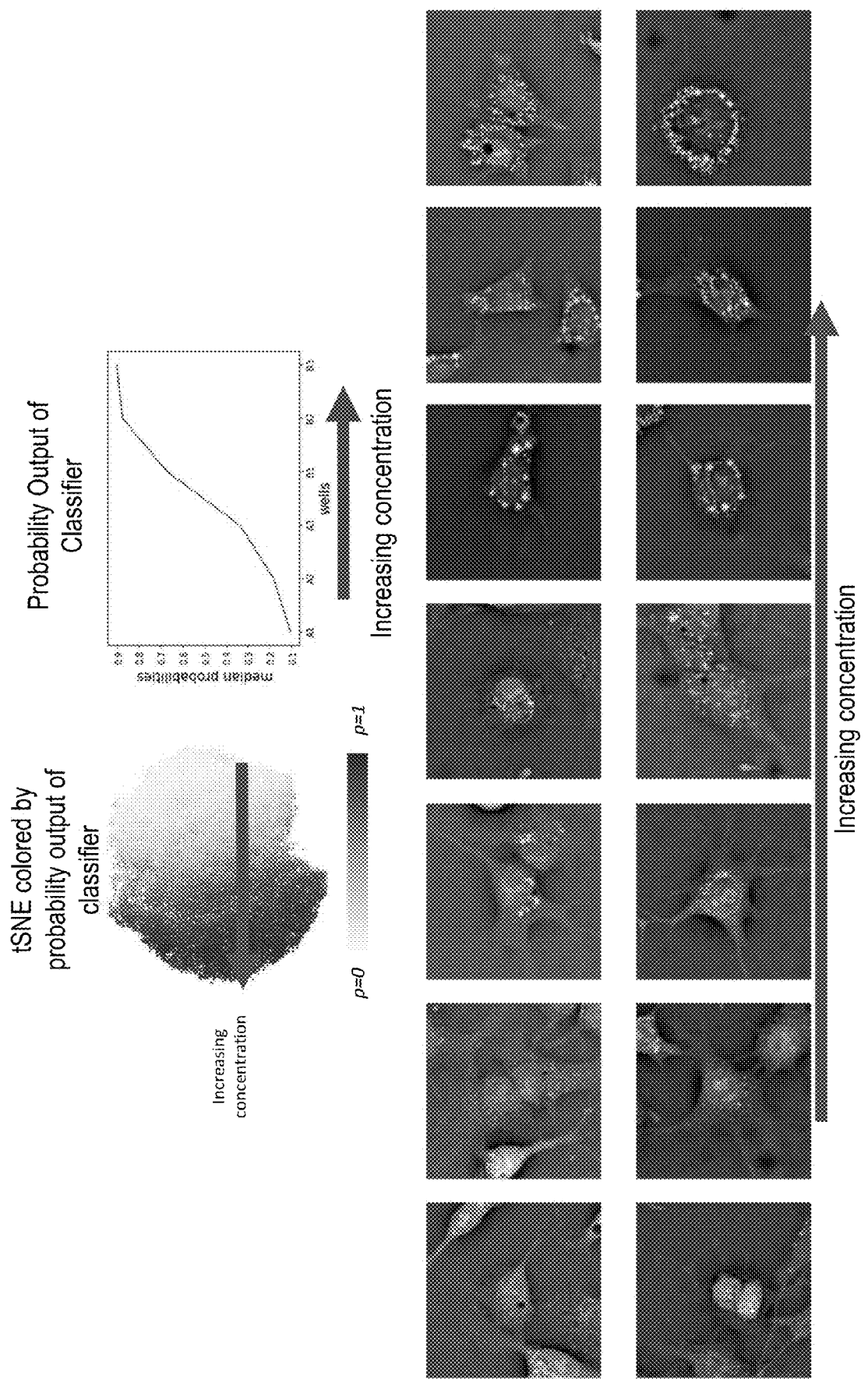
FIG. 11 illustrates another example of generating a disease model, in accordance with some embodiments.

FIG. 11 illustrates another example of generating a disease model, in accordance with some embodiments. As shown, increasing concentrations of an exposure that increases expression of a disease of interest corresponds to shifts in morphological characteristics of live cells in the images, as well the shift in locations of the embeddings in the latent space and an increase of disease scores output by a classifier.

Figure 12:
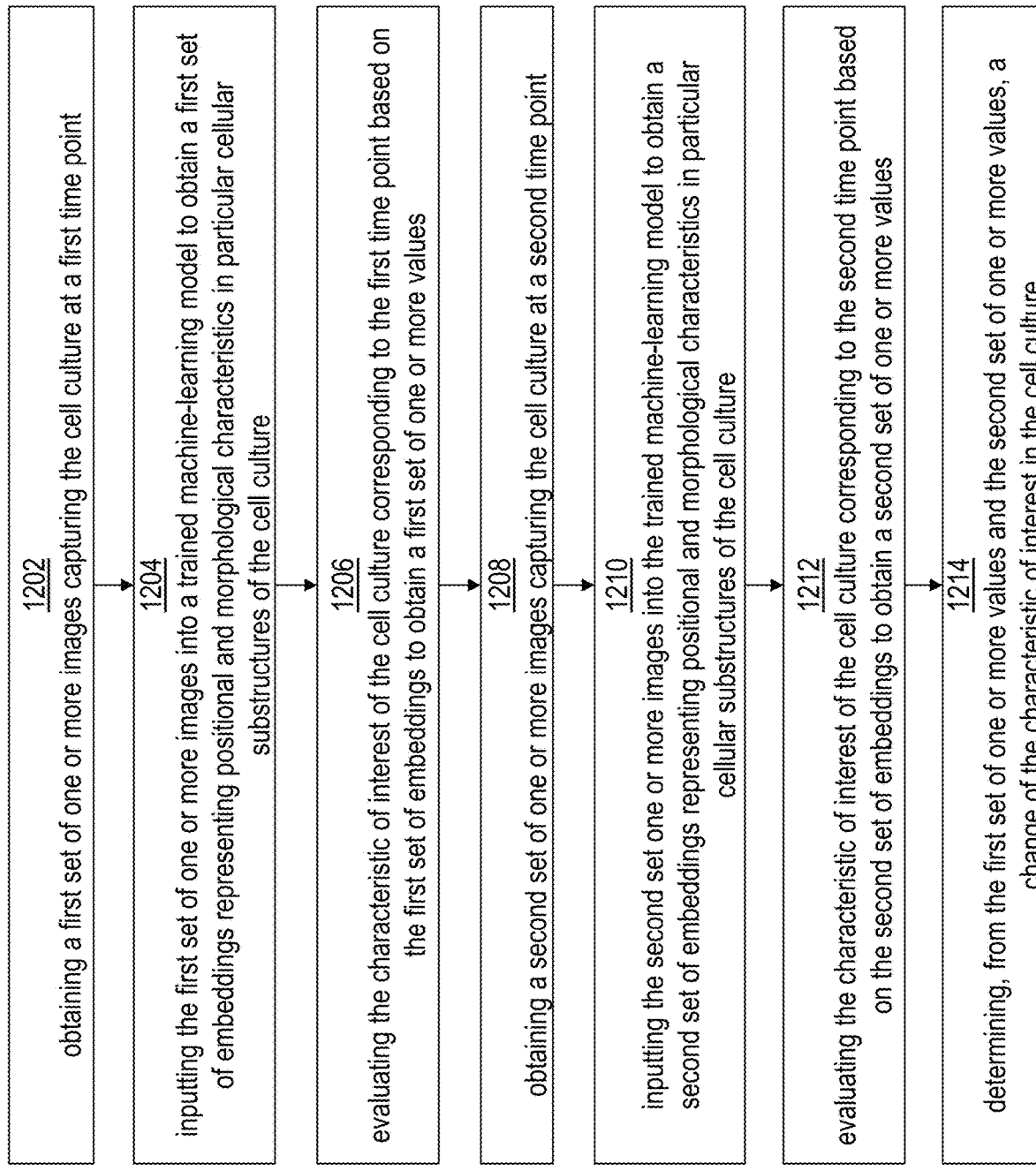
FIG. 12 illustrates an exemplary process for modeling a characteristic of interest of a cell culture comprising one or more live biological cells, in accordance with some embodiments.

FIG. 12 illustrates an exemplary process for modeling a characteristic of interest of a cell culture comprising one or more live biological cells, in accordance with some embodiments. Process 1200 is performed, for example, using one or more electronic devices implementing a software platform. In some examples, process 1200 is performed using one or more electronic devices. In some embodiments, process 1200 is performed using a client-server system, and the blocks of process 1200 are divided up in any manner between the server and one or more client devices. Thus, while portions of process 1200 are described herein as being performed by particular devices, it will be appreciated that process 1200 is not so limited. In process 1200, some blocks are, optionally, combined, the order of some blocks is, optionally, changed, and some blocks are, optionally, omitted. In some examples, additional steps may be performed in combination with the process 1200. Accordingly, the operations as illustrated (and described in greater detail below) are exemplary by nature and, as such, should not be viewed as limiting.

In some embodiments, the one or more live biological cells are mammalian cells. In some embodiments, the one or more live biological cells are healthy cells. In some embodiments, the one or more live biological cells are diseased cells.

At block 1202, an exemplary system (e.g., one or more electronic devices) obtains a first set of one or more images capturing the cell culture at a first time point. The first set of one or more images is captured at a first time point without destroying the one or more live biological cells. The images can be generated in a manner similar to FIG. 1 (102), FIG. 4 (402), FIG. 5B (506), or FIG. 9 (902). In some embodiments, the first set of one or more images comprises phase images. In some embodiments, the first set of one or more images is generated based on fluorescence images or autofluorescence images. In some embodiments, prior to obtaining the first set of one or more images, a perturbation is applied to the cell culture. In some embodiments, prior to obtaining the first set of one or more images, a therapeutic agent is applied to the cell culture. In some embodiments, prior to obtaining the first set of one or more images, a therapeutic agent and a perturbation are applied to the cell culture. In some embodiments, the perturbation and/or the therapeutic agent is a chemical treatment, a genetic treatment, or any combination thereof.

At block 1204, the system inputs the first set of one or more images into a trained machine-learning model to obtain a first set of embeddings representing positional and morphological characteristics in particular cellular substructures of the cell culture. In some embodiments, the trained machine-learning model is a self-supervised machine-learning model similar to the model described with reference to FIG. 1 (106), FIG. 2, and FIG. 5C (552). In some embodiments, the trained machine-learning model comprises a neural network. In some embodiments, it can be pre-trained using unlabeled images that do not depict biological samples. In some embodiments, the trained machine-learning model is configured to be retrained using unlabeled images of biological samples.

At block 1206, the system evaluates the characteristic of interest of the cell culture corresponding to the first time point based on the first set of embeddings to obtain a first set of one or more values. In some embodiments, the characteristic of interest is the proliferation (e.g., proliferation level) of the cell culture. In some embodiments, the characteristic of interest is the health (e.g., health level) of the cell culture. In some embodiments, the characteristic of interest is the development (e.g., development level) of the cell culture. It should be appreciated by one of ordinary skill in the art that the characteristic of interest can be any characteristic of the cell culture that can be reflected in cellular phenotypes, according to some embodiments.

Figure 13:
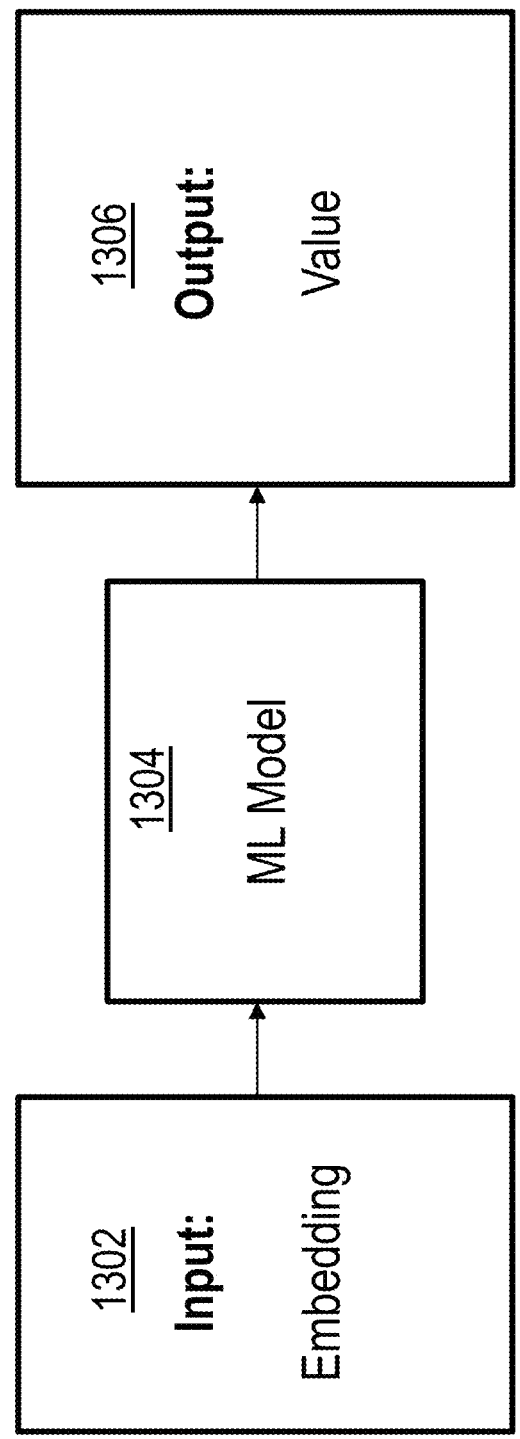
FIG. 13 illustrates an exemplary machine-learning model, in accordance with some embodiments.

In some embodiments, the evaluation of the characteristic of interest can be performed by a second machine-learning model. In some embodiments, the system can input the first set of embeddings into the second machine-learning model to obtain the one or more values indicative of the characteristic of interest. FIG. 13 illustrates an exemplary second machine-learning model, in accordance with some embodiments. The system inputs an embedding 1302 (e.g., obtained in block 1204 of FIG. 12) into a trained machine-learning model 1304 to obtain a value 1306 indicative of the characteristic of interest. In some embodiments, the machine-learning model 1304 is a linear regression classifier. For example, the machine-learning model can be a linear regression classifier configured to receive an embedding and output an estimated proliferation level. As another example, the machine-learning model can be a regression classifier, such as a linear regression classifier or a logistic regression classifier, configured to receive an embedding and output an estimated health level.

In some embodiments, the model 1304 can receive a plurality of embeddings corresponding to the first time point and output a plurality of values indicative of the characteristic of interest corresponding to the first time point (e.g., a plurality of estimated proliferation levels). The plurality of values can be aggregated (e.g., averaged) to obtain a single value (e.g., a single proliferation level) indicative of the characteristic of interest corresponding to the first time point. In some embodiments, the model 1304 can receive a plurality of embeddings corresponding to the first time point and directly output a single value or value range indicative of the characteristic of interest corresponding to the first time point (e.g., a single proliferation level).

Figure 14:
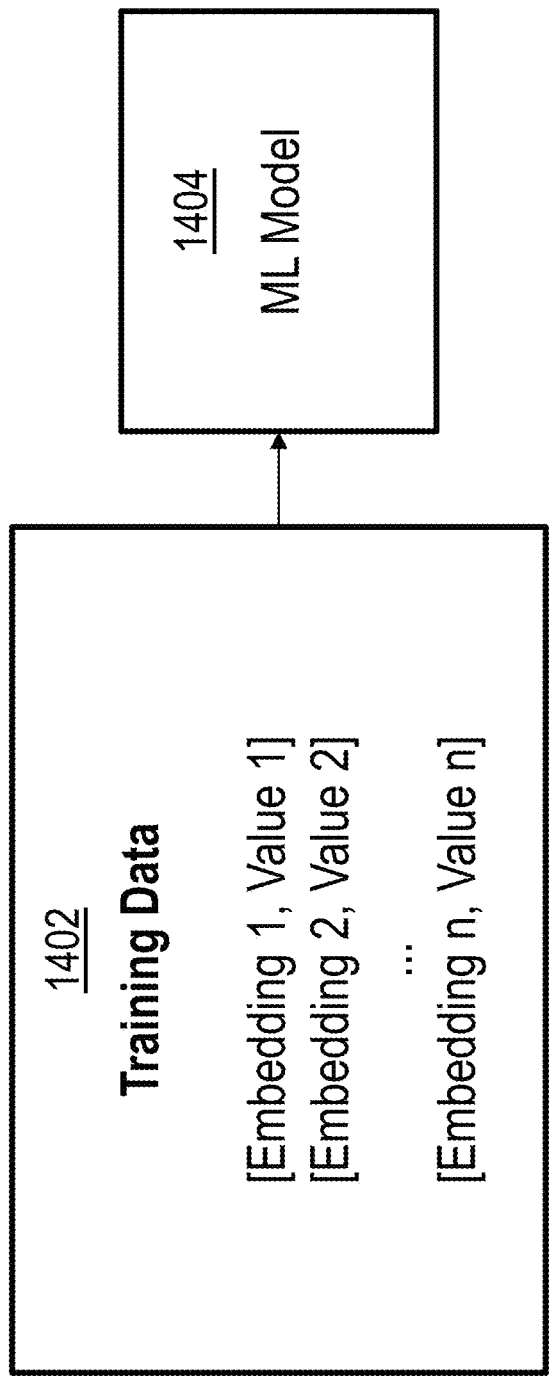
FIG. 14 illustrates an exemplary process of training the machine-learning model of FIG. 13, in accordance with some embodiments.

FIG. 14 illustrates an exemplary process of training the machine-learning model 1304 of FIG. 13, in accordance with some embodiments. As shown, training data 1402 comprises a plurality of data pairs. Each data pair comprises an embedding and a corresponding label. For example, the embedding can correspond to an image of a cell culture and the label can be the known proliferation level of the imaged cell culture. As another example, the embedding can correspond to an image of a cell culture and the label can be the known health level of the imaged cell culture. Machine learning model 1404 can be trained or fitted using the training data accordingly. In some embodiments, machine learning model 1404 may be the same or similar to machine learning model 1304 of FIG. 13.

In some embodiments, the system can evaluate the characteristic of interest by directly analyzing the images. The system may use image recognition to identify positional and morphological characteristics of cells or cellular substructure within the cell culture. In some embodiments, the system evaluates the image to identify a proliferation level (e.g., the number of cells in an image). For example, the system may evaluate the cell proliferation level by determining a first cell count to obtain the cell proliferation level corresponding to the first time point, and determining a second cell count to obtain the cell proliferation level corresponding to the second time point. Alternatively, the characteristic of interest may be directly analyzed in the image by an individual. In some embodiments, the individual is a human, such as any human with expertise in analyzing images of live biological cells (e.g., a trained pathologist). In some embodiments, the individual labels the images, such as by annotating the images, with the characteristic of interest.

Turning back to FIG. 12, at block 1208, the system obtains a second set of one or more images capturing the cell culture at a second time point later than the first time point. For example, the first time point may be captured at Hour 1 and the second time point may be captured at Hour 2, the first time point may be captured at Hour 1 and the second time point may be captured at Hour 10, or the first time point may be captured at Hour 1 and the second time point may be captured at Hour 24. In some embodiments, the second time point is captured 45 minutes after the first time point. The second set of one or more images is captured at a second time point without destroying the one or more live biological cells. The images can be generated in a manner similar to FIG. 1 (102), FIG. 4 (402), FIG. 5B (506), FIG. 9 (902), or FIG. 12 (1202). In some embodiments, the second set of one or more images comprises phase images. In some embodiments, the second set of one or more images is generated based on fluorescence images or autofluorescence images.

At block 1210, the system inputs the second set of one or more images into the trained machine-learning model to obtain a second set of embeddings representing positional and morphological characteristics in particular cellular substructures of the cell culture. The machine-learning model can be the same model used in block 1204.

At block 1212, the system evaluates the characteristic of interest of the cell culture corresponding to the second time point based on the second set of embeddings to obtain a second set of one or more values. For example, if the characteristic of interest is proliferation of the cell culture, the system can evaluate the proliferation level corresponding to the second time in a manner similar to block 1206.

At block 1214 the system determines, from the first set of one or more values and the second set of one or more values, a change of the characteristic of interest in the cell culture.

In some embodiments, the characteristic of interest is the cell proliferation of the cell culture. For example, the first set of one or more values obtained in block 1206 can indicate a predicted first cell proliferation level, and the second set of one or more values obtained in block 1212 can indicate a predicted second cell proliferation level. A rate (e.g., change) of the proliferation of the cell culture is determined from the predicted first cell proliferation level and the predicted second cell proliferation level. As used herein, the term "proliferation" can refer to the reproduction of cells in a cell culture (e.g., cell growth). A "proliferation level" can be the amount of cells in a cell culture at a specified time point, such as a cell count at a specified time point. In some embodiments, the method further comprises determining the in vitro (e.g., the viability of the cells in the laboratory) and/or metabolic fitness (e.g., the energy consumption and generation of specific metabolites) of the cell culture based on the predicted first cell proliferation level and the predicted second cell proliferation level. For example, a cell culture, such as a culture of iPSCs or differentiated cells, derived from specific patients may be studied using a machine-learning method provided herein. Certain inferences, including but not limited to the metabolic rate of the cells in vitro, may be made from evaluating the characteristic of interest in the cell culture (e.g., the cell proliferation of the cell culture), and can be imputed back to the patient.

The system can compare the rate of proliferation to a predefined threshold. In some embodiments, the predefined threshold is determined based on a known proliferation rate of the cells of the cell culture. The system may determine whether the rate of proliferation of the cell culture exceeds the predefined threshold and make a decision based on said determination. For example, if the rate of proliferation exceeds the predefined threshold the system can determine if the rate of proliferation is an abnormal proliferation rate. In some embodiments, if the rate of proliferation is determined to be abnormal, the growth of the cell culture is terminated before a predefined endpoint of cell growth. An abnormal proliferation rate may result from contamination of a cell culture, such as with fungi, bacteria, and/or cells of a different type (e.g., cancerous cells contaminating a healthy cell line). In some embodiments, the system determines that the rate of proliferation is an abnormal proliferation rate and prompts a user to provide one or more user inputs about the abnormal proliferation rate. In some embodiments, the user inputs may comprise instructing the system to terminate growth of the cell culture before a predefined endpoint of cell growth. In some embodiments, the user is an individual, such as a human with expertise in evaluating cell cultures. In some embodiments, the system determines that the rate of proliferation is an abnormal proliferation rate and is configured to automatically (e.g., robotically) terminate growth of the cell culture before a predefined endpoint of cell growth. Therefore, in some embodiments, the system is fully automated.

In some embodiments, the system may predict the confluence (e.g., the surface area coverage of cells on a cell culture plate) of the cell culture for a third time point based on the rate of proliferation of the cell culture. The third time point may be after the second time point. For example, the second time point may be at Hour 2 and the third time point may be any time after Hour 2, such as Hour 3, Hour 5, Hour 10, Hour 24, etc. The confluence of a cell culture may be used to determine timing for passaging of the cell culture. Appropriately passaging a cell culture, e.g., the timing for passaging the cell culture, is crucial for maintaining cell viability in vitro. In some embodiments, the system determines timing for passaging of the cell culture based on the predicted confluence of the cell culture. In some embodiments, the system determines timing for passaging of the cell culture based on the rate of proliferation.

In some embodiments, the system may generate a time trend based on the predicted first cell proliferation level and the predicted second cell proliferation level. The embeddings of the cell culture biological cells are provided to a classifier (e.g., the second machine learning model) to obtain the corresponding proliferation rate. In some embodiments, the classifier is configured to receive an embedding and output a predicted proliferation level value. The predicted proliferation levels for the cell culture are plotted to obtain time trend, which may be used to determine the proliferation rate. The determined rate of proliferation can provide information regarding cell culture health, as described herein.

In some embodiments, the characteristic of interest is the health of the cell culture. The first set of one or more values obtained in block 1206 indicates a predicted first cell health level. The second set of one or more values obtained in block 1212 indicates a predicted second cell health level. A change of the health of the cell culture is determined from the predicted first cell health level and the predicted second cell health level.

In some embodiments, the characteristic of interest is the development of the cell culture. The first set of one or more values obtained in block 1206 indicates a predicted first cell development level. The second set of one or more values obtained in block 1212 indicates a predicted second cell development level. A change of the development of the cell culture is determined from the predicted first cell development level and the predicted second cell development level. In some embodiments, the development of the cell culture comprises the differentiation of the cell culture, such as differentiation from stem cells to mature cell.

Figure 15:
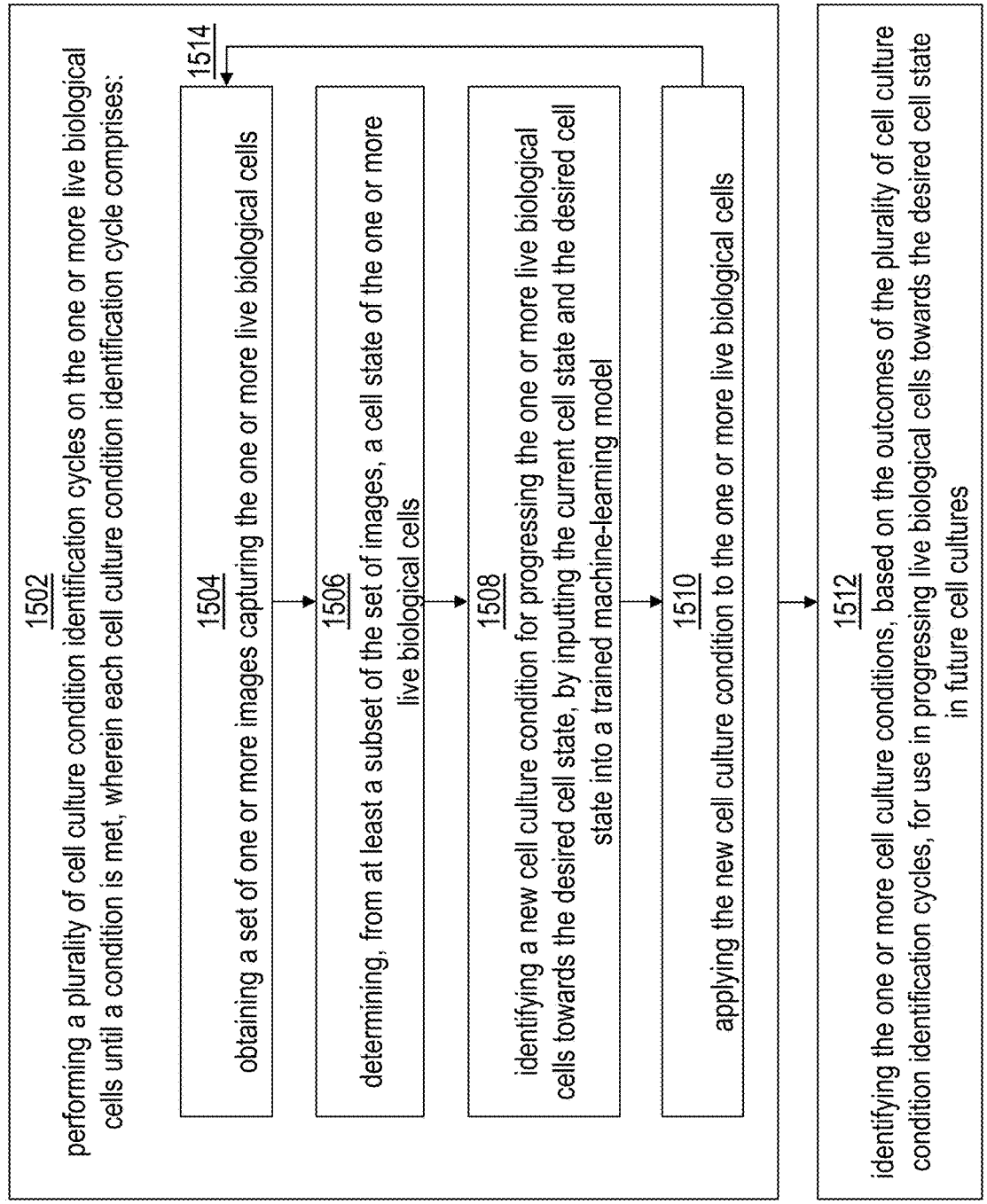
FIG. 15 illustrates an exemplary process for identifying one or more cell culture conditions for progressing one or more live biological cells towards a desired cell state, in accordance with some embodiments.

FIG. 15 illustrates an exemplary process for identifying one or more cell culture conditions for progressing one or more live biological cells towards a desired cell state, in accordance with some embodiments. Process 1500 is performed, for example, using one or more electronic devices implementing a software platform. In some examples, process 1500 is performed using one or more electronic devices. In some embodiments, process 1500 is performed using a client-server system, and the blocks of process 1500 are divided up in any manner between the server and one or more client devices. Thus, while portions of process 1500 are described herein as being performed by particular devices, it will be appreciated that process 1500 is not so limited. In process 1500, some blocks are, optionally, combined, the order of some blocks is, optionally, changed, and some blocks are, optionally, omitted. In some examples, additional steps may be performed in combination with the process 1500. Accordingly, the operations as illustrated (and described in greater detail below) are exemplary by nature and, as such, should not be viewed as limiting.

At block 1502, an exemplary system (e.g., one or more electronic devices) performs a plurality of cell culture condition identification cycles on the same one or more live biological cells until a condition is met. In some embodiments, the condition is met when the desired cell state is achieved. In some embodiments, the one or more live biological cells are induced pluripotent stem cells (iPSCs), and the desired cell state is a non-pluripotent cell state. In some embodiments, the non-pluripotent cell state is a differentiated cell state. In some embodiments, the one or more live biological cells are healthy cells, and the desired cell state is a diseased cell state. In some embodiments, the one or more liver biological cells are diseased cells, and the desired cell state is a healthy cell state. In some embodiments, the condition is met when a predefined number of cell culture condition identification cycles are performed.

Each cell culture condition identification cycle (block 1502) comprises blocks 1504-1510. At block 1504, the system obtains a set of one or more images capturing the one or more live biological cells. The set of one or more images is captured without destroying the one or more live biological cells. The images can be generated in a manner similar to FIG. 1 (102), FIG. 4 (402), FIG. 5B (506), FIG. 9 (902), FIG. 12 (1202), or FIG. 12 (1208). In some embodiments, the one or more live biological cells are mammalian cells. In some embodiments, the set of one or more images comprises phase images. In some embodiments, the set of one or more images is generated based on fluorescence images or autofluorescence images.

Figure 16:
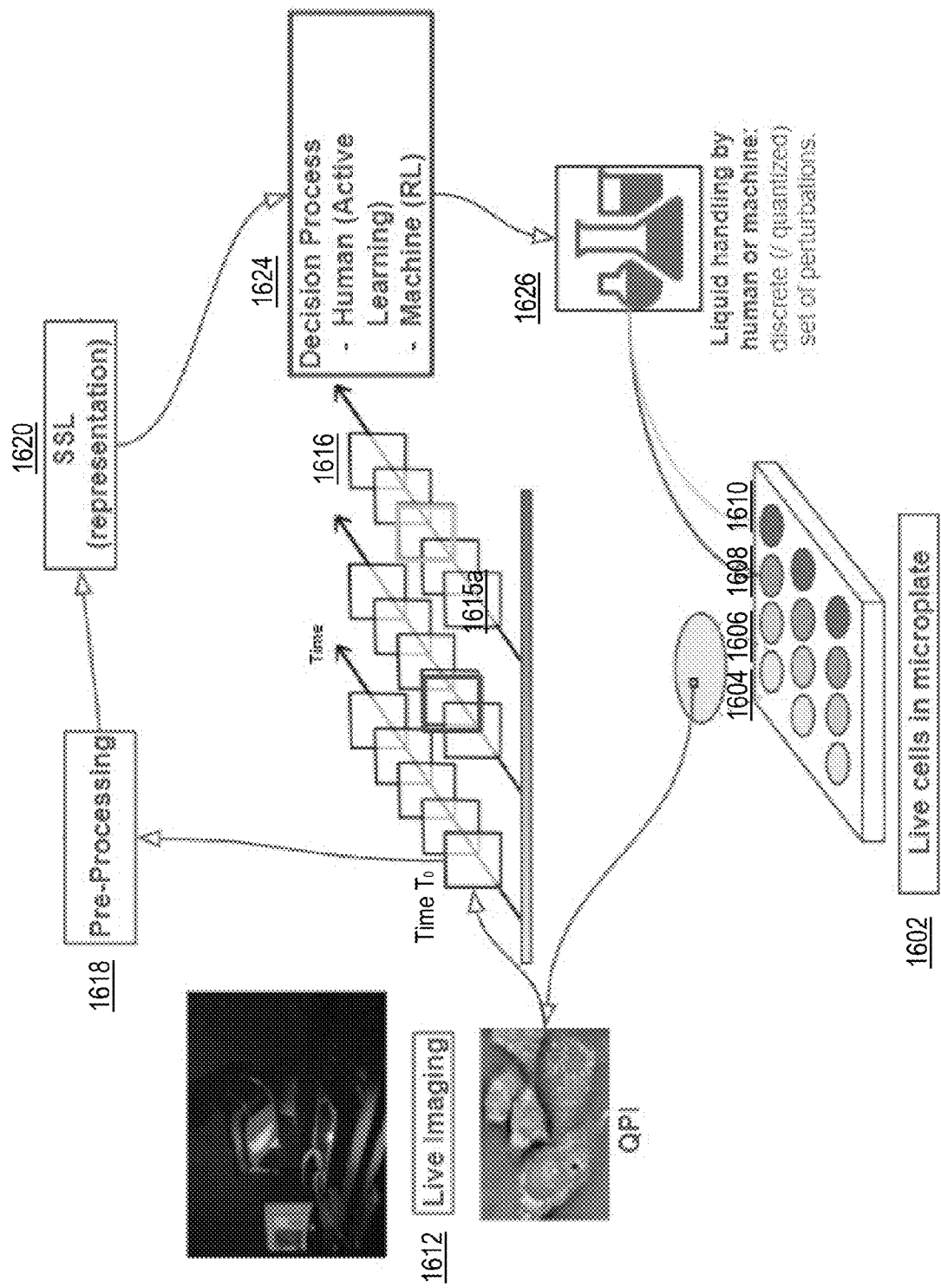
FIG. 16 illustrates an exemplary process for identifying one or more cell culture conditions for progressing one or more live biological cells towards a desired cell state, in accordance with some embodiments.

FIG. 16 illustrates an exemplary process of 1500, in accordance with some embodiments. With reference to step 1602, one or more live biological cells can be cultured in one or more wells 1610 of a microplate for continuous imaging. In some embodiments, other wells in the microplate can be used to culture cells (e.g., the same type of cells, different types of cells) such that multiple instances of process 1500 can be performed simultaneously. For example, wells 1604, 1606, and 1608 can be used to culture cells with different cell culture conditions such that three instances of process 1500 can be performed simultaneously in the same multi-well plate. In some embodiments, the different cell culture conditions comprise cell culture medium ingredient differences, cell culture temperature differences, cell culture pressure exposure differences, and/or cell culture light exposure differences. In some embodiments, wells 1604, 1606, and 1608 can be used to culture cells with the cell culture conditions (e.g., biological replicates) such that three instances of process 1500 can be performed simultaneously in the same multi-well plate. Each instance of process 1500 may occur in each of wells 1604, 1606, and 1608, and can yield one or more cell culture conditions.

With reference to step 1612 in FIG. 16, the wells can be imaged using QPI techniques to obtain phase images. In some embodiments, the system uses low photo-toxicity fluorescence and autofluorescence multi-spectral imaging techniques to obtain fluorescence images and/or autofluorescence images of the live biological cells. In some embodiments, the system can capture a combination of phase images, fluorescence images, and/or autofluorescence images at a given time. As shown, the system can obtain one or more images 1616 capturing live biological cells in wells 1610 at time point $T_0$, including image 1615a. The imaging techniques used do not cause destruction of the imaged live biological cells. Accordingly, the live biological cells in the various wells can be continuously imaged and monitored over time.

With reference to step 1618 in FIG. 16, the system can perform pre-processing on some or all of the live cell images. In some embodiments, the preprocessing comprises performing segmentation on the live cell images (e.g., cell detection, nucleus detection). In some embodiments, the system performs quality control on the live cell images to obtain quality control measures, which can be used to remove artifacts, determine which live cell images are used for downstream processing, etc. In some embodiments, the system can input the images (e.g., fluorescence images and/or autofluorescence images) into a machine-learning model configured to transform images of a first modality into images of a second modality (e.g., phase images). In some embodiments, the machine-learning model is a generative adversarial network model comprising a discriminator and a generator, and can be trained using ground truth phase images, fluorescence images, and autofluorescence images. In some embodiments, the images of live biological cells (e.g., phase images, fluorescence images, autofluorescence images, etc.) are captured using a microscope according to an optical setup. The optical setup can include an illumination pattern for illuminating the live biological cells. In some embodiments, the illumination pattern can be determined dynamically during the process 1500. Additional information of the image transformation model and the identification of the optical setup can be found in U.S. application Ser. No. 17/480,047 titled "BIOLOGICAL IMAGE TRANSFORMATION USING MACHINE-LEARNING MODELS," which issued as U.S. Pat. No. 11,423,256 on Aug. 23, 2022, and which is incorporated herein by reference in its entirety.

In some embodiments, the system uses various phase imaging optical techniques (e.g., QPC, Quadriwave lateral shearing interferometry, spatial light modulator or SLM) to reduce known aberrations and retrieve ground truth quantitative phase information. In some embodiments, the system uses a set of commercially available live cell compatible dyes (or reporter lines) for fast determination of cell stress (e.g., apoptosis, necrosis, position in cell cycle, mitochondrial and ER stress, etc.).

Turning back to FIG. 15, at block 1506, the system determines, from at least a subset of the set of images, a cell state of the one or more live biological cells. In some embodiments, the cell state is determined using active learning. For example, under the active-learning paradigm, the system may prompt a user to provide one or more user inputs about the state of the one or more live biological cells (e.g., after reviewing the images of live cells). In some embodiments, the user is an individual. In some embodiments, the cell state is determined by the system without user inputs. For example, the set of images can be automatically analyzed by the system to determine the cell state.

In the depicted example in FIG. 16, the image 1615a can be presented to a user and the user can provide an input about the cell state depicted in the image 1615a at step 1624. Alternatively, the image 1615a can be inputted into a self-supervised machine learning model as described herein in step 1620 to obtain an embedding (i.e., a vector) representing the image in a latent space. The embedding can be analyzed (e.g., using a machine-learning model) to determine the cell state.

Turning back to FIG. 15, at block 1508, a new cell culture condition is identified for progressing the one or more live biological cells towards the desired cell state, by inputting the current cell state and the desired cell state into a trained machine-learning model.

FIG. 17A depicts an exemplary method for training the machine-learning model of process 1500, in accordance with some embodiments. The machine-learning model 1708 is configured to receive at 1706 a cell state at the current iteration (i.e., iteration n) and a desired cell state, and output at 1710 a new cell culture condition for progressing the cells from the current state to the desired state. In some embodiments, the new cell culture condition is a perturbagen. In some embodiments, the perturbagen is a chemical treatment, a genetic treatment, or any combination thereof. In some embodiments, the perturbagen is an endoplasmic reticulum (ER) embodiments, the outputted condition may be selected from one of known conditions. In some embodiments, the outputted condition may be selected from one of conditions previously applied in the process.

Turning back to FIG. 15, at block 1510, the system applies the new cell culture condition to the one or more live biological cells. In the depicted example in FIG. 16, the new cell culture condition may be applied to wells 1610 at step 1626. In some embodiments, the application of the new type of cell culture condition to the one or more live biological cells is automated by one or more electronic devices (e.g., robotic devices). In some embodiments, the applying the new type of cell culture condition to the one or more live biological cells is performed by a user. In some embodiments, the user is an individual.

As shown by arrow 1514 in FIG. 15, multiple cell culture condition identification cycles can be performed. Each cycle comprises steps 1504-1510. In each cell culture condition identification cycle, the system obtains a set of one or more images capturing the one or more live biological cells at 1504. The system then determines, from at least a subset of the set of images, a cell state of the one or more live biological cells at 1506. A new cell culture condition is then identified for progressing the one or more live biological cells towards the desired cell state, by inputting the current cell state and the desired cell state into a trained machine-learning model at 1508. Finally, the system applies the new cell culture condition to the one or more live biological cells at 1510.

In some embodiments, the machine-learning model for identifying one or more cell culture conditions is continuously updated. FIG. 17B illustrates an exemplary method for continuously updating the machine-learning model of process 1500, in accordance with some embodiments. In FIG. 17B, at iteration n+1, the system can retrain the machine-learning model 1708 using training data 1718. The training data comprises an initial cell state (i.e., the cell state determined in block 1506 at iteration n), a new cell state (i.e., the cell state determined in block 1506 at iteration n+1), and the condition applied in iteration n. Accordingly, the model can be continuously trained in its capability to identify new cell culture conditions to push the cells of the cell culture to the desired state.

Turning back to FIG. 15, at block 1512 one or more cell culture conditions are identified, based on the outcomes of the plurality of cell culture condition identification cycles shown by arrow 1514, for use in progressing live biological cells towards the desired cell state in future cell cultures. By performing a plurality of cell culture condition identification cycles on the one or more live biological cells, the system enables the optimization of cell culture conditions for pushing the cells towards a desired cell state.

In some embodiments, a system may be designed to capture images of neurological cells to model a progression of a neurological disease of interest (e.g., ALS). In some embodiments, the system may include lines of neurological cells having the same, or substantially similar, genetic background. For example, the neurological cells may be induced pluripotent stem cells (iPSC) derived motor neurons (hNIL). In some embodiments, the system may include lines of neurological cells having different genetic backgrounds. In some embodiments, the lines of neurological cells may include two or more lines of neurological cells, three or more lines of neurological cells, four or more lines of neurological cells, five or more lines of neurological cells, or other quantities.

In some embodiments, the presence of certain binding proteins in neurological cells (e.g., neural cells) may be an indicator of neurotoxicity associated with one or more neurological diseases, such as amyotrophic lateral sclerosis (ALS) or tubular sclerosis complex (TSC). For example, detection of the binding protein TDP43 in neural cells (e.g., neurites) has been determined to be highly correlated with modified neurological activity in patients with ALS. Furthermore, as is well known in the art, the presence of TDP43 in the cell cytoplasm may also be an indicator of ALS. For example, mis-localization of TDP43 to the neurites (e.g., a dendrite or an axon) may be highly correlated with neurotoxicity in ALS patients. As such, it is anticipated that reduction of the neurological activity issues caused by the presence of the binding protein in neurites can increase the survival rate of ALS patients. In some embodiments, the present disclosure is directed to methods that enable downstream genetic and/or chemical screens to detect and/or test genetic alterations or chemical compounds capable of altering the pathological effects of TDP43 (i.e., mis-localization of TDP43), and thereby increase patient survival rate. In some embodiments, to model the behavior of neurological cells having TDP43, one or more neurological cell lines can be examined. For example, a cell line of healthy neurological cells (e.g., wild type (WT)), a cell line of neurological cells engineered with an overexpression of a modified binding protein (e.g., neurological cells engineered with an overexpression of a modified TDP43 such as, OE-TDP43ΔNLS: truncated nuclear localization signal (NLS), optionally containing h mApple fluorescent tag) (as is well known in the art, NLS comprises a nuclear localization tag and truncation of that tag causes TDP43 to mis-localize to the cytoplasm), a cell line of neurological cells engineered with an overexpress of the wild type binding protein (e.g., OE-TDP43: neurological cells engineered with an overexpression of wild type TDP43 (and optionally containing mApple fluorescent tag), or other lines of neurological cells can be modeled. These modeled neurological cell lines can be imaged regularly, for example, hourly, every 6 hours, every 12 hours, or daily, using QPC imaging techniques. At various chosen time periods, differentiation of the neurological cells may be performed. In some embodiments, the differentiation may be performed daily for 32 days, however more or fewer days of differentiation may be used. After the differentiation steps are performed (e.g., after 32 days), a check point analysis (e.g., via imaging) may be used to detect the TDP43 (e.g., via the presence of a fluorescent tag).

In some embodiments, specific gene mutations, such as the C9orf72 hexanucleotide repeat expansion, may also be used, and optionally modeled, as an indicator of neurological diseases like ALS. For example, it is known that approximately 40-50% of patients with a family history of ALS have the C9orf72 repeat expansion, and that approximately 5-10% of patients with sporadic ALS have the C9orf72 hexanucleotide repeat expansion. In some embodiments, the present disclosure is directed to methods that enable downstream genetic and/or chemical screens to detect and/or test genetic alterations or chemical compounds capable of altering the pathological effects associated with the presence of C9orf72 repeat expansion. In some embodiments, a system may be designed to capture images of neurological cells to model a progression of a neurological disease of interest (e.g., ALS) by examining the presence/absence of the C9orf72 repeat expansion. The neurological cells examined may be induced pluripotent stem cells (iPSC) derived motor neurons (hNIL). In some embodiments, to model the behavior of neurological cells having the presence/absence of the C9orf72 repeat expansion, one or more neurological cell lines can be examined. For example, modeled neurological cell lines may include a cell line of healthy neurological cells (e.g., wild type (WT)), a cell line of neurological cells engineered with the C9orf72 repeat expansion: C9_rep, or other lines of neurological cells. In some cases, for each of the different genetic backgrounds, the neurological cells may be engineered with the C9orf72 repeat expansion. These modeled neurological cell lines can be imaged regularly, for example, hourly, every 6 hours, every 12 hours, or daily, using QPC imaging techniques. At various chosen time periods, differentiation of the neurological cell lines may be performed. In some embodiments, the differentiation may be performed daily for 11 days, however more or fewer days of differentiation may be used. After the differentiation steps are performed (e.g., after 11 days), a check point analysis (e.g., via imaging) may be performed.

In some embodiments, the aforementioned techniques, such as processes 300, 900, 1200, and/or 1500 of FIGS. 3, 9, 12, and 15, respectively, may be used to model disease progression for neurological diseases, such as ALS or TSC. Modeling disease progression for neurological diseases may include capturing images of neurological cells and their substructures. In some embodiments, images of the neurological cells may be captured at different time periods (e.g., hourly, daily). In some embodiments, two different types of imaging may be performed: daily imaging and fast imaging. Daily imaging may use a camera having one or more light sources (e.g., an LED array) and one or more magnification levels (e.g., 5×, 10×, 20× magnifications). The regular imaging may acquire one or more raw images per field of view, and the raw images may be used to generate quantitative phase contrast (QPC) images. For example, four raw images may be acquired. Fast imaging may use a camera having one or more other light sources (e.g., a single LED) and one or more other magnification levels (e.g., 20×, 40×, and/or 60× total magnification). The fast imaging may acquire one or more raw images per field of view (e.g., one image). For example, one raw image may be captured using the fast imaging procedure.

Figure 19:
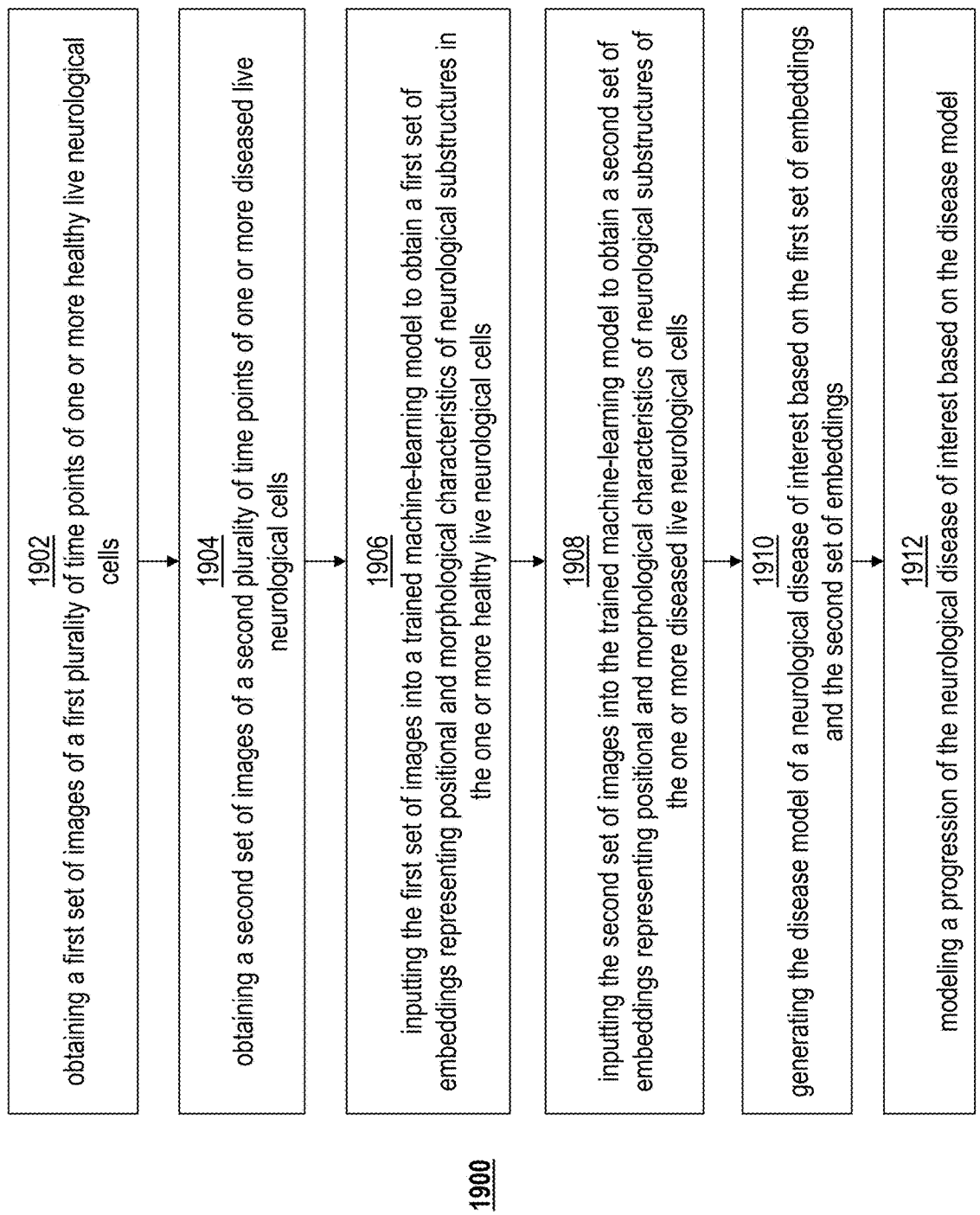
FIG. 19 illustrates an exemplary process for modeling a progression of a neurological disease of interest, in accordance with some embodiments.

FIG. 19 illustrates an exemplary process for modeling a progression of a neurological disease of interest, in accordance with some embodiments. Process 1900 is performed, for example, using one or more electronic devices implementing a software platform. In some examples, process 1900 is performed using one or more electronic devices. In some embodiments, process 1900 is performed using a client-server system, and the blocks of process 1900 are divided up in any manner between the server and one or more client devices. Thus, while portions of process 1900 are described herein as being performed by particular devices, it will be appreciated by one of skill in the art that process 1900 is not so limited. In process 1900, some blocks are, optionally, combined, the order of some blocks can, optionally, be changed, and some blocks are, optionally, omitted. In some examples, additional steps may be performed in combination with the process 1900. Accordingly, the operations as illustrated (and described in greater detail below) are exemplary by nature and, as such, should not be viewed as limiting.

At block 1902, an exemplary system (e.g., one or more electronic devices) may obtain a first set of images of a first plurality of time points of one or more healthy live neurological cells. In some embodiments, the first set of images may include phase images and QPC images. The imaging process may be performed in a same or similar manner as described in FIG. 4. For example, the healthy neurological cells may be imaged using QPI techniques to obtain phase images. In some embodiments, the system uses low phototoxicity fluorescence and autofluorescence multi spectral imaging techniques to obtain fluorescence images and/or autofluorescence images of the live biological cells. In some embodiments, the system can capture a combination of phase images, fluorescence images, and/or autofluorescence images at a given time.

As mentioned above, the system can obtain a plurality of images at a plurality of time points $T_0, T_1, \ldots,$ and $T_n$. The imaging techniques used do not cause destruction of the imaged live neurological cells. Accordingly, the healthy live neurological cells modeled in the various cell lines can be continuously imaged and monitored over time.

In some embodiments, the system uses various phase imaging optical techniques (e.g., QPC, Quadriwave lateral shearing interferometry, spatial light modulator or SLM) to reduce known aberrations and retrieve ground truth quantitative phase information. In some embodiments, the system uses a set of commercially available live cell compatible dyes (or reporter lines) for fast determination of cell stress (e.g., apoptosis, necrosis, position in cell cycle, mitochondrial and ER stress, etc.).

At block 1904, a second set of images of a second plurality of time points of one or more diseased live neurological cells may be obtained. In some embodiments, the diseased live neurological cells may correspond to live neurological cells engineered with an overexpression of modified TDP43, engineered with an overexpression of the wild type TDP43, live neurological cells of a first genetic background engineered with a C9orf72 repeat expansion, live neurological cells of a second genetic background engineered with a C9orf72 repeat expansion, or other forms of diseased neurological cells. In some embodiments, the second set of images may be captured using the same or similar image capturing steps described above with reference to block 1902.

At block 1906, the system may input the first set of images into a trained machine-learning model to obtain a first set of embeddings representing positional and morphological characteristics of neurological substructures in the one or more healthy live neurological cells. At block 1908, the system may input the second set of images into the trained machine-learning model to obtain a second set of embeddings representing positional and morphological characteristics of neurological substructures in the one or more diseased live neurological cells.

In some embodiments, the trained machine-learning model is a self-supervised machine-learning model similar to the model described with reference to FIG. 1 (106), FIG. 2, and FIG. 5C (552). In some embodiments, the trained machine-learning model comprises a neural network. In some embodiments, it can be pre-trained using unlabeled images that do not depict biological samples. In some embodiments, the trained machine-learning model is configured to be retrained using unlabeled images of biological samples. The model may employ a student-teacher framework as a backbone. One example of this backbone is the "self-Distillation with NO labels" or DINO framework.

In some embodiments, the trained machine-learning model may have the architecture of a convolutional neural network. For example, the ResNet-18 architecture can be used as the base framework. ResNet-18 includes 18 layers organized as four residual blocks. A residual block is one that applies an identity mapping: the input to one layer is also passed directly to another layer. In some embodiments, each residual block is connected to the next layer in the network as well as skipped layers further down the network. The connection between a residual block and a down-network layer is referred to as a shortcut or skip connection, which can bypass one or more layers. Mathematically, if the input x is the input to a layer and the output is F(x), then the output of the residual block can be expressed as $Y=F(x)+x$.

Figure 20C:
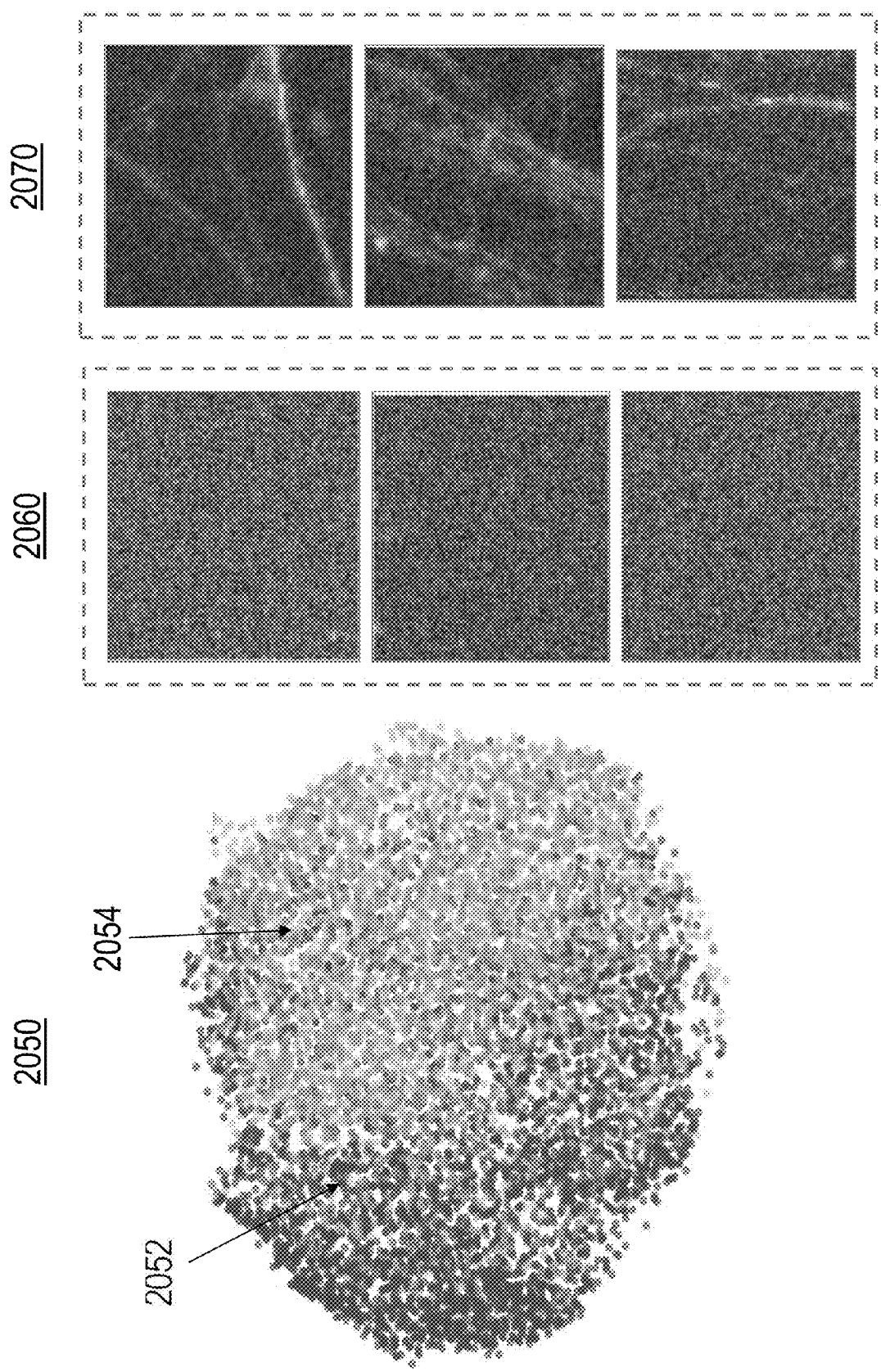

At block 1910, the system may generate a disease model of a neurological disease of interest based on the first set of embeddings and the second set of embeddings. In some embodiments, the disease model may be generated by mapping the first set of embeddings and the second set of embeddings into a topological space. For example, as seen in FIGS. 20A and 20C, UMAP 2000 and UMAP 2050 can be used to visualize the first set of embeddings of the second set of embeddings described above with respect to blocks 1906 and 1908. In UMAP 2000, embeddings 2002 may be representations of the first set of images (blue data points), while embeddings 2004 may be representations of the second set of images (yellow data points). In UMAP 2050, embeddings 2052 may be representations of the first set of images from OE-TDP43 cells (blue data points), while embeddings 2054 may be representations of the second set of images from OE-TDP43ΔNLS cells (yellow data points). In particular, UMAP 2000 may represent images of the soma (i.e., cell body) or soma region of neurological cells, whereas UMAP 2050 may represent images of neurites.

In some embodiments, the first set of images 2010 or 2060 depict one or more healthy live neurological cells (e.g., soma of neurons for images 2010 and neurites for images 2060) and the second set of images 2020 or 2070 depict the first sub-cellular structure in the one or more diseased live neurological cells (e.g., soma of neurons for images 2020 and neurites for images 2070). For example, the first set of images 2010, 2060 may refer to the images obtained at block 1902, and the second set of images 2020, 2070 may refer to images obtained at block 1904. In images 2010 and 2020, the blue portions represent the signal from the nucleus (DAPI), whereas the pink portions represent the TDP43 signal. For example, images 2010 may depict sub-cellular structures, such as a cell's nucleus and cytoplasm. As can be seen from FIG. 20A, images 2010 have the nuclear signal and the disease proxy signal co-localized. On the other hand, the disease proxy signal (e.g., the TDP43 signal) may have a greater and more disperse distribution in images 2020. In some embodiments, images 2060 may depict neurites with no TDP43 and images 2070 may depict neurites with TDP43. Images 2070 depict sub-cellular structures, such as axons, dendrites. These sub-cellular structures may not have a uniform distribution of TDP43 within each image tile.

FIG. 20B depicts a neighborhood cell density plot 2030 and a plot 2040 of a ratio of TDP43 in the nucleus to the cytoplasm. Plots 2030 and 2040 may be generated based on embeddings depicted in UMAP 2000. For example, the healthy live neurological cells may include healthy soma regions and the diseased live neurological cells may include diseased soma regions. In some embodiments, the system may determine a first abundance level of a disease signal in a nucleus of the diseased live neurological cells (e.g., of the nucleus within the soma region of the neurological cells). The system may also determine a second abundance level of the disease signal in cytoplasm of the diseased live neurological cells (e.g., from the cytoplasm within the soma region of the neurological cells). Neighborhood cell density plot 2030 may illustrate that the density the cells analyzed is uniform.

In some embodiments, the system may determine the first abundance level by determining an amount of a disease signal (e.g., TDP43) present in the nucleus of the diseased live neurological cells. The system may also determine the second abundance level by determining an amount of the disease signal (e.g., TDP43) present in the cytoplasm of the diseased live neurological cell (e.g., within the soma region of the neurological cell). In some embodiments, images 2020 may be used to determine the first and second abundance levels. For each of the diseased live neurological cells r, a disease infiltration value may be computed based on the first abundance level and the second abundance level. The disease infiltration value may represent a ratio of the first abundance level to the second abundance level. The lower the ratio of the first abundance level to the second abundance level, the greater the disease of interest (e.g., ALS) may have progressed in the patient, and vice versa.

In some embodiments, the computed disease infiltration value may be encoded into each embedding. For example, for a given embedding of UMAP 2000, the ratio of the abundance of the disease signal (e.g., TDP43) in the nucleus to the abundance of the disease signal in cytoplasm of the diseased live neurological cell (e.g., as determined in the soma or soma region). The system may generate a visualization, such as plot 2040, based on the encoded embeddings.

FIG. 20D depicts a neurite surface plot 2080 (normalized neurites surface area per image) and a plot 2090 of an accumulation of the disease signal (e.g., TDP43) in the neurons. Plots 2080 and 2090 may be generated based on embeddings depicted in UMAP 2050. For example, the healthy live neurological cells may include healthy live neurite regions and the diseased live neurological cells may include diseased live neurite regions. In some embodiments, the accumulation level may be determined by determining an amount of the disease signal present in a neurite of the one or more diseased live neurological cells (e.g., images 2070). For each diseased live neurite regions, a disease infiltration value may be computed based on the accumulation level. The greater the disease infiltration value is, the greater the disease of interest (e.g., ALS) may have progressed.

In some embodiments, the computed disease infiltration value may be encoded into each diseased live neurological cell's corresponding neurite region embeddings. The encoded embeddings may be used to generate a visualization, such as plot 2090.

In some embodiments, the soma and the neurite regions of cells may have different characteristics that the trained machine-learning model (e.g., DINO) may attach to. By independently modeling the soma and neurite regions, different phenotypic indicia of disease may be identified, allowing richer screening for disease signal infiltration in vivo. For example, for a given soma region phenotypic state across multiple neurological cells, different neurite characteristics across such neurological cells may provide a richer understanding of progression of the disease of interest in a patient (e.g. increase or decrease of neurites length).

At block 1912, a progression of the neurological disease of interest may be modeled based on the generated disease model. In some embodiments, the progression of the neurological disease of interest may be determined based on time-stamps associated with the first set of embeddings and the second set of embeddings. For example, each embedding may be encoded with temporal data indicating a time that the image represented by the embedding was captured. The change in position and morphology of each imaged cell may be used to determine how the disease has progressed. The visualizations of FIGS. 20A-20D may be derived from in vitro images captured after a differentiation time period has ended. For example, the in vitro images used to derive the embeddings of UMAP 2000 or 2050 may correspond to images captured after 32 days of differentiation.

Figure 21:
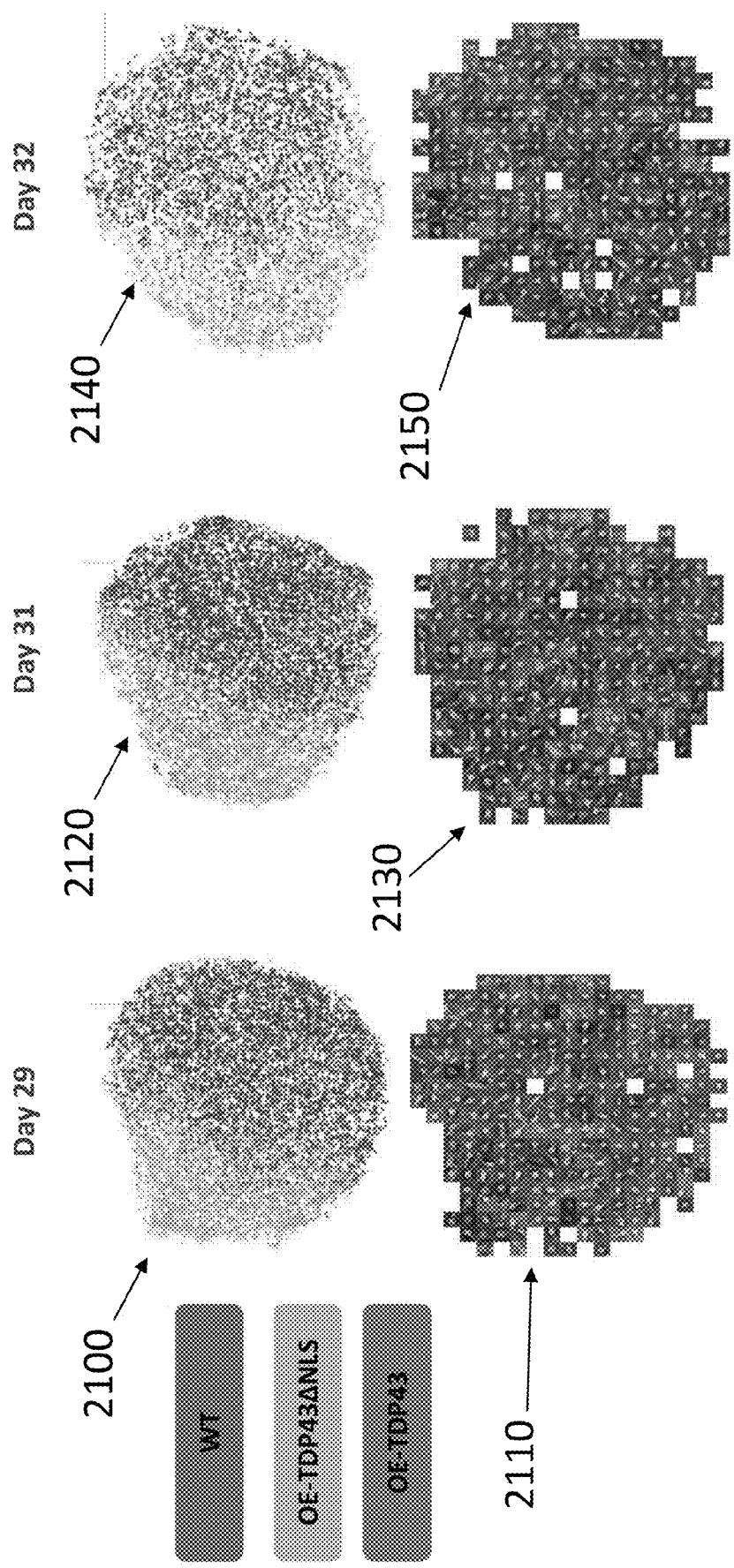
FIG. 21 illustrate visualizations of embeddings derived from images of neurological cells and phase images of the neurological cells over different amounts of differentiation have been performed, in accordance with some embodiments.
Figure 23D:
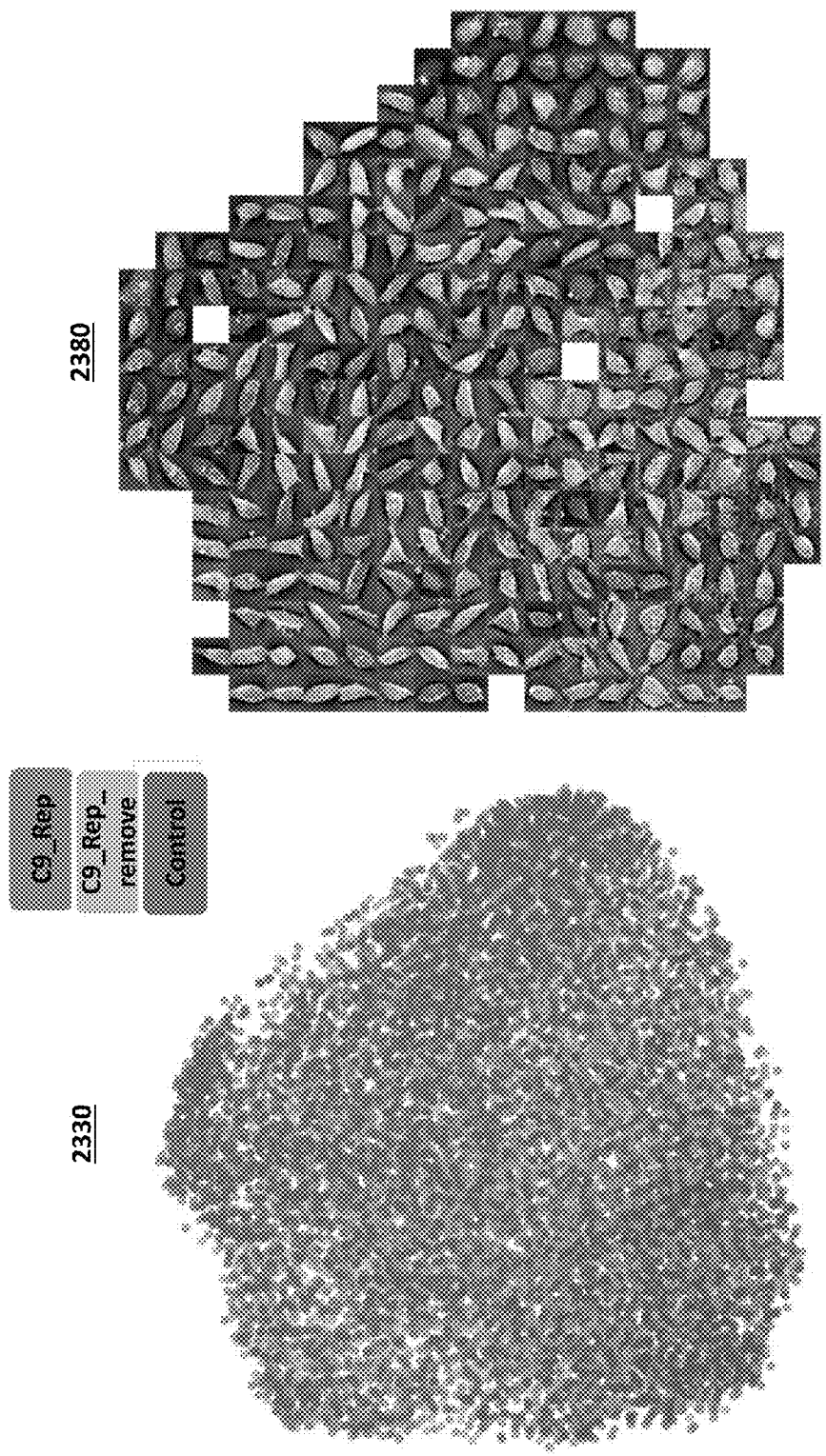

The disease progression described at block 1912 may be visualized, for example, with reference to FIG. 21. In FIG. 21, UMAPs 2100, 2120, and 2140 may depict embeddings derived from in-vitro images of neurological cells captured after 29 days of differentiation, 31 days of differentiation, and 32 days of differentiation, respectively. In UMAPs 2100, 2120, and 2140, the green data points may refer to embeddings representing healthy neurological cells (e.g., wild type), the blue data points may refer to embeddings representing healthy neurological cells engineered with an overexpression of TDP43 (e.g., wild type), and the yellow data points refer to embeddings representing diseased neurological cells engineered with an overexpression of TDP43ΔNLS.

Each of UMAPs 2100, 2120, and 2140 may have a corresponding phase image plot 2110, 2130, and 2150, respectively. Embeddings of UMAPs 2100, 2120, and 2140 may have a one-to-one correspondence with phase images of plots 2110, 2130, and 2150. As can be seen from FIG. 21, the neurological cells die off as time progresses resulting in a weaker signal. Furthermore, the WT neurological cells and the OE-TDP43 neurological cells may be co-localized, while the OE-TSP43ΔNLS neurological cells occupy a separate region of UMAPs 2100, 2120, and 2140. The co-localization of these neurological cells may be substantially consistent as differentiation is performed.

FIG. 22 illustrates phase images and filtered images of neurological cells captured at a single time point using fast imaging techniques, in accordance with various embodiments. The fast QPC imaging may allow the movement of objects (e.g., large molecular structures) inside the cells to be detected and observed over time from a plurality of images captured over time. In some embodiments, the images may be captured at time intervals between 10 ms and 1000 ms, at time intervals between 50 ms and 500 ms or at time intervals of 100 ms. Different objects (or large molecular structures) can move at different speeds along the neurites, and so neurotoxicity of the cells can be detected based on the movement and/or speed of movement of these objects or molecules inside the neurites. In particular, image 2200 may depict a phase image of a healthy cell (wild type) and image 2210 may depict a filtered version of image 2200, extracted from a video demonstrating the movement in the cell over time. Image 2220 may depict a phase image of a diseased (e.g., OE-TSP43ΔNSL) cell and image 2230 may depict a filtered version of image 2220.

In some embodiments, the images used to generate the embeddings may correspond to images of neurological cells presenting with a particular gene mutation associated with a disease of interest (e.g., ALS). For example, images of neurological cells of patients having the C9orf72 hexanucleotide repeat expansion may be captured. In some embodiments, the neurological cells may include healthy live neurological cells (e.g., wild type (WT)), diseased neurological cells of a first genetic background (e.g., engineered line with the C9orf72 repeat expansion: C9_rep), diseased neurological cells of a second genetic background (e.g., engineered line with the C9orf72 repeat expansion: C9_rep).

FIGS. 23A-23E depict visualizations 2300-2340 of embeddings derived from images of healthy neurological cells and diseased neurological cells having a gene mutation associated with a disease of interest. In some embodiments, each of visualizations 2300-2340 may be a UMAP of embeddings derived from images of neurological cells captured after different differentiation times. For example, visualization 2300 may represent a UMAP of embeddings derived from images of neurological cells after 0 days of differentiation; visualization 2310 may represent a UMAP of embeddings derived from images of neurological cells after 1 days of differentiation; visualization 2320 may represent a UMAP of embeddings derived from images of neurological cells after 2 days of differentiation; visualization 2330 may represent a UMAP of embeddings derived from images of neurological cells after 5 days of differentiation; and visualization 2340 may represent a UMAP of embeddings derived from images of neurological cells after 11 days of differentiation. Different differentiation times may be used and the aforementioned is merely exemplary. As seen in visualizations 2300-2340, the blue data points may refer to embeddings derived from images of neurological cells engineered with C9_rep; the yellow data points may refer to embeddings derived from images of neurological cells engineered with C9_rep_remove (which can remove the C9orf72 repeat expansion); and the green data points may refer to embeddings derived from images of healthy neurological cells (e.g., control).

Figure 24:
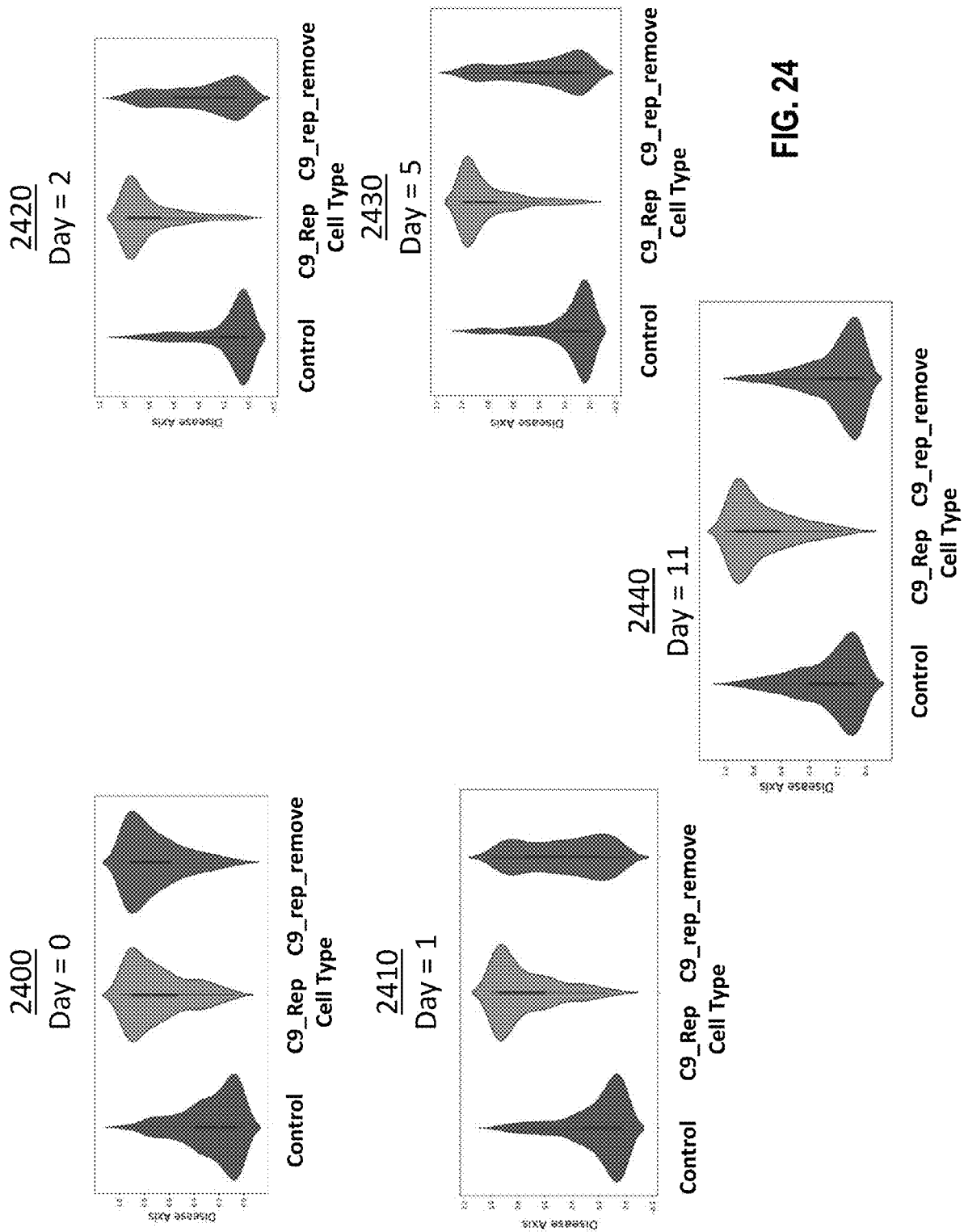
FIG. 24 illustrates visualizations of the morphological changes of neurological cells after different amounts of differentiation have been performed, in accordance with some embodiments.

FIGS. 23A-23E may also include visualizations 2350-2390. Each of visualizations 2350-2390 may include a phase image of a neurological cell. In some embodiments, each data point from visualizations 2300-2340 may have a corresponding phase image in visualizations 2350-2390. In some embodiments, there may be a one-to-one correspondence between visualizations 2300 and 2350, 2310 and 2360, 2320 and 2370, 2330 and 2380, and 2340 and 2390. In some embodiments, the morphological characteristics of the neurological cells may also change over the differentiation time period. As an example, with reference to FIG. 24, morphology plots 2400-2440 may depict a shape/formation of control neurological cells, C9_rep neurological cells, and C9_rep_remove neurological cells after different amounts of differentiation. For example, morphology plot 2400 may represent cell morphology after 0 days of differentiation, morphology plot 2410 may represent cell morphology after 1 days of differentiation, morphology plot 2420 may represent cell morphology after 2 days of differentiation, morphology plot 2430 may represent cell morphology after 5 days of differentiation, and morphology plot 2440 may represent cell morphology after 11 days of differentiation. As can be seen by visualizations 2400-2440, after the 11 days of differentiation, morphological characteristics of the control neurological cells may be the same or similar to the morphological characteristics of the C9_rep_remove neurological cells.

Figure 25A:
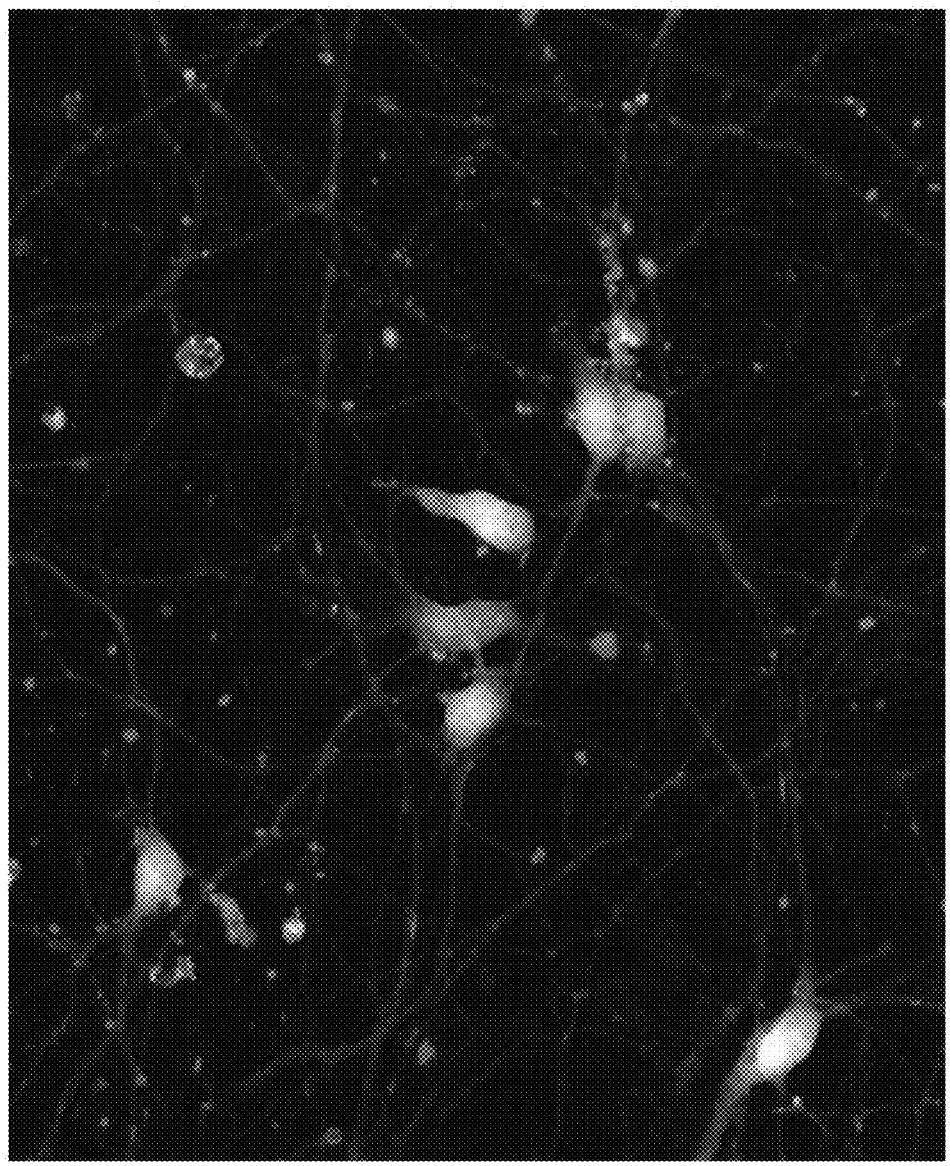
FIGS. 25A-25B illustrate phase images and filtered images of healthy neurological cells and diseased neurological cells, in accordance with some embodiments.
Figure 25B:
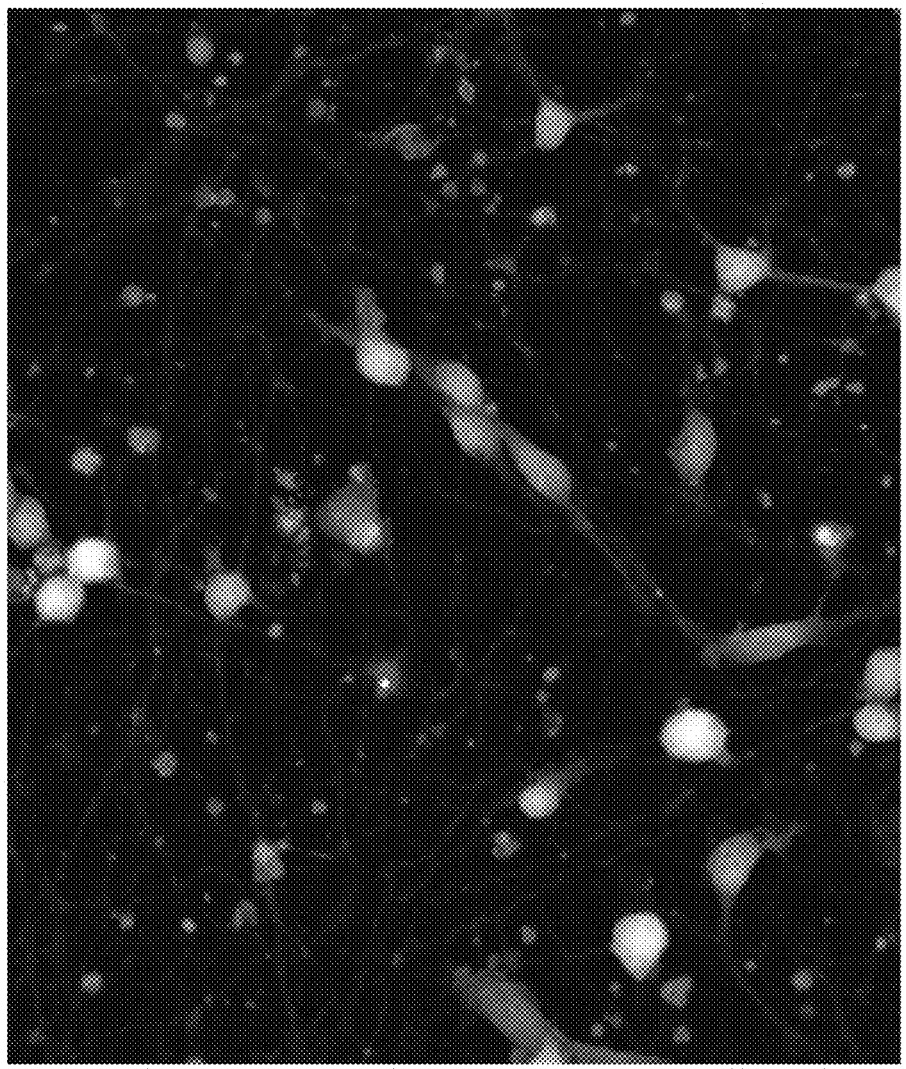

FIGS. 25A and 25B illustrate a phase image 2500 and a filtered image 2550 of neurological cells captured at a single time point using fast imaging techniques, in accordance with various embodiments. The fast QPC imaging may allow the movement of objects (e.g., large molecular structures) inside the cells to be detected and observed over time from a plurality of images captured over time. In some embodiments, the images may be captured at time intervals between 10 ms and 1000 ms, at time intervals between 50 ms and 500 ms or at time intervals of 100 ms. Different objects (or large molecular structures) can move at different speeds along the neurites, and so neurotoxicity of the cells can be detected based on the movement and/or speed of movement of these objects or molecules inside the neurites. Phase image 2500 may come from a wild type (WT) cell line. In the example of FIG. 25A, the trajectories of the object are long and smooth, indicating very limited blocking. Filtered image 2550 may come from a C9orf72 cell line. In the example of FIG. 25B, the trajectory of the objects is shorted. Some of the objects may be blocked at junctions and merged together, creating bigger structures.

FIG. 26 illustrates images 2600-2620 from a video depicting movement of objects within neurological cells, in accordance with various embodiments. Images 2600-2620 depict the motion of an object, depicted by the red bounding box, over time. For example, image 2600 depicts an object at time T0, image 2610 depicts the object at time T5, and image 2620 depicts the object at time T10, where time T5=T0+500 ms, and time T10=T1+1000 ms.

The system provided herein improves upon the speed and cost of classical genetic and chemical screens, by incorporating the autonomous imaging modalities that may be continuously updated. Moreover, the system can be applied to the analyses various additional cellular processes, including cellular differentiation, cellular proliferation, disease modeling, and histopathology imaging, as described above, without destruction of the sample. Specifically, the system vastly improves on standard methods of studying biological processes by continuously modeling dynamic cellular process at rapid time and spatial frequencies.

The operations described herein are optionally implemented by components depicted in FIG. 18. FIG. 18 illustrates an example of a computing device in accordance with one embodiment. Device 1800 can be a host computer connected to a network. Device 1800 can be a client computer or a server. As shown in FIG. 18, device 1800 can be any suitable type of microprocessor-based device, such as a personal computer, workstation, server or handheld computing device (portable electronic device) such as a phone or tablet. The device can include, for example, one or more of processor 1810, input device 1820, output device 1830, storage 1840, and communication device 1860. Input device 1820 and output device 1830 can generally correspond to those described above, and can either be connectable or integrated with the computer.

Input device 1820 can be any suitable device that provides input, such as a touch screen, keyboard or keypad, mouse, or voice-recognition device. Output device 1830 can be any suitable device that provides output, such as a touch screen, haptics device, or speaker.

Storage 1840 can be any suitable device that provides storage, such as an electrical, magnetic or optical memory including a RAM, cache, hard drive, or removable storage disk. Communication device 1860 can include any suitable device capable of transmitting and receiving signals over a network, such as a network interface chip or device. The components of the computer can be connected in any suitable manner, such as via a physical bus or wirelessly.

Software 1850, which can be stored in storage 1840 and executed by processor 1810, can include, for example, the programming that embodies the functionality of the present disclosure (e.g., as embodied in the devices as described above).

Software 1850 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 1840, that can contain or store programming for use by or in connection with an instruction execution system, apparatus, or device.

Software 1850 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic or infrared wired or wireless propagation medium.

Device 1800 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 1800 can implement any operating system suitable for operating on the network. Software 1850 can be written in any suitable programming language, such as C, C++, Java or Python. In various embodiments, application software embodying the functionality of the present disclosure can be deployed in different configurations, such as in a client/server arrangement or through a Web browser as a Web-based application or Web service, for example.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Exemplary Embodiments

The following embodiments are exemplary and are not intended to limit the scope of the invention described herein.

Embodiment 1. A method of determining an impact of a therapeutic agent on diseased cells, comprising: obtaining a first plurality of images captured at a first plurality of time points of one or more untreated diseased live biological cells expressing a disease phenotype; obtaining a second plurality of images captured at a second plurality of time points of one or more treated diseased live biological cells expressing the disease phenotype that has been treated with the therapeutic agent; inputting the first plurality of images into a trained machine-learning model to obtain a first plurality of embeddings representing positional and morphological changes over time in particular cellular substructures of the one or more untreated diseased live biological cells; inputting the second plurality of images into the trained machine-learning model to obtain a second plurality of embeddings representing positional and morphological changes over time in particular cellular substructures of the one or more treated diseased live biological cells; and determining, from at least a subset of the first plurality of embeddings and the second plurality of embeddings, the impact of the therapeutic agent on the reversion of the one or more treated diseased cells from a diseased state.

Embodiment 2. The method of embodiment 1, further comprising: obtaining a third plurality of images captured at a third plurality of time points of one or more healthy live biological cells; inputting the third plurality of images into the trained machine-learning model to obtain a third plurality of embeddings representing positional and morphological changes over time in particular cellular substructures of the one or more healthy live biological cells; and determining, from at least a subset of the first plurality of embeddings, the second plurality of embeddings, and the third plurality of embeddings, the impact of the therapeutic agent on the reversion of the one or more treated cells from the diseased state to the healthy state.

Embodiment 3. The method of embodiment 2, wherein the one or more treated diseased live biological cells are a first set of treated diseased live biological cells and are treated with a first dosage of the therapeutic agent, the method further comprising: obtaining a fourth plurality of images captured at a fourth plurality of time points of a second set of treated diseased live biological cells expressing the disease phenotype that has been treated with a second dosage of the therapeutic agent; inputting the fourth plurality of images into the trained machine-learning model to obtain a fourth plurality of embeddings representing positional and morphological changes over time in particular cellular substructures of the second set of treated diseased live biological cells; and comparing the impact of the first dosage and the second dosage based on at least a subset of the first plurality of embeddings, the second plurality of embeddings, and the fourth plurality of embeddings.

Embodiment 4. The method of embodiment 3, wherein the one or more treated diseased live biological cells are a first set of treated diseased live biological cells and wherein the therapeutic agent is a first therapeutic agent, the method further comprising: obtaining a fifth plurality of images captured at a fifth plurality of time points of a third set of treated diseased cells expressing the disease phenotype that has been treated with a second therapeutic agent; inputting the fifth plurality of images into the trained machine-learning model to obtain a fifth plurality of embeddings representing positional and morphological changes over time in particular cellular substructures of the third set of treated diseased live biological cells; and comparing the impact of the first therapeutic agent and the second therapeutic agent based on at least a subset of the first plurality of embeddings, the second plurality of embeddings, and the fifth plurality of embeddings.

Embodiment 5. The method of any one of embodiments 1-4, wherein the first plurality of time points are the same as the second plurality of time points.

Embodiment 6. The method of any one of embodiments 1-4, wherein the first plurality of time points are different from the second plurality of time points.

Embodiment 7. The method of any one of embodiments 1-6, wherein the therapeutic agent is a chemical treatment, a genetic treatment, or any combination thereof.

Embodiment 8. The method of any one of embodiments 1-7, further comprising: determining one or more dose administration intervals for administering the therapeutic agent based on the second plurality of embeddings.

Embodiment 9. The method of any one of embodiments 1-8, further comprising: providing a medical recommendation or administering the therapeutic agent to a patient.

Embodiment 10. The method of any one of embodiments 1-9, wherein the first plurality of images and the second plurality of images comprise phase images.

Embodiment 11. The method of any one of embodiments 1-9, wherein the first plurality of images and the second plurality of images are generated from fluorescence images or autofluorescence images.

Embodiment 12. The method of any one of embodiments 1-11, wherein the trained machine-learning model is a self-supervised machine-learning model.

Embodiment 13. The method of any one of embodiments 1-12, wherein the trained machine-learning model is trained using unlabeled data.

Embodiment 14. The method of embodiment 13, wherein the trained machine-learning model is pre-trained using unlabeled images that do not depict biological samples.

Embodiment 15. The method of embodiment 14, wherein the trained machine-learning model is retrained using unlabeled images of biological samples.

Embodiment 16. The method of any one of embodiments 1-15, wherein evaluating the impact of the therapeutic agent comprises: inputting the first plurality of embeddings into a classifier to obtain a first plurality of disease scores; and inputting the second plurality of embeddings into the classifier to obtain a second plurality of disease scores.

Embodiment 17. The method of embodiment 16, further comprising: generating a first time trend based on the first plurality of disease scores; generating a second time trend based on the second plurality of disease scores; and comparing the first time trend and the second time trend.

Embodiment 18. The method of embodiment 16 or 17, further comprising: generating a first plurality of distributions based on the first plurality of disease scores; generating a second plurality of distributions based on the second plurality of disease scores; and comparing the first plurality of distributions and the second plurality of distributions.

Embodiment 19. The method of any one of embodiments 1-18, wherein the classifier is a logistic regression classifier.

Embodiment 20. A non-transitory computer-readable storage medium storing one or more programs for determining an impact of a therapeutic agent on diseased cells, the one or more programs comprising instructions, which when executed by one or more processors of an electronic device, cause the electronic device to: obtain a first plurality of images captured at a first plurality of time points of one or more untreated diseased live biological cells expressing a disease phenotype; obtain a second plurality of images captured at a second plurality of time points of one or more treated diseased live biological cells expressing the disease phenotype that has been treated with the therapeutic agent; input the first plurality of images into a trained machine-learning model to obtain a first plurality of embeddings representing positional and morphological changes over time in particular cellular substructures of the one or more untreated diseased live biological cells; input the second plurality of images into the trained machine-learning model to obtain a second plurality of embeddings representing positional and morphological changes over time in particular cellular substructures of the one or more treated diseased live biological cells; and determine, from at least a subset of the first plurality of embeddings and the second plurality of embeddings, the impact of the therapeutic agent on the reversion of the one or more treated diseased cells from a diseased state.

Embodiment 21. A system for determining an impact of a therapeutic agent on diseased cells, comprising: one or more processors; a memory; and one or more programs, wherein the one or more programs are stored in the memory and configured to be executed by the one or more processors, the one or more programs including instructions for: obtaining a first plurality of images captured at a first plurality of time points of one or more untreated diseased live biological cells expressing a disease phenotype; obtaining a second plurality of images captured at a second plurality of time points of one or more treated diseased live biological cells expressing the disease phenotype that has been treated with the therapeutic agent; inputting the first plurality of images into a trained machine-learning model to obtain a first plurality of embeddings representing positional and morphological changes over time in particular cellular substructures of the one or more untreated diseased live biological cells; inputting the second plurality of images into the trained machine-learning model to obtain a second plurality of embeddings representing positional and morphological changes over time in particular cellular substructures of the one or more treated diseased live biological cells; and determining, from at least a subset of the first plurality of embeddings and the second plurality of embeddings, the impact of the therapeutic agent on the reversion of the one or more treated diseased cells from a diseased state.

Embodiment 22. A method of modeling a progression of a disease of interest having a plurality of disease states, comprising: obtaining a first set of images captured at a first plurality of time points of a first non-zero concentration of diseased live biological cells expressing a first disease state of the disease; obtaining a second set of images captured at a first plurality of time points of a second non-zero concentration of diseased live biological cells expressing a second disease state of the disease; inputting the first set of images into a trained machine-learning model to obtain a first set of embeddings representing positional and morphological characteristics in particular cellular substructures of the first non-zero concentration of diseased live biological cells; inputting the second set of images into the trained machine-learning model to obtain a second set of embeddings representing positional and morphological characteristics in particular cellular substructures of the second non-zero concentration of diseased live biological cells; generating the disease model based on the first set of embeddings and the second set of embeddings; and modeling a progression of the disease based on the disease model.

Embodiment 23. The method of embodiment 22, wherein generating a disease model comprises: mapping the first set of embeddings and the second set of embeddings into a topological space.

Embodiment 24. The method of embodiment 23, further comprising: identifying a location of a first cluster of embeddings based on the first set of embeddings in the topological space; generating a representation of the first disease state based on the location of the first cluster; identifying a location of a second cluster of embeddings based on the second set of embeddings in the topological space; and generating a representation of the second disease state based on the location of the second cluster.

Embodiment 25. The method of embodiment 24, wherein the first set of embeddings and the second set of embeddings are time-stamped in the topological space.

Embodiment 26. The method of any one of embodiments 22-25, further comprising: applying a therapeutic agent to the first non-zero concentration of diseased live biological cells; obtaining a plurality of images captured at a plurality of time points of the first non-zero concentration of diseased live biological cells; inputting the plurality of images into the trained machine-learning model to obtain a plurality of embeddings representing positional and morphological changes over time in particular cellular substructures of the first non-zero concentration of diseased live biological cells; and determining, from at least a subset of the plurality of embeddings, an impact of the therapeutic agent on the reversion of the first non-zero concentration of diseased live biological cells from a diseased state.

Embodiment 27. The method of embodiment 26, wherein the therapeutic agent is a chemical treatment, a genetic treatment, or any combination thereof.

Embodiment 28. The method of embodiments 26 or 27, further comprising: determining a dosage for the therapeutic agent based on the plurality of embeddings.

Embodiment 29. The method of any one of embodiments 26-28, further comprising: determining one or more dose administration intervals for administering the therapeutic agent based on the plurality of embeddings.

Embodiment 30. The method of any one of embodiments 26-29, further comprising: providing a medical recommendation or administering the therapeutic agent to a patient having the disease.

Embodiment 31. The method of any one of embodiments 26-30, wherein evaluating the treatment candidate comprises: inputting the plurality of embeddings to a classifier to obtain a plurality of disease scores; and generating a time trend based on the plurality of disease scores.

Embodiment 32. The method of embodiment any one of embodiments 26-31, wherein evaluating the treatment candidate comprises: inputting the plurality of embeddings to a classifier to obtain a plurality of disease scores; and generating a plurality of distributions based on the plurality of disease scores.

Embodiment 33. The method of embodiments 31 or 32, wherein the classifier is a logistic regression model.

Embodiment 34. The method of any one of embodiments 22-33, wherein the first set of images and the second set of images comprise phase images.

Embodiment 35. The method of any one of embodiments 22-33, wherein the first set of images and the second set of images are generated based on fluorescence images or autofluorescence images.

Embodiment 36. The method of any one of embodiments 22-35, wherein the trained machine-learning model is a self-supervised machine-learning model.

Embodiment 37. The method of embodiment 36, wherein the trained machine-learning model comprises a neural network.

Embodiment 38. The method of any one of embodiments 22-37, wherein the trained machine-learning model is pre-trained using unlabeled images that do not depict biological samples.

Embodiment 39. The method of embodiment 38, wherein the trained machine-learning model is configured to be retrained using unlabeled images of biological samples.

Embodiment 40. A system for modeling a progression of a disease of interest having a plurality of disease states, comprising: one or more processors; a memory; and one or more programs, wherein the one or more programs are stored in the memory and configured to be executed by the one or more processors, the one or more programs including instructions for: obtaining a first set of images captured at a first plurality of time points of a first non-zero concentration of diseased live biological cells expressing a first disease state of the disease; obtaining a second set of images captured at a first plurality of time points of a second non-zero concentration of diseased live biological cells expressing a second disease state of the disease; inputting the first set of images into a trained machine-learning model to obtain a first set of embeddings representing positional and morphological characteristics in particular cellular substructures of the first non-zero concentration of diseased live biological cells; inputting the second set of images into the trained machine-learning model to obtain a second set of embeddings representing positional and morphological characteristics in particular cellular substructures of the second non-zero concentration of diseased live biological cells; generating the disease model based on the first set of embeddings and the second set of embeddings; and modeling a progression of the disease based on the disease model.

Embodiment 41. A non-transitory computer-readable storage medium storing one or more programs for modeling a progression of a disease of interest having a plurality of disease states, the one or more programs comprising instructions, which when executed by one or more processors of an electronic device having a display, cause the electronic device to perform the operations of: obtaining a first set of images captured at a first plurality of time points of a first non-zero concentration of diseased live biological cells expressing a first disease state of the disease; obtaining a second set of images captured at a first plurality of time points of a second non-zero concentration of diseased live biological cells expressing a second disease state of the disease; inputting the first set of images into a trained machine-learning model to obtain a first set of embeddings representing positional and morphological characteristics in particular cellular substructures of the first non-zero concentration of diseased live biological cells; inputting the second set of images into the trained machine-learning model to obtain a second set of embeddings representing positional and morphological characteristics in particular cellular substructures of the second non-zero concentration of diseased live biological cells; generating the disease model based on the first set of embeddings and the second set of embeddings; and modeling a progression of the disease based on the disease model.

Embodiment 42. A method of modeling a characteristic of interest of a cell culture comprising one or more live biological cells, comprising: obtaining a first set of one or more images capturing the cell culture at a first time point; inputting the first set of one or more images into a trained machine-learning model to obtain a first set of embeddings representing positional and morphological characteristics in particular cellular substructures of the cell culture; evaluating the characteristic of interest of the cell culture corresponding to the first time point based on the first set of embeddings to obtain a first set of one or more values; obtaining a second set of one or more images capturing the cell culture at a second time point; inputting the second set one or more images into the trained machine-learning model to obtain a second set of embeddings representing positional and morphological characteristics in particular cellular substructures of the cell culture; evaluating the characteristic of interest of the cell culture corresponding to the second time point based on the second set of embeddings to obtain a second set of one or more values; and determining, from the first set of one or more values and the second set of one or more values, a change of the characteristic of interest in the cell culture.

Embodiment 43. The method of embodiment 42, wherein the characteristic of interest is cell proliferation of the cell culture, wherein: i) the first set of one or more values indicates a predicted first proliferation level; ii) the second set of one or more values indicates a predicted second proliferation level; and iii) a rate of proliferation of the cell culture is determined from the predicted first cell proliferation level and the predicted second cell proliferation level.

Embodiment 44. The method of embodiment 43, further comprising: determining the in vitro and/or metabolic fitness of the cell culture based on the predicted first cell proliferation level and the predicted second cell proliferation level.

Embodiment 45. The method of embodiments 43 or 44, further comprising: comparing the rate of proliferation to a predefined threshold.

Embodiment 46. The method of embodiment 45, further comprising: if the rate of proliferation exceeds the predefined threshold: determining that the rate of proliferation is an abnormal proliferation rate; and terminating growth of the cell culture before a predefined endpoint of cell growth.

Embodiment 47. The method of any one of embodiments 43-46, further comprising: predicting the confluence of the cell culture for a third time point after the second time point based on the rate of proliferation of the cell culture.

Embodiment 48. The method of embodiment 47, further comprising: determining timing for passaging of the cell culture based on the predicted confluence of the cell culture.

Embodiment 49. The method of any one of embodiments 43-46, further comprising: determining timing for passaging of the cell culture based on the rate of proliferation.

Embodiment 50. The method of any one of embodiments 43-49, wherein the machine-learning model is a first machine-learning model, and wherein predicting the cell proliferation level comprises: inputting the first set of embeddings into a second machine-learning model to obtain the cell proliferation level corresponding to the first time point; and inputting the second set of embeddings into the second machine-learning model to obtain the cell proliferation level corresponding to the second time point.

Embodiment 51. The method of embodiment 50, further comprising: generating a time trend based on the predicted first cell proliferation level and the predicted second cell proliferation level.

Embodiment 52. The method of embodiments 50 or 51, wherein the second machine-learning model is a linear regression classifier.

Embodiment 53. The method of any one of embodiments 50-52, wherein the second machine-learning model is trained using a set of embeddings and a corresponding set of cell proliferation levels.

Embodiment 54. The method of embodiment 43, wherein the characteristic of interest is health of the cell culture, wherein: i) the first set of one or more values indicates a predicted first cell health level; ii) the second set of one or more values indicates a predicted second cell health level; and iii) a change of the health level of the cell culture is determined from the predicted first cell health level and the predicted second cell health level.

Embodiment 55. The method of embodiment 43, wherein the characteristic of interest is development of the cell culture, wherein: i) the first set of one or more values indicates a predicted first cell development level; ii) the second set of one or more values indicates a predicted second cell development level; and iii) a change of the development level of the cell culture is determined from the predicted first cell development level and the predicted second cell development level.

Embodiment 56. The method of any one of embodiments 43-55, wherein the first set of one or more of images and the second set of one or more images comprise phase images.

Embodiment 57. The method of any one of embodiments 43-55, wherein the first set of one or more of images and the second set of one or more images are generated from fluorescence images or autofluorescence images.

Embodiment 58. The method of any one of embodiments 43-57, wherein the trained machine-learning model is a self-supervised machine-learning model.

Embodiment 59. The method of any one of embodiments 43-58, wherein the trained machine-learning model is trained using unlabeled images of biological samples.

Embodiment 60. The method of any one of embodiments 43-59, wherein the one or more live biological cells are mammalian cells.

Embodiment 61. The method of any one of embodiments 43-60, wherein the one or more live biological cells are healthy cells.

Embodiment 62. The method of any one of embodiments 43-61, wherein the one or more live biological cells are diseased cells.

Embodiment 63. The method of any one of embodiments 43-62, further comprising, prior to obtaining a first set of one or more images: applying a perturbation and/or a therapeutic agent to the cell culture.

Embodiment 64. The method of embodiment 63, wherein the perturbation and/or the therapeutic agent is a chemical treatment, a genetic treatment, or any combination thereof.

Embodiment 65. A non-transitory computer-readable storage medium storing one or more programs for modeling a characteristic of interest of a cell culture comprising one or more live biological cells, the one or more programs comprising instructions, which when executed by one or more processors of an electronic device having a display, cause the electronic device to perform the operations of: obtaining a first set of one or more images capturing the cell culture at a first time point; inputting the first set of one or more images into a trained machine-learning model to obtain a first set of embeddings representing positional and morphological characteristics in particular cellular substructures of the cell culture; evaluating the characteristic of interest of the cell culture corresponding to the first time point based on the first set of embeddings to obtain a first set of one or more values; obtaining a second set of one or more images capturing the cell culture at a second time point; inputting the second set one or more images into the trained machine-learning model to obtain a second set of embeddings representing positional and morphological characteristics in particular cellular substructures of the cell culture; evaluating the characteristic of interest of the cell culture corresponding to the second time point based on the second set of embeddings to obtain a second set of one or more values; and determining, from the first set of one or more values and the second set of one or more values, a change of the characteristic of interest in the cell culture.

Embodiment 66. A system for modeling a characteristic of interest of a cell culture comprising one or more live biological cells, comprising: one or more processors; a memory; and one or more programs, wherein the one or more programs are stored in the memory and configured to be executed by the one or more processors, the one or more programs including instructions for: obtaining a first set of one or more images capturing the cell culture at a first time point; inputting the first set of one or more images into a trained machine-learning model to obtain a first set of embeddings representing positional and morphological characteristics in particular cellular substructures of the cell culture; evaluating the characteristic of interest of the cell culture corresponding to the first time point based on the first set of embeddings to obtain a first set of one or more values; obtaining a second set of one or more images capturing the cell culture at a second time point; inputting the second set one or more images into the trained machine-learning model to obtain a second set of embeddings representing positional and morphological characteristics in particular cellular substructures of the cell culture; evaluating the characteristic of interest of the cell culture corresponding to the second time point based on the second set of embeddings to obtain a second set of one or more values; and determining, from the first set of one or more values and the second set of one or more values, a change of the characteristic of interest in the cell culture.

Embodiment 67. A method for identifying one or more cell culture conditions for progressing one or more live biological cells towards a desired cell state, comprising: performing a plurality of cell culture condition identification cycles on the one or more live biological cells until a condition is met, wherein each cell culture condition identification cycle comprises: obtaining a set of one or more images capturing the one or more live biological cells; determining, from at least a subset of the set of images, a cell state of the one or more live biological cells; identifying a new cell culture condition for progressing the one or more live biological cells towards the desired cell state, by inputting the current cell state and the desired cell state into a trained machine-learning model; and applying the new cell culture condition to the one or more live biological cells; and identifying the one or more cell culture conditions, based on the outcomes of the plurality of cell culture condition identification cycles, for use in progressing live biological cells towards the desired cell state in future cell cultures.

Embodiment 68. The method of embodiment 67, wherein the one or more live biological cells are a first set of one or more live biological cells that are deposited in a first well, and the plurality of cell culture condition identification cycles is a first plurality of cell culture condition identification cycles, the method further comprising: depositing a second set of one or more live biological cells in a second well; performing a second plurality of cell culture condition identification cycles on the second set of one or more live biological cells, wherein the second plurality of cell culture condition identification cycles is different from the first plurality of cell culture condition identification cycles; and prioritizing one or more cell culture conditions in the first plurality of cell culture condition identification cycles and the second plurality of cell culture condition identification cycles based on the outcomes of the first plurality of cell culture condition identification cycles and the second plurality of cell culture condition identification cycles.

Embodiment 69. The method of embodiment 68, wherein the time frame for performing the first plurality of cell culture condition identification cycles overlaps with the time frame for performing the second plurality of cell culture condition identification cycles.

Embodiment 70. The method of embodiments 68 or 69, wherein the first well and the second well belong to the same multi-well plate.

Embodiment 71. The method of any one of embodiments 68-70, wherein the differences between the first plurality of cell culture condition identification cycles and the second plurality of cell culture condition identification cycles comprise cell culture medium ingredient differences, cell culture temperature differences, cell culture pressure exposure differences, and/or cell culture medium light exposure differences.

Embodiment 72. The method of any one of embodiments 67-71, wherein the condition is met when the desired cell state is achieved.

Embodiment 73. The method of any one of embodiments 67-71, wherein the condition is met when a predefined number of cell culture condition identification cycles are performed.

Embodiment 74. The method of any one of embodiments 67-73, wherein the trained machine-learning model is an active-learning machine-learning model.

Embodiment 75. The method of embodiment 74, wherein each cell culture condition identification cycle further comprises: prompting the user to provide one or more user inputs about the state of the one or more live biological cells after the new cell culture condition is applied; and retraining the active-learning machine-learning model based on the user inputs.

Embodiment 76. The method of embodiment 75, wherein the user is an individual.

Embodiment 77. The method of any one of embodiments 67-73, wherein the trained machine-learning model is a reinforcement-learning machine-learning model.

Embodiment 78. The method of embodiment 77, wherein each cell culture condition identification cycle further comprises: determining the cell state of the one or more live biological cells after the new cell culture condition applied; and retraining the reinforcement-learning machine-learning model based on the determined cell state.

Embodiment 79. The method of any one of embodiments 67-78, wherein the set of one or more images comprise phase images.

Embodiment 80. The method of any one of embodiments 67-78, wherein the set of one or more images are generated based on fluorescence images or autofluorescence images.

Embodiment 81. The method of any one of embodiments 67-80, wherein the one or more live biological cells are induced pluripotent stem cells.

Embodiment 82. The method of embodiment 81, wherein the desired cell state is a non-pluripotent cell state.

Embodiment 83. The method of any one of embodiments 67-82, wherein the one or more live biological cells are healthy cells.

Embodiment 84. The method of embodiment 83, wherein the desired cell state is a diseased cell state.

Embodiment 85. The method of any one of embodiments 67-84, wherein the new cell culture condition is a perturbagen.

Embodiment 86. The method of embodiment 85, wherein the perturbagen is a chemical treatment, a genetic treatment, or any combination thereof.

Embodiment 87. The method of any one of embodiments 67-84, wherein the new cell culture condition is a therapeutic agent.

Embodiment 88. The method of embodiment 87, wherein the therapeutic agent is a chemical treatment, a genetic treatment, or any combination thereof.

Embodiment 89. The method of any one of embodiments 67-84, wherein the new cell culture condition is a temperature, pressure, and/or light exposure.

Embodiment 90. The method of any one of embodiments 67-89, wherein the applying the new type of cell culture condition to the one or more live biological cells is automated by one or more electronic devices.

Embodiment 91. The method of any one of embodiments 67-90, wherein the one or more live biological cells are mammalian cells.

Embodiment 92. A non-transitory computer-readable storage medium storing one or more programs for identifying one or more cell culture conditions for progressing one or more live biological cells towards a desired cell state, the one or more programs comprising instructions, which when executed by one or more processors of an electronic device having a display, cause the electronic device to perform the operations of: performing a plurality of cell culture condition identification cycles on the one or more live biological cells until a condition is met, wherein each cell culture condition identification cycle comprises: obtaining a set of one or more images capturing the one or more live biological cells; determining, from at least a subset of the set of images, a cell state of the one or more live biological cells; identifying a new cell culture condition for progressing the one or more live biological cells towards the desired cell state, by inputting the current cell state and the desired cell state into a trained machine-learning model; and applying the new cell culture condition to the one or more live biological cells; and identifying the one or more cell culture conditions, based on the outcomes of the plurality of cell culture condition identification cycles, for use in progressing live biological cells towards the desired cell state in future cell cultures.

Embodiment 93. A system for determining an impact of a therapeutic agent on diseased cells, comprising: one or more processors; a memory; and one or more programs, wherein the one or more programs are stored in the memory and configured to be executed by the one or more processors, the one or more programs including instructions for: performing a plurality of cell culture condition identification cycles on the one or more live biological cells until a condition is met, wherein each cell culture condition identification cycle comprises: obtaining a set of one or more images capturing the one or more live biological cells; determining, from at least a subset of the set of images, a cell state of the one or more live biological cells; identifying a new cell culture condition for progressing the one or more live biological cells towards the desired cell state, by inputting the current cell state and the desired cell state into a trained machine-learning model; and applying the new cell culture condition to the one or more live biological cells; and identifying the one or more cell culture conditions, based on the outcomes of the plurality of cell culture condition identification cycles, for use in progressing live biological cells towards the desired cell state in future cell cultures.

Embodiment 94: A method of modeling a progression of a neurological disease of interest, comprising: obtaining a first set of images captured at a first plurality of time points of one or more healthy live neurological cells or a first set of images captured at a first plurality of time points of one or more regions from healthy live neurological cells; obtaining a second set of images captured at a second plurality of time points of one or more diseased live neurological cells or a second set of images captured at a second plurality of time points of one or more regions from healthy live neurological cells; inputting the first set of images into a trained machine-learning model to obtain a first set of embeddings representing positional and morphological characteristics of neurological substructures in the one or more healthy live neurological cells; inputting the second set of images into the trained machine-learning model to obtain a second set of embeddings representing positional and morphological characteristics in neurological substructures of the one or more diseased live neurological cells; generating a disease model of the neurological disease of interest based on the first set of embeddings and the second set of embeddings; and modeling a progression of the neurological disease of interest based on the disease model.

Embodiment 95: The method of embodiment 94, wherein generating the disease model of the neurological disease of interest comprises: mapping the first set of embeddings and the second set of embeddings into a topological space.

Embodiment 96: The method of embodiment 95, wherein modeling the progression of the neurological disease of interest comprises: determining the progression of the neurological disease of interest based on time-stamps associated with the first set of embeddings and the second set of embeddings.

Embodiment 97: The method of any one of embodiments 94-96, wherein: the first set of images depict a first sub-cellular structure in the one or more healthy live neurological cells and the second set of images depict the first sub-cellular structure in the one or more diseased live neurological cells; or the first set of images depict a second sub-cellular structure in the one or more healthy live neurological cells and the second set of images depict the second sub-cellular structure in the one or more diseased live neurological cells.

Embodiment 98: The method of any one of embodiments 94-97, wherein the one or more regions from healthy live neurological cells comprises the nucleus and/or cytoplasm of the healthy live neurological cells and the one or more regions from diseased live neurological cells comprises the nucleus and/or cytoplasm of the diseased live neurological cells, the method further comprise: determining a first abundance level of a disease signal in the nucleus of the diseased live neurological cells; and determining a second abundance level of the disease signal in cytoplasm of the diseased live neurological cells.

Embodiment 99: The method of embodiment 98, wherein: determining the first abundance level comprises determining an amount of the disease signal present in the nucleus of the diseased live neurological cells based on the second set of images; and determining the second abundance level comprises determining an amount of the disease signal present in the cytoplasm of the diseased live neurological cells based on the second set of images.

Embodiment 100: The method of embodiment 98, further comprising: for each of the diseased live neurological cells, computing and determining a disease infiltration value based on the first abundance level and the second abundance level.

Embodiment 101: The method of embodiment 100, wherein computing the disease infiltration value comprises: determining, for each of the diseased live neurological cells, a ratio of the first abundance level to the second abundance level.

Embodiment 102: The method of embodiment 100, wherein the lower the ratio of the first abundance level to the second abundance level, the greater the disease of interest has progressed.

Embodiment 103: The method of any one of embodiments 100-102, further comprising: encoding the computed disease infiltration value into each of the diseased live neurological cells; and generating a visualization of the second set of embeddings encoded with the disease infiltration value of each of the diseased live neurological cells.

Embodiment 104: The method of embodiments 94, wherein the one or more healthy live neurological cells comprise one or more healthy neurite cell regions and the one or more diseased live neurological cells comprise one or more diseased neurite cell regions, the method further comprises: determining an accumulation level of a disease signal of the disease of interest within the one or more diseased neurite cell regions.

Embodiment 105: The method of embodiment 104, wherein determining the accumulation level of the disease signal comprises: determining an amount of the disease signal present in a neurite of the one or more diseased live neurological neurite cells based on the second set of images.

Embodiment 106: The method of any one of embodiments 104-105, further comprising: for each of the one or more diseased neurite cell regions, computing determining a disease infiltration value based on the accumulation level.

Embodiment 107: The method of embodiment 106, wherein the lower the disease infiltration value is, the greater the disease of interest has progressed.

Embodiment 108: The method of any one of embodiments 106-107, further comprising: encoding the computed disease infiltration value into each of the one or more diseased neurite cell regions; and generating a visualization of the second set of embeddings encoded with the disease infiltration value of each of the one or more diseased neurite cell regions.

Embodiment 109: The method of any one of embodiments 94-108, wherein the first set of images and the second set of images comprise phase images.

Embodiment 110: The method of any one of embodiments 94-109, wherein the first set of images and the second set of images are generated based on fluorescence images or autofluorescence images.

Embodiment 111: The method of any one of embodiments 94-110, wherein the trained machine-learning model is a self-supervised machine-learning model.

Embodiment 112: The method of embodiment 111, wherein the trained machine-learning model comprises a neural network.

Embodiment 113: The method of embodiment 111, wherein the trained machine-learning model is trained using contrastive learning.

Embodiment 114: A non-transitory computer-readable storage medium storing one or more programs for modeling a progression of a neurological disease of interest, the one or more programs comprising instructions, which when executed by one or more processors of an electronic device, cause the electronic device to effectuate operations comprising:

obtaining a first set of images captured at a first plurality of time points of one or more healthy live neurological cells or a first set of images captured at a first plurality of time points of one or more regions from healthy live neurological cells; obtaining a second set of images captured at a second plurality of time points of one or more diseased live neurological cells or a second set of images captured at a second plurality of time points of one or more regions from diseased live neurological cells; inputting the first set of images into a trained machine-learning model to obtain a first set of embeddings representing positional and morphological characteristics of neurological substructures in the one or more healthy live neurological cells; inputting the second set of images into the trained machine-learning model to obtain a second set of embeddings representing positional and morphological characteristics in neurological substructures of the one or more diseased live neurological cells; generating a disease model of the neurological disease of interest based on the first set of embeddings and the second set of embeddings; and modeling a progression of the neurological disease of interest based on the disease model.

Embodiment 115: A system for modeling a progression of a neurological disease of interest, comprising: one or more processors; a memory; and one or more programs, wherein the one or more programs are stored in the memory and configured to be executed by the one or more processors to: obtain a first set of images captured at a first plurality of time points of one or more healthy live neurological cells or a first set of images captured at a first plurality of time points of one or more regions from healthy live neurological cells; obtain a second set of images captured at a second plurality of time points of one or more diseased live neurological cells a second set of images captured at a second plurality of time points of one or more regions from diseased live neurological cells; input the first set of images into a trained machine-learning model to obtain a first set of embeddings representing positional and morphological characteristics of neurological substructures in the one or more healthy live neurological cells; input the second set of images into the trained machine-learning model to obtain a second set of embeddings representing positional and morphological characteristics in neurological substructures of the one or more diseased live neurological cells; generate a disease model of the neurological disease of interest based on the first set of embeddings and the second set of embeddings; and model a progression of the neurological disease of interest based on the disease model.

What is claimed is:

1. A system for modeling a characteristic of interest of a cell culture comprising one or more live mammalian cells, comprising:
   one or more processors;
   a memory; and
   one or more programs, wherein the one or more programs are stored in the memory and configured to be executed by the one or more processors to:
      obtain a first set of one or more images capturing the cell culture at a first time point;
      input the first set of one or more images into a trained machine-learning model to obtain a first set of embedding vectors representing positional and morphological characteristics in particular cellular substructures of the cell culture;
      evaluate the characteristic of interest of the cell culture corresponding to the first time point based on the first set of embedding vectors to obtain a first set of one or more values;
      obtain a second set of one or more images capturing the cell culture at a second time point;
      input the second set of one or more images into the trained machine-learning model to obtain a second set of embedding vectors representing positional and morphological characteristics in particular cellular substructures of the cell culture;

evaluate the characteristic of interest of the cell culture corresponding to the second time point based on the second set of embedding vectors to obtain a second set of one or more values; and determine, from the first set of one or more values and the second set of one or more values, a change of the characteristic of interest in the cell culture.

2. The system of claim 1, wherein the characteristic of interest is cell proliferation of the cell culture, wherein:
i) the first set of one or more values indicates a predicted first proliferation level;
ii) the second set of one or more values indicates a predicted second proliferation level; and
iii) a rate of proliferation of the cell culture is determined from the predicted first proliferation level and the predicted second proliferation level.

3. The system of claim 2, wherein the one or more programs, when executed by the one or more processors, cause the system to:
determine the in vitro and/or metabolic fitness of the cell culture based on the predicted first proliferation level and the predicted second proliferation level.

4. The system of claim 2, wherein the one or more programs, when executed by the one or more processors, cause the system to: compare the rate of proliferation to a predefined threshold.

5. The system of claim 4, wherein the one or more programs, when executed by the one or more processors, cause the system to:
based on the rate of proliferation being determined to exceed the predefined threshold:
determine that the rate of proliferation is an abnormal proliferation rate; and
terminate growth of the cell culture before a predefined endpoint of cell growth.

6. The system of claim 2, wherein the one or more programs, when executed by the one or more processors, cause the system to:
predict a confluence of the cell culture for a third time point after the second time point based on the rate of proliferation of the cell culture.

7. The system of claim 6, wherein the one or more programs, when executed by the one or more processors, cause the system to:
determine timing for passaging of the cell culture based on the predicted confluence of the cell culture.

8. The system of claim 2, wherein the one or more programs, when executed by the one or more processors, cause the system to:
determine timing for passaging of the cell culture based on the rate of proliferation.

9. The system of claim 2, wherein the trained machine-learning model is a first machine-learning model, predicting a cell proliferation level comprises:
inputting the first set of embedding vectors into a second machine-learning model to obtain the cell proliferation level corresponding to the first time point; and
inputting the second set of embedding vectors into the second machine-learning model to obtain the cell proliferation level corresponding to the second time point.

10. The system of claim 9, wherein the one or more programs, when executed by the one or more processors, cause the system to:
generate a time trend based on the predicted first cell proliferation level and the predicted second cell proliferation level.

11. The system of claim 9, wherein the second machine-learning model is a linear regression classifier.

12. The system of claim 9, wherein the second machine-learning model is trained using a set of embedding vectors and a corresponding set of cell proliferation levels.

13. The system of claim 2, wherein the characteristic of interest is health of the cell culture, wherein:
i) the first set of one or more values indicates a predicted first cell health level;
ii) the second set of one or more values indicates a predicted second cell health level; and
iii) a change of the health level of the cell culture is determined from the predicted first cell health level and the predicted second cell health level.

14. The system of claim 2, wherein the characteristic of interest is development of the cell culture, wherein:
i) the first set of one or more values indicates a predicted first cell development level;
ii) the second set of one or more values indicates a predicted second cell development level; and
iii) a change of the development level of the cell culture is determined from the predicted first cell development level and the predicted second cell development level.

15. The system of claim 2, wherein the first set of one or more of images and the second set of one or more images comprise phase images.

16. The system of claim 2, wherein the first set of one or more of images and the second set of one or more images are generated from fluorescence images or autofluorescence images.

17. The system of claim 2, wherein the trained machine-learning model is a self-supervised machine-learning model.

18. The system of claim 2, wherein the trained machine-learning model is trained using unlabeled images of biological samples.

19. The system of claim 2, wherein the one or more live biological cells are healthy cells.

20. The system of claim 2, wherein the one or more live biological cells are diseased cells.

21. The system of claim 2, wherein the one or more programs, when executed by the one or more processors, cause the system to, prior to obtaining a first set of one or more images:
apply a perturbation and/or a therapeutic agent to the cell culture.

22. The system of claim 21, wherein the perturbation and/or the therapeutic agent is a chemical treatment, a genetic treatment, or any combination thereof.

23. A non-transitory computer-readable storage medium storing one or more programs for modeling a characteristic of interest of a cell culture comprising one or more live mammalian cells, the one or more programs comprising instructions, which when executed by one or more processors of an electronic device having a display, cause the electronic device to perform operations comprising:
obtaining a first set of one or more images capturing the cell culture at a first time point;
inputting the first set of one or more images into a trained machine-learning model to obtain a first set of embedding vectors representing positional and morphological characteristics in particular cellular substructures of the cell culture;
evaluating the characteristic of interest of the cell culture corresponding to the first time point based on the first set of embedding vectors to obtain a first set of one or more values;

obtaining a second set of one or more images capturing the cell culture at a second time point;

inputting the second set one or more images into the trained machine-learning model to obtain a second set of embedding vectors representing positional and morphological characteristics in particular cellular substructures of the cell culture;

evaluating the characteristic of interest of the cell culture corresponding to the second time point based on the second set of embedding vectors to obtain a second set of one or more values; and determining, from the first set of one or more values and the second set of one or more values, a change of the characteristic of interest in the cell culture.

24. A method of modeling a characteristic of interest of a cell culture comprising one or more live mammalian cells, comprising:

obtaining a first set of one or more images capturing the cell culture at a first time point;

inputting the first set of one or more images into a trained machine-learning model to obtain a first set of embedding vectors representing positional and morphological characteristics in particular cellular substructures of the cell culture;

evaluating the characteristic of interest of the cell culture corresponding to the first time point based on the first set of embedding vectors to obtain a first set of one or more values;

obtaining a second set of one or more images capturing the cell culture at a second time point;

inputting the second set one or more images into the trained machine-learning model to obtain a second set of embedding vectors representing positional and morphological characteristics in particular cellular substructures of the cell culture;

evaluating the characteristic of interest of the cell culture corresponding to the second time point based on the second set of embedding vectors to obtain a second set of one or more values; and determining, from the first set of one or more values and the second set of one or more values, a change of the characteristic of interest in the cell culture.

* * * * *